United States Patent
Fuchs et al.

(10) Patent No.: US 11,840,712 B2
(45) Date of Patent: *Dec. 12, 2023

(54) ENGINEERING OF DNASE ENZYMES FOR MANUFACTURING AND THERAPY

(71) Applicant: Neutrolis, Inc., Cambridge, MA (US)

(72) Inventors: Tobias A. Fuchs, Wellesley, MA (US); Abdul Hakkim R., Cambridge, MA (US)

(73) Assignee: Neutrolis, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/210,129

(22) Filed: Mar. 23, 2021

(65) Prior Publication Data
US 2021/0207114 A1    Jul. 8, 2021

Related U.S. Application Data

(63) Continuation of application No. 16/697,502, filed on Nov. 27, 2019, now Pat. No. 10,988,746, which is a continuation of application No. PCT/US2019/055178, filed on Oct. 8, 2019.

(60) Provisional application No. 62/846,904, filed on May 13, 2019, provisional application No. 62/808,601, filed on Feb. 21, 2019, provisional application No. 62/779,104, filed on Dec. 13, 2018, provisional application No. 62/775,563, filed on Dec. 5, 2018, provisional application No. 62/742,682, filed on Oct. 8, 2018.

(51) Int. Cl.
| | | |
|---|---|---|
| *C12N 9/22* | (2006.01) | |
| *C12P 21/02* | (2006.01) | |
| *C07K 14/76* | (2006.01) | |
| *A61K 9/00* | (2006.01) | |
| *A61K 38/47* | (2006.01) | |

(52) U.S. Cl.
CPC ............. *C12N 9/22* (2013.01); *A61K 9/0029* (2013.01); *A61K 38/47* (2013.01); *C07K 14/76* (2013.01); *C12P 21/02* (2013.01); *C12Y 301/21001* (2013.01); *C07K 2319/31* (2013.01)

(58) Field of Classification Search
CPC ........ C12N 9/22; A61K 9/0029; A61K 38/47; A61K 9/0019; C07K 14/76; C07K 2319/31; C12P 21/02; C12Y 301/21001; Y02A 50/30
See application file for complete search history.

(56) References Cited

U.S. PATENT DOCUMENTS

| | | |
|---|---|---|
| 6,270,989 B1 | 8/2001 | Treco et al. |
| 6,482,626 B2 | 11/2002 | Baker et al. |
| 6,656,685 B2 | 12/2003 | Utermohlen et al. |
| 7,612,032 B2 | 11/2009 | Genkin et al. |
| 8,388,951 B2 | 3/2013 | Genkin et al. |
| 8,431,123 B2 | 4/2013 | Genkin et al. |
| 8,535,663 B2 | 9/2013 | Genkin et al. |
| 8,796,004 B2 | 8/2014 | Genkin et al. |
| 8,916,151 B2 | 12/2014 | Genkin et al. |
| 9,072,733 B2 | 7/2015 | Genkin et al. |
| 9,149,513 B2 | 10/2015 | Bartoov et al. |
| 9,198,957 B2 | 12/2015 | Ratner et al. |
| 9,205,133 B2 | 12/2015 | Dawson et al. |
| 9,248,166 B2 | 2/2016 | Gerkin et al. |
| 9,402,884 B2 | 8/2016 | Burns |
| 9,642,822 B2 | 5/2017 | Wagner |
| 9,770,492 B2 | 9/2017 | Genkin et al. |
| 9,845,461 B2 | 12/2017 | Genkin et al. |
| 9,867,871 B2 | 1/2018 | Jain |
| 10,617,743 B2 | 4/2020 | Genkin et al. |
| 10,696,956 B2 | 6/2020 | Fuchs et al. |
| 2004/0138156 A1 | 7/2004 | Schneider et al. |
| 2009/0010966 A1 | 1/2009 | Davis et al. |
| 2013/0149749 A1 | 6/2013 | Holliger et al. |
| 2013/0236945 A1 | 9/2013 | Song et al. |
| 2014/0080178 A1* | 3/2014 | Schnorr ............ C12N 15/8246 435/254.5 |
| 2014/0199329 A1 | 7/2014 | Wagner et al. |
| 2016/0251638 A1 | 9/2016 | Posada et al. |
| 2016/0376366 A1 | 12/2016 | Chang et al. |

(Continued)

FOREIGN PATENT DOCUMENTS

| | | |
|---|---|---|
| WO | WO 2011053982 | 5/2011 |
| WO | WO 2011131772 | 10/2011 |
| WO | WO 2012/149440 | * 11/2012 |

(Continued)

OTHER PUBLICATIONS

Al-Mayouf et al., Loss-of-function variant in DNASEIL3 causes a familial form of systemic lupus erythematosus, Nature Genetics, 2011, vol. 43, No. 12, pp. 1186-1188.

(Continued)

*Primary Examiner* — Delia M Ramirez

(74) *Attorney, Agent, or Firm* — Morgan, Lewis & Bockius LLP

(57) ABSTRACT

The present disclosure provides engineered human extracellular DNASE proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by neutrophil extracellular trap (NET) accumulation and/or release. In accordance with the invention, the DNase variant has advantages for therapy and/or large-scale manufacturing.

19 Claims, 24 Drawing Sheets

Specification includes a Sequence Listing.

(56) References Cited

U.S. PATENT DOCUMENTS

2017/0196945 A1 7/2017 Wagner et al.
2020/0024585 A1 1/2020 Fuchs et al.

FOREIGN PATENT DOCUMENTS

| WO | WO 2015066550 | 5/2015 |
|---|---|---|
| WO | WO 2016139659 | 9/2016 |
| WO | WO 2018015474 | 1/2018 |
| WO | WO 2018064681 | 4/2018 |
| WO | WO 2018134403 | 7/2018 |
| WO | WO 2018134419 | 7/2018 |
| WO | WO 2019036719 | 2/2019 |

OTHER PUBLICATIONS

Andersen et al. 2014; Extending serum half-life of albumin by engineering neonatal FC receptor (FcRn) binding. Journal of Biological Chemistry. 289(19): 13492-13502.
Barnes et al. "Targeting potential drivers of COVID-19: Neutrophil extracellular traps", J. Exp. Med., 2020, vol. 217, pp. 1-7.
Baron et al., Cloning and characterization of an actin-resistant DNase I-like endonuclease secreted by macrophages, Gene, 1998, vol. 215 pp. 291-301.
Bassi et al. 2012; Regenerative therapies for diabetic microangiopathy. Experimental Diabetes Research. Article ID 916560, pp. 1-11.
Berntsson et al., "Structural insight into DNA binding and oligomerization of the multifunctional Cox protein of bacteriophage P2", Nucleic Acids Research, vol. 42, No. 4, 2014, pp. 2725-2735.
Boettcher et al. "Therapeutic targeting of extracellular DNA improves the outcome of intestinal ischemic reperfusion injury in neonatal rats," Scientific Reports, Nov. 13, 2017.
Branden et al., "Prediction, Engineering, and ■ Design of Protein Structures", Introduction to Protein Structure, Garland Publishing Inc., New York, p. 247, 1991.
Brill, et al., "Neutrophil extracellular traps promote deep vein thrombosis in mice", J Thromb Haemost. Jan. 2012 ; 10(1): 136-144.
Brinkmann, et all., "Neutrophil extracellular traps: Is immunity the second function of chromatin?", J. Cell Biol. vol. 198 No. 5 773-783, (2012).
Bruschi et al., Neutrophil extracellular traps (NET) induced by different stimuli: A comparative proteomic analysis, PLOS One, 2019, pp. 1-18.
Carbonella et al., An autosomal recessive DNASEIL3-related autoimmune disease with unusual clinical presentation mimicking systemic lupus erythematosus, Lupus, 2017, vol. 26, pp. 768-772.
Chica et al., Semi-rational approaches to engineering enzyme activity: combining the benefits of directed evolution and rational design. Curr. Opi. Biotechnol., 2005, vol. 16: 378-384.
CORDIS_project_628264_en, Degradation of Neutrophil Extracellular Traps and its impact on thrombolysis, https://cordis.europa.eu/project/id/628264, 2016, 3 pages.
De Meyer et al. "Extracellular Chromatin Is an Important Mediator of Ischemic Stroke in Mice," Arteriosclerosis, Thrombosis, and Vascular Biology, May 24, 2012 (May 24, 2012), vol. 32, No. 8, pp. 1884-1891. entire document.
Fuchs, et al., "Extracellular DNA traps promote thrombosis, " PNAS, 2010, vol. 107, No. 36, pp. 15880-15885.
Fuchs, et al., "NET impact on deep vein thrombosis," Arterioscler Thromb Vasc Biol. Aug. 2012 ; 32(8): 1777-1783.
Hakkim et al., "Impairment of neutrophil extracellular trap degradation is associated with lupus nephritis", PNAS, vol. 107, No. 21, 2010, pp. 9813-9818.
Hattori et al. 2018; Nucleic-acid based gene therapy approaches for sepsis. European Journal of Pharmacology. 833: 403-410.
International Search Report and Written Opinion for International Application No. PCT/US2018/047084 , dated Feb. 15, 2019, 23 pages.

Jimenez-Alcazar, M, et al. Host DNases Prevent Vascular Occlusion by Neutrophil Extracellular Traps. Science. Dec. 1, 2017, vol. 358; pp. 1202-1206.
Keyel, "Dnases in health and disease", Developmental Biology, vol. 429, 2017, pp. 1-11.
Kobayashi et al., "Synchronous Growth of Pichia Pastoris for a High-Rate Production of DNase1 at Microquantities", Department of Chemical Engineering. Toyko Institute of Technology. On-Line No. 833, 2004 pp. 1-6.
Koyama, et al., "DNase γ, DNase I, and caspase-activated DNase cooperate to degrade dead cells," Genes to Cells 21, 1150-1163 (2016).
Landhuis, "Spider-Man' Immune Response May Promote Severe COVID-19", Sci. Am., 2020, pp. 1-7.
Napirei et al. 2009; Murine serum nucleases-contrasting effects of plasmin and heparin on the activities of DNase1 and DNase1-lie 3 (DNase1l3). FEBS Journal. 276: 1059-1073.
Onuora, "DNASE1L3 prevents anti-DNA responses", Nature Rev. Rheumatol., 2016, vol. 12 No. 437, 1 page.
Özçakar et al., DNASE1L3 Mutations in Hypocomplementemic Urticarial Vasculitis Syndrome, Arthritis & Rheumatism, 2013, vol. 65, No. 8, pp. 2183-2189.
Parsiegla et al., The Structure of Human DNase I Bound to Magnesium and Phosphate Ions Points to a Catalytic Mechanism Common to Members of the DNase I-like Superfamily, Biochemistry, 2012, vol. 51, pp. 10250-10258.
Perini et al., "Topical application of Acheflan on rat skin injury accelerates wound healing: a histopathological, immunohistochemical and biochemical study", BMC Complementary and Alternative Medicine, 2015, vol. 15, No. 203, pp. 1-8.
Piccolo et al., "Intrapleural Tissue Plasminogen Activator and Deoxyribonuclease for Pleural Infection; An Effective and Safe Alternative to Surgery", AnnalsATS, vol. 11, No. 9, 2014 , pp. 1419-1425.
Reizis, "Project 3: The role of DNASE1L3 and its DNA substrate in lupus", National Institute of Health (NIH), 2015, 5 pages.
Rodriguez et al., Gen Bank accession No. 013609 Sep. 27, 2017.
Sadowski et al., "The sequence-structure relationship and protein function prediction", Current Opinion in Structural Biology 19:357-362, 2009.
Saito et al., Apoptotic DNA endonuclease (DNase-γ ) gene transfer induces cell death accompanying DNA fragmentation in human glioma cells, Journal of Neuro-Oncology, 2003, vol. 63, pp. 25-31.
Seffernick, et al., "Melamine deaminase and Atrazine Chlorohydrolase: 98 Percent Identical but Functionally Different", Journal of Bacteriology, 2001, pp. 2405-2410.
Shiokawa et al. 2003; Identification of two functional nuclear localization signals in DNase gamma and their roles in its apoptotic DNase activity. Biochem. J. 376: 377-381.
Shiokawa et al., "Characterization of Human DNase I Family Endonucleases and Activation of DNase γ during Apoptosis", Biochemistry 2001, 40, pp. 143-152.
Shiokawa et al. 1998; Molecular cloning and expression of a cDNA encoding an apoptotic endonuclease DNase gamma. Biochem. J. 332: 713-720.
Sisirak et al., "Digestion of Chromatin in Apoptotic Cell Microparticles Prevents Autoimmunity", Cell vol. 166, 2016 , pp. 88-101.
Tang et al., "Identification of Dehalobacter Reductive Dehalogenases that Catalyse Dechlorination of Chloroform, 1,1,1-trichloroethane and 1,1-dichloroethane", Phil Trans R Soc B, 368, Mar. 18, 2012, 1-10, 2013.
Varjú, et al., Fibrinolysis at the Interface of Thrombosis and Inflammation—The Role of Neutrophil Extracellular Traps, Hungarian Scientific Research Fund, Department of Medical Biochemistry, Semmelweis University, Budapest, Hungary, 2014, p. 1-59.
Wang et al., "Targeting the extracellular scavenger DNASE1L3 on SLE", J Xiangya Med, 2017, 3 pages.
Whisstock et al. Quaterly Reviews of Biophysics, 2003, "Prediction of protein function from protein sequence and structure", 36(3): 307-340.
Wilber et al., "Deoxyribonuclease I-like I11 Is an Inducible Macrophage Barrier to Liposomal Transfection", MolecularTherapy, vol. 6, No. 1, 2002, pp. 35-42.

(56) References Cited

OTHER PUBLICATIONS

Witkowski et al., "Conversion of a β-Ketoacyl Synthase to a Malonyl Decarboxylase by Replacement of the Active-Site Cysteine with Glutamine", Biochemistry 1999, 38, pp. 11643-11650.

* cited by examiner

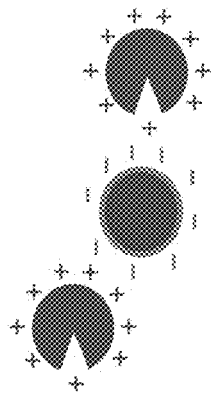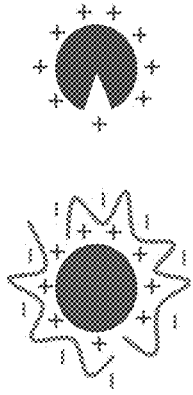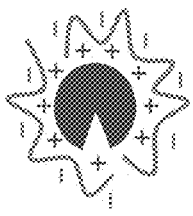

FIG. 7

Mutation of identified trypsin cleavage sites

| # | AA in D1L3 (SEQ ID NO: 4) | Amino Acid Substitution | D1 (SEQ ID NO: 1) Building Block Mutation |
|---|---|---|---|
| 1 | R22 | R22A/V/S, R22H/Q/E | M21_R22delinsLK |
| 2 | R29 | R29A/V/S, R29H/Q/E | V28_S30delinsIQT |
| 3 | R51 | R51A/V/S, R51H/Q/E | N/A (conserved residue) |
| 4 | R66 | R66A/V/S, R66H/Q/E | N64_I70delinsHLTAVGK |
| 5 | R80 | R80A/V/S, R80H/Q/E | R77_I83delinsQDAPD |
| 6 | R81 | R81A/V/S, R81H/Q/E | R77_I83delinsQDAPD |
| 7 | R95 | R95A/V/S, R95H/Q/E | N/A (conserved residue) |
| 8 | K99 | R99A/V/S, R99/H/Q/E | N/A (conserved residue) |
| 9 | R115 | R115A/V/S, R115H/Q/E | V113_R115delinsAVD |
| 10 | K147 | K147A/V/S, K147H/Q/E | K147_D148delinsRE |
| 11 | K163 | K163A/V/S, K163H/Q/E | K163A |
| 12 | K180 | K180A/V/S, K180H/Q/E | K180_A181delinsGL |
| 11 | R208 | R208A/V/S, R208H/Q/E | R208W |
| 12 | R212 | R212A/V/S, R212H/Q/E | R212T |
| 13 | R235 | K235A/V/S, K235H/Q/E | N/A (conserved residue) |
| 14 | R239 | K239A/V/S, K239H/Q/E | L238_R239delinsVA |
| 15 | K250 | K250A/V/S, K250H/Q/E | K250D |
| 16 | K262 | K262A/V/S, K262H/Q/E | K262G |

Selection of Amino Acid Substitution:
Grantham`s distance

Arg (R) / His (H): 29
Arg (R) / Glu (E): 54
Arg (R) / Gln (Q): 53

Lys (K) / His (E): 32
Lys (K) / Gln (H): 54
Lys (K): Glu (E): 56

FIG. 9

Mutation of predicted plasmin cleavage sites

| # | AA in D1L3 (SEQ ID NO 4) | Amino Acid Substitution | D1 (SEQ

FIG. 11

Mutation of identified plasmin cleavage sites

| # | AA in D1L3 (SEQ ID NO: 4) | Amino Acid Substitution | D1 (SEQ ID NO: 1) Building Block Mutation |
|---|---|---|---|
| 1 | R22 | R22H/Q/E | M21_R22delinsLK |
| 2 | R29 | R29H/Q/E | V28_S30delinsIQT |
| 3 | K45 | K45H/Q/E | N/A (conserved residue) |
| 4 | K47 | K47H/Q/E | K47_K50delinsQILS |
| 5 | K74 | K74H/Q/E | M72_K74delinsLDN |
| 6 | R81 | R81H/Q/E | R77_I83delinsQDAPD |
| 7 | R92 | R92H/Q/E | S91_R92delinsEP |
| 8 | K107 | K107H/Q/E | K107_L110delinsRPDQ |
| 9 | K176 | K176H/Q/E | K176_R178delinsQEK |
| 10 | R212 | R212H/Q/E | R212T |
| 11 | K226 | R226H/Q/E | V225_S228delinsATP |
| 12 | K227 | K227H/Q/E | V225_S228delinsATP |
| 13 | K250 | K250H/Q/E | K250D |
| 14 | K259 | K259H/Q/E | K259A |
| 15 | K262 | K262H/Q/E | K262G |

Selection of Amino Acid Substitution:
Grantham`s distance

Arg (R) / His (H): 29
Arg (R) / Glu (E): 54
Arg (R) / Gln (Q): 53

Lys (K) / His (E): 32
Lys (K) / Gln (H): 54
Lys (K): Glu (E): 56

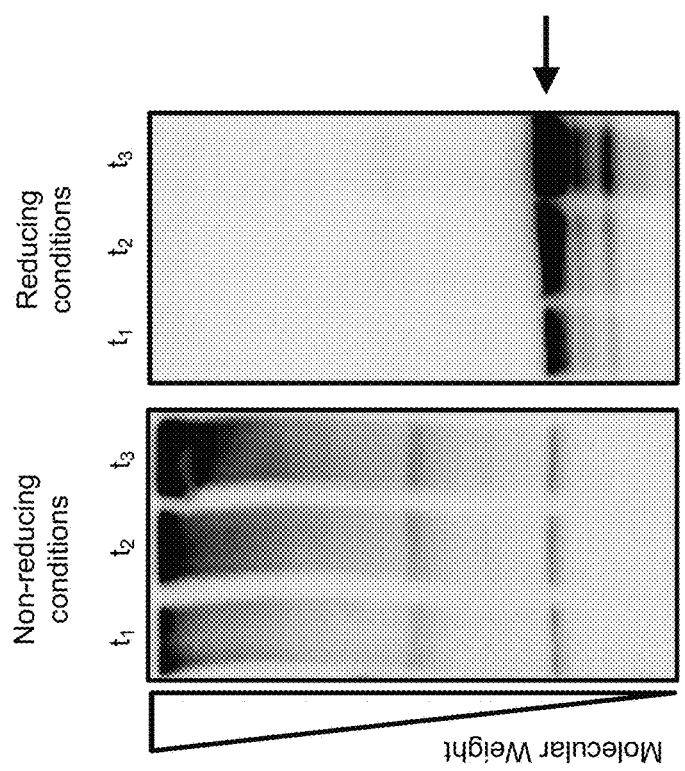
FIG. 12B
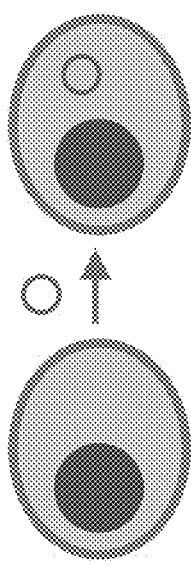
FIG. 12A
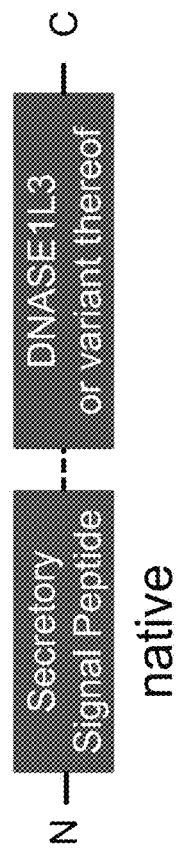

FIG. 14

Mutation of identified plasmin cleavage sites

| # | AA in D1L3 (SEQ ID NO: 4) | Amino Acid Substitution | D1 (SEQ ID NO: 1) Building Block Mutation |
|---|---|---|---|
| 1 | C24 | C24A/S/G | C24_S25delinsAA |
| 2 | C52 | C52A/S/G | C52Y |
| 3 | C68 | C68A/S/G | N64_I70delinsHLTAVGK |
| 4 | C194 | C194A/S/G | N/A (conserved residue) |
| 5 | C231 | C231A/S/G | N/A (conserved residue) |

FIG. 16A
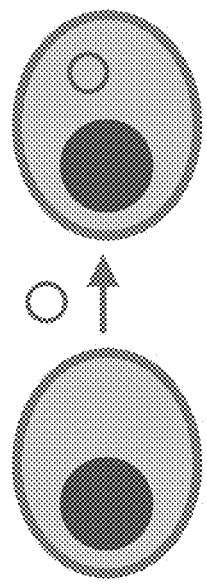
FIG. 16B
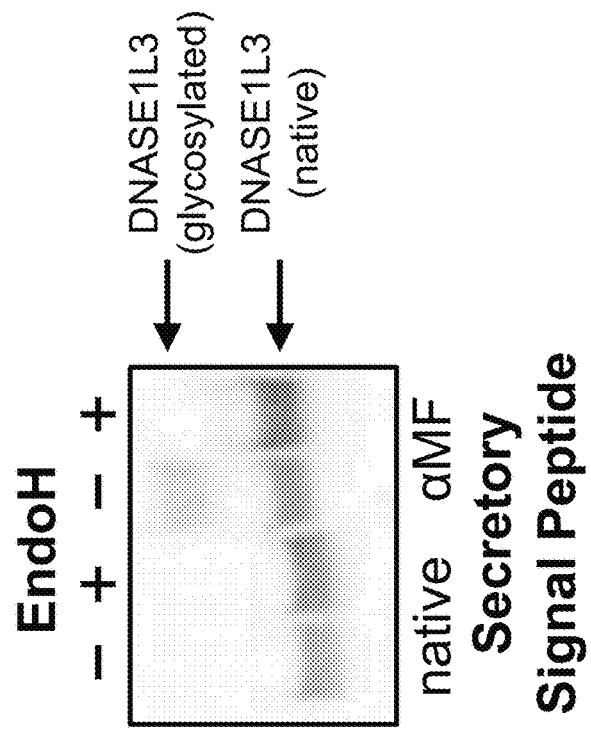
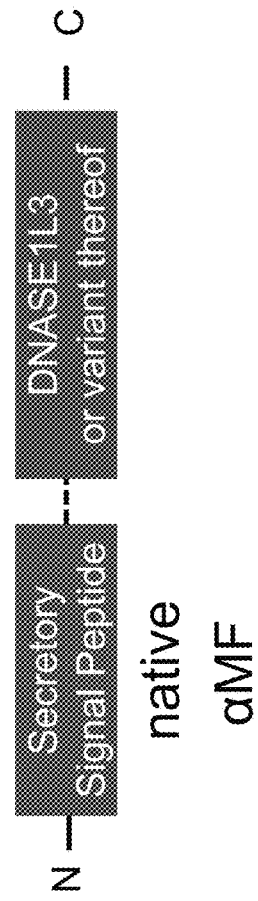

FIG. 17A
cGMP-Expression System: *Pichia pastoris*
Expression Vector:
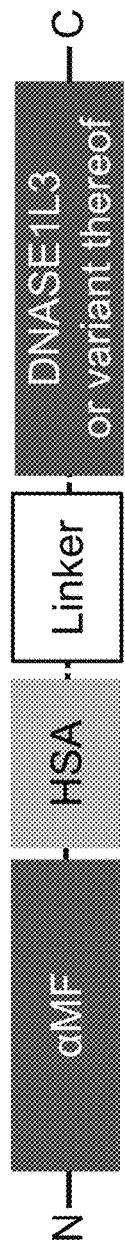
N — αMF — HSA — Linker — DNASE1L3 or variant thereof — C
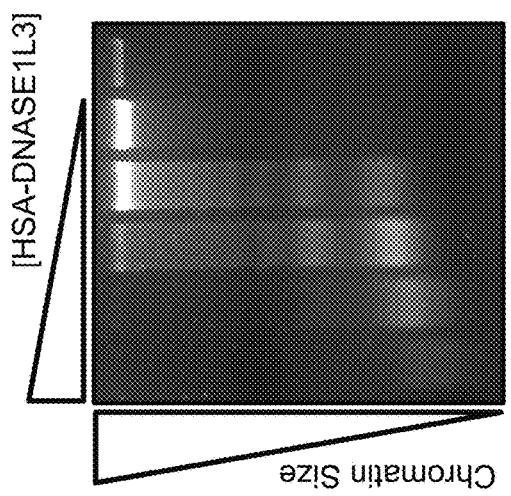
FIG. 17B
– EndoH
+ EndoH
mCE
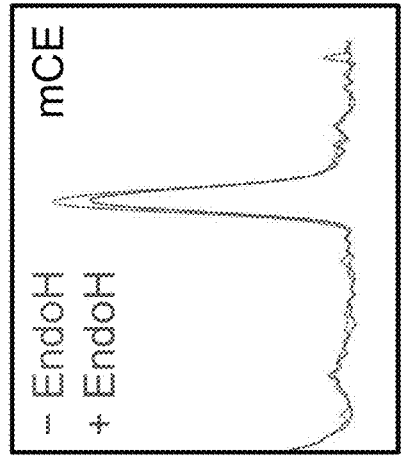
FIG. 17C
[HSA-DNASE1L3]
Chromatin Size

FIG. 18

| | | Expression Vector | | | Expression Level (rel. Units) |
|---|---|---|---|---|---|
| SEQ ID NO: 14 | | BDD-D1L3 | | | 4.3±0.5 |
| SEQ ID NO: 17 | HSA | - | BDD-D1L3 | | 4.3±0.4 |
| SEQ ID NO: 18 | HSA | L1 | BDD-D1L3 | | 12±1.9 |
| SEQ ID NO: 19 | HSA | L2 | BDD-D1L3 | | 32±3.2 |
| SEQ ID NO: 20 | | | BDD-D1L3 | L1 HSA | <1 |
| SEQ ID NO: 21 | | | BDD-D1L3 | L2 HSA | 1.8±0.2 |
| SEQ ID NO: 4 | | | D1L3 | | 1.1±0.1 |
| SEQ ID NO: 22 | HSA | L2 | D1L3 | | 22±1.3 |

| Linker | Sequence | Length |
|---|---|---|
| SEQ ID NO: 31 | L1 | GGGGS | 5 AA |
| SEQ ID NO: 32 | L2 | (GGGGS)$_3$ | 15 AA |

FIG. 19

| | Expression Vector | | Expression Level (rel. Units) |
|---|---|---|---|
| SEQ ID NO: 22 | HSA | L2 | D1L3 | 17±5.5 |
| SEQ ID NO: 23 | HSA | L3 | D1L3 | 22±6.9 |
| SEQ ID NO: 24 | HSA | L4 | D1L3 | 11±4.9 |

| | Linker | Sequence | Length | Property |
|---|---|---|---|---|
| SEQ ID NO: 32 | L2 | (GGGGS)$_3$ | 15 | flexible |
| SEQ ID NO: 33 | L3 | (AP)$_7$ | 14 | rigid |
| SEQ ID NO: 34 | L4 | A(EAAAK)$_2$A | 12 | rigid |

FIG. 22

| | | Expression Vector | | | Expression Level (rel. Units) |
|---|---|---|---|---|---|
| SEQ ID NO: 27 | HSA | L7 | BDD-D1L3 | | 32±5.9 |
| SEQ ID NO: 28 | HSA | L7 | BDD-D1L3 | L8 HSA | 30±8.3 |

| Linker | Sequence | Length |
|---|---|---|
| SEQ ID NO: 37 L7 | S(GGS)₉GSS | 31 |
| SEQ ID NO: 38 L8 | (GGS)₉GS | 29 |

Expression Vector:

Factor XIIa Cleavable Linker:

SEQUENCE LISTING

<160> NUMBER OF SEQ ID NOS: 48

<210> SEQ ID NO 1
<211> LENGTH: 282
<212> TYPE: PRT
<213> ORGANISM: Homo sapiens

<400> SEQUENCE: 1

Met Arg Gly Met Lys Leu Leu Gly Ala Leu Leu Ala Leu Ala Ala Leu
1               5                   10                  15

Leu Gln Gly Ala Val Ser Leu Lys Ile Ala Ala Phe Asn Ile Gln Thr
            20                  25                  30

```
Phe Gly Glu Thr Lys Met Ser Asn Ala Thr Leu Val Ser Tyr Ile Val
             35                  40                  45

Gln Ile Leu Ser Arg Tyr Asp Ile Ala Leu Val Gln Glu Val Arg Asp
 50                  55                  60

Ser His Leu Thr Ala Val Gly Lys Leu Leu Asp Asn Leu Asn Gln Asp
 65                  70                  75                  80

Ala Pro Asp Thr Tyr His Tyr Val Val Ser Glu Pro Leu Gly Arg Asn
                 85                  90                  95

Ser Tyr Lys Glu Arg Tyr Leu Phe Val Tyr Arg Pro Asp Gln Val Ser
            100                 105                 110

Ala Val Asp Ser Tyr Tyr Tyr Asp Asp Gly Cys Glu Pro Cys Gly Asn
            115                 120                 125

Asp Thr Phe Asn Arg Glu Pro Ala Ile Val Arg Phe Phe Ser Arg Phe
130                 135                 140

Thr Glu Val Arg Glu Phe Ala Ile Val Pro Leu His Ala Ala Pro Gly
145                 150                 155                 160

Asp Ala Val Ala Glu Ile Asp Ala Leu Tyr Asp Val Tyr Leu Asp Val
                165                 170                 175

Gln Glu Lys Trp Gly Leu Glu Asp Val Met Leu Met Gly Asp Phe Asn
            180                 185                 190

Ala Gly Cys Ser Tyr Val Arg Pro Ser Gln Trp Ser Ser Ile Arg Leu
            195                 200                 205

Trp Thr Ser Pro Thr Phe Gln Trp Leu Ile Pro Asp Ser Ala Asp Thr
210                 215                 220

Thr Ala Thr Pro Thr His Cys Ala Tyr Asp Arg Ile Val Val Ala Gly
225                 230                 235                 240

Met Leu Leu Arg Gly Ala Val Val Pro Asp Ser Ala Leu Pro Phe Asn
                245                 250                 255

Phe Gln Ala Ala Tyr Gly Leu Ser Asp Gln Leu Ala Gln Ala Ile Ser
            260                 265                 270

Asp His Tyr Pro Val Glu Val Met Leu Lys
            275                 280

<210> SEQ ID NO 2
<211> LENGTH: 302
<212> TYPE: PRT
<213> ORGANISM: Homo sapiens

<400> SEQUENCE: 2

Met His Tyr Pro Thr Ala Leu Leu Phe Leu Ile Leu Ala Asn Gly Ala
 1               5                  10                  15

Gln Ala Phe Arg Ile Cys Ala Phe Asn Ala Gln Arg Leu Thr Leu Ala
             20                  25                  30

Lys Val Ala Arg Glu Gln Val Met Asp Thr Leu Val Arg Ile Leu Ala
             35                  40                  45

Arg Cys Asp Ile Met Val Leu Gln Glu Val Val Asp Ser Ser Gly Ser
 50                  55                  60

Ala Ile Pro Leu Leu Leu Arg Glu Leu Asn Arg Phe Asp Gly Ser Gly
 65                  70                  75                  80

Pro Tyr Ser Thr Leu Ser Ser Pro Gln Leu Gly Arg Ser Thr Tyr Met
                 85                  90                  95

Glu Thr Tyr Val Tyr Phe Tyr Arg Ser His Lys Thr Gln Val Leu Ser
            100                 105                 110

Ser Tyr Val Tyr Asn Asp Glu Asp Asp Val Phe Ala Arg Glu Pro Phe
            115                 120                 125
```

Val Ala Gln Phe Ser Leu Pro Ser Asn Val Leu Pro Ser Leu Val Leu
    130                 135                 140

Val Pro Leu His Thr Thr Pro Lys Ala Val Glu Lys Glu Leu Asn Ala
145                 150                 155                 160

Leu Tyr Asp Val Phe Leu Glu Val Ser Gln His Trp Gln Ser Lys Asp
                165                 170                 175

Val Ile Leu Leu Gly Asp Phe Asn Ala Asp Cys Ala Ser Leu Thr Lys
                180                 185                 190

Lys Arg Leu Asp Lys Leu Glu Leu Arg Thr Glu Pro Gly Phe His Trp
            195                 200                 205

Val Ile Ala Asp Gly Glu Asp Thr Thr Val Arg Ala Ser Thr His Cys
    210                 215                 220

Thr Tyr Asp Arg Val Val Leu His Gly Glu Arg Cys Arg Ser Leu Leu
225                 230                 235                 240

His Thr Ala Ala Ala Phe Asp Phe Pro Thr Ser Phe Gln Leu Thr Glu
                245                 250                 255

Glu Glu Ala Leu Asn Ile Ser Asp His Tyr Pro Val Glu Val Glu Leu
            260                 265                 270

Lys Leu Ser Gln Ala His Ser Val Gln Pro Leu Ser Leu Thr Val Leu
    275                 280                 285

Leu Leu Leu Ser Leu Leu Ser Pro Gln Leu Cys Pro Ala Ala
290                 295                 300

<210> SEQ ID NO 3
<211> LENGTH: 299
<212> TYPE: PRT
<213> ORGANISM: Homo sapiens

<400> SEQUENCE: 3

Met Gly Gly Pro Arg Ala Leu Leu Ala Leu Trp Ala Leu Glu Ala
1               5                   10                  15

Ala Gly Thr Ala Ala Leu Arg Ile Gly Ala Phe Asn Ile Gln Ser Phe
                20                  25                  30

Gly Asp Ser Lys Val Ser Asp Pro Ala Cys Gly Ser Ile Ile Ala Lys
            35                  40                  45

Ile Leu Ala Gly Tyr Asp Leu Ala Leu Val Gln Glu Val Arg Asp Pro
    50                  55                  60

Asp Leu Ser Ala Val Ser Ala Leu Met Glu Gln Ile Asn Ser Val Ser
65                  70                  75                  80

Glu His Glu Tyr Ser Phe Val Ser Ser Gln Pro Leu Gly Arg Asp Gln
                85                  90                  95

Tyr Lys Glu Met Tyr Leu Phe Val Tyr Arg Lys Asp Ala Val Ser Val
            100                 105                 110

Val Asp Thr Tyr Leu Tyr Pro Asp Pro Glu Asp Val Phe Ser Arg Glu
    115                 120                 125

Pro Phe Val Val Lys Phe Ser Ala Pro Gly Thr Gly Glu Arg Ala Pro
130                 135                 140

Pro Leu Pro Ser Arg Arg Ala Leu Thr Pro Pro Leu Pro Ala Ala
145                 150                 155                 160

Ala Gln Asn Leu Val Leu Ile Pro Leu His Ala Pro His Gln Ala
                165                 170                 175

Val Ala Glu Ile Asp Ala Leu Tyr Asp Val Tyr Leu Asp Val Ile Asp
            180                 185                 190

Lys Trp Gly Thr Asp Asp Met Leu Phe Leu Gly Asp Phe Asn Ala Asp

```
                  195                 200                 205
Cys Ser Tyr Val Arg Ala Gln Asp Trp Ala Ala Ile Arg Leu Arg Ser
210                 215                 220

Ser Glu Val Phe Lys Trp Leu Ile Pro Asp Ser Ala Asp Thr Thr Val
225                 230                 235                 240

Gly Asn Ser Asp Cys Ala Tyr Asp Arg Ile Val Ala Cys Gly Ala Arg
                245                 250                 255

Leu Arg Arg Ser Leu Lys Pro Gln Ser Ala Thr Val His Asp Phe Gln
            260                 265                 270

Glu Glu Phe Gly Leu Asp Gln Thr Gln Ala Leu Ala Ile Ser Asp His
        275                 280                 285

Phe Pro Val Glu Val Thr Leu Lys Phe His Arg
    290                 295

<210> SEQ ID NO 4
<211> LENGTH: 305
<212> TYPE: PRT
<213> ORGANISM: Homo sapiens

<400> SEQUENCE: 4

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270
```

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
290                 295                 300

Ser
305

<210> SEQ ID NO 5
<211> LENGTH: 275
<212> TYPE: PRT
<213> ORGANISM: Homo sapiens

<400> SEQUENCE: 5

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Glu Lys Leu
65                  70                  75                  80

Val Ser Val Lys Arg Ser Tyr His Tyr His Asp Tyr Gln Asp Gly Asp
                85                  90                  95

Ala Asp Val Phe Ser Arg Glu Pro Phe Val Val Trp Phe Gln Ser Pro
            100                 105                 110

His Thr Ala Val Lys Asp Phe Val Ile Ile Pro Leu His Thr Thr Pro
        115                 120                 125

Glu Thr Ser Val Lys Glu Ile Asp Glu Leu Val Glu Val Tyr Thr Asp
    130                 135                 140

Val Lys His Arg Trp Lys Ala Glu Asn Phe Ile Phe Met Gly Asp Phe
145                 150                 155                 160

Asn Ala Gly Cys Ser Tyr Val Pro Lys Lys Ala Trp Lys Asn Ile Arg
                165                 170                 175

Leu Arg Thr Asp Pro Arg Phe Val Trp Leu Ile Gly Asp Gln Glu Asp
            180                 185                 190

Thr Thr Val Lys Lys Ser Thr Asn Cys Ala Tyr Asp Arg Ile Val Leu
        195                 200                 205

Arg Gly Gln Glu Ile Val Ser Ser Val Val Pro Lys Ser Asn Ser Val
    210                 215                 220

Phe Asp Phe Gln Lys Ala Tyr Lys Leu Thr Glu Glu Glu Ala Leu Asp
225                 230                 235                 240

Val Ser Asp His Phe Pro Val Glu Phe Lys Leu Gln Ser Ser Arg Ala
                245                 250                 255

Phe Thr Asn Ser Lys Lys Ser Val Thr Leu Arg Lys Lys Thr Lys Ser
            260                 265                 270

Lys Arg Ser
275

<210> SEQ ID NO 6
<211> LENGTH: 360
<212> TYPE: PRT
<213> ORGANISM: Homo sapiens

<400> SEQUENCE: 6

```
Met Ile Pro Leu Leu Leu Ala Ala Leu Leu Cys Val Pro Ala Gly Ala
1               5                   10                  15

Leu Thr Cys Tyr Gly Asp Ser Gly Gln Pro Val Asp Trp Phe Val Val
            20                  25                  30

Tyr Lys Leu Pro Ala Leu Arg Gly Ser Gly Glu Ala Ala Gln Arg Gly
                35                  40                  45

Leu Gln Tyr Lys Tyr Leu Asp Glu Ser Ser Gly Gly Trp Arg Asp Gly
50                  55                  60

Arg Ala Leu Ile Asn Ser Pro Glu Gly Ala Val Gly Arg Ser Leu Gln
65                  70                  75                  80

Pro Leu Tyr Arg Ser Asn Thr Ser Gln Leu Ala Phe Leu Leu Tyr Asn
                85                  90                  95

Asp Gln Pro Pro Gln Pro Ser Lys Ala Gln Asp Ser Ser Met Arg Gly
                100                 105                 110

His Thr Lys Gly Val Leu Leu Asp His Asp Gly Phe Trp Leu
                115                 120                 125

Val His Ser Val Pro Asn Phe Pro Pro Ala Ser Ala Ala Tyr
        130                 135                 140

Ser Trp Pro His Ser Ala Cys Thr Tyr Gly Gln Thr Leu Leu Cys Val
145                 150                 155                 160

Ser Phe Pro Phe Ala Gln Phe Ser Lys Met Gly Lys Gln Leu Thr Tyr
                165                 170                 175

Thr Tyr Pro Trp Val Tyr Asn Tyr Gln Leu Glu Gly Ile Phe Ala Gln
                180                 185                 190

Glu Phe Pro Asp Leu Glu Asn Val Val Lys Gly His His Val Ser Gln
                195                 200                 205

Glu Pro Trp Asn Ser Ser Ile Thr Leu Thr Ser Gln Ala Gly Ala Val
        210                 215                 220

Phe Gln Ser Phe Ala Lys Phe Ser Lys Phe Gly Asp Asp Leu Tyr Ser
225                 230                 235                 240

Gly Trp Leu Ala Ala Leu Gly Thr Asn Leu Gln Val Gln Phe Trp
                245                 250                 255

His Lys Thr Val Gly Ile Leu Pro Ser Asn Cys Ser Asp Ile Trp Gln
                260                 265                 270

Val Leu Asn Val Asn Gln Ile Ala Phe Pro Gly Pro Ala Gly Pro Ser
        275                 280                 285

Phe Asn Ser Thr Glu Asp His Ser Lys Trp Cys Val Ser Pro Lys Gly
        290                 295                 300

Pro Trp Thr Cys Val Gly Asp Met Asn Arg Asn Gln Gly Glu Glu Gln
305                 310                 315                 320

Arg Gly Gly Gly Thr Leu Cys Ala Gln Leu Pro Ala Leu Trp Lys Ala
                325                 330                 335

Phe Gln Pro Leu Val Lys Asn Tyr Gln Pro Cys Asn Gly Met Ala Arg
                340                 345                 350

Lys Pro Ser Arg Ala Tyr Lys Ile
                355                 360

<210> SEQ ID NO 7
<211> LENGTH: 361
<212> TYPE: PRT
<213> ORGANISM: Homo sapiens

<400> SEQUENCE: 7

Met Lys Gln Lys Met Met Ala Arg Leu Leu Arg Thr Ser Phe Ala Leu
1               5                   10                  15
```

```
Leu Phe Leu Gly Leu Phe Gly Val Leu Gly Ala Ala Thr Ile Ser Cys
        20                  25                  30

Arg Asn Glu Glu Gly Lys Ala Val Asp Trp Phe Thr Phe Tyr Lys Leu
            35                  40                  45

Pro Lys Arg Gln Asn Lys Glu Ser Gly Glu Thr Gly Leu Glu Tyr Leu
    50                  55                  60

Tyr Leu Asp Ser Thr Thr Arg Ser Trp Arg Lys Ser Glu Gln Leu Met
65                  70                  75                  80

Asn Asp Thr Lys Ser Val Leu Gly Arg Thr Leu Gln Gln Leu Tyr Glu
                85                  90                  95

Ala Tyr Ala Ser Lys Ser Asn Asn Thr Ala Tyr Leu Ile Tyr Asn Asp
            100                 105                 110

Gly Val Pro Lys Pro Val Asn Tyr Ser Arg Lys Tyr Gly His Thr Lys
        115                 120                 125

Gly Leu Leu Leu Trp Asn Arg Val Gln Gly Phe Trp Leu Ile His Ser
    130                 135                 140

Ile Pro Gln Phe Pro Pro Ile Pro Glu Glu Gly Tyr Asp Tyr Pro Pro
145                 150                 155                 160

Thr Gly Arg Arg Asn Gly Gln Ser Gly Ile Cys Ile Thr Phe Lys Tyr
                165                 170                 175

Asn Gln Tyr Glu Ala Ile Asp Ser Gln Leu Leu Val Cys Asn Pro Asn
            180                 185                 190

Val Tyr Ser Cys Ser Ile Pro Ala Thr Phe His Gln Glu Leu Ile His
        195                 200                 205

Met Pro Gln Leu Cys Thr Arg Ala Ser Ser Glu Ile Pro Gly Arg
    210                 215                 220

Leu Leu Thr Thr Leu Gln Ser Ala Gln Gly Gln Lys Phe Leu His Phe
225                 230                 235                 240

Ala Lys Ser Asp Ser Phe Leu Asp Asp Ile Phe Ala Ala Trp Met Ala
                245                 250                 255

Gln Arg Leu Lys Thr His Leu Leu Thr Glu Thr Trp Gln Arg Lys Arg
            260                 265                 270

Gln Glu Leu Pro Ser Asn Cys Ser Leu Pro Tyr His Val Tyr Asn Ile
        275                 280                 285

Lys Ala Ile Lys Leu Ser Arg His Ser Tyr Phe Ser Ser Tyr Gln Asp
    290                 295                 300

His Ala Lys Trp Cys Ile Ser Gln Lys Gly Thr Lys Asn Arg Trp Thr
305                 310                 315                 320

Cys Ile Gly Asp Leu Asn Arg Ser Pro His Gln Ala Phe Arg Ser Gly
                325                 330                 335

Gly Phe Ile Cys Thr Gln Asn Trp Gln Ile Tyr Gln Ala Phe Gln Gly
            340                 345                 350

Leu Val Leu Tyr Tyr Glu Ser Cys Lys
        355                 360

<210> SEQ ID NO 8
<211> LENGTH: 305
<212> TYPE: PRT
<213> ORGANISM: Homo sapiens

<400> SEQUENCE: 8

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
```

```
            20                  25                  30
Glu Ser Lys Gln Glu Asp Lys Asn Ala Met Asp Val Ile Val Lys Val
         35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Asn Ser Arg
 65                  70                  75                  80

Arg Gly Ile Thr Tyr Asn Tyr Val Ile Ser Ser Arg Leu Gly Arg Asn
                 85                  90                  95

Thr Tyr Lys Glu Arg Tyr Ala Phe Leu Tyr Glu Lys Leu Val Ser
            100                 105                 110

Val Lys Arg Ser Tyr His Tyr His Asp Tyr Gln Asp Gly Asp Ala Asp
            115                 120                 125

Val Phe Ser Arg Glu Pro Phe Val Val Trp Phe Gln Ser Pro His Thr
            130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
            195                 200                 205

Thr Asp Pro Arg Phe Val Trp Leu Ile Gly Asp Gln Glu Asp Thr Thr
            210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
            275                 280                 285

Asn Ser Lys Lys Ser Val Thr Leu Arg Lys Lys Thr Lys Ser Lys Arg
            290                 295                 300

Ser
305

<210> SEQ ID NO 9
<211> LENGTH: 282
<212> TYPE: PRT
<213> ORGANISM: Homo sapiens

<400> SEQUENCE: 9

Met Ser Arg Glu Leu Ala Pro Leu Leu Leu Leu Leu Leu Ser Ile His
1               5                  10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
         35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Asn Ser Arg
 65                  70                  75                  80
```

-continued

```
Arg Gly Ile Thr Tyr Asn Tyr Val Ile Ser Ser Arg Leu Gly Arg Asn
                 85                  90                  95
Thr Tyr Lys Glu Gln Tyr Ala Phe Leu Tyr Lys Glu Lys Leu Val Ser
            100                 105                 110
Val Lys Arg Ser Tyr His Tyr His Asp Tyr Gln Asp Gly Asp Ala Asp
        115                 120                 125
Val Phe Ser Arg Glu Pro Phe Val Trp Phe Gln Ser Pro His Thr
    130                 135                 140
Ala Val Lys Asp Phe Val Ile Ile Pro Leu His Thr Thr Pro Glu Thr
145                 150                 155                 160
Ser Val Lys Glu Ile Asp Glu Leu Val Glu Val Tyr Thr Asp Val Lys
                165                 170                 175
His Arg Trp Lys Ala Glu Asn Phe Ile Phe Met Gly Asp Phe Asn Ala
            180                 185                 190
Gly Cys Ser Tyr Val Pro Lys Lys Ala Trp Lys Asn Ile Arg Leu Arg
        195                 200                 205
Thr Asp Pro Arg Phe Val Trp Leu Ile Gly Asp Gln Glu Asp Thr Thr
    210                 215                 220
Val Lys Lys Ser Thr Asn Cys Ala Tyr Asp Arg Ile Val Leu Arg Gly
225                 230                 235                 240
Gln Glu Ile Val Ser Ser Val Pro Lys Ser Asn Ser Val Phe Asp
                245                 250                 255
Phe Gln Lys Ala Tyr Lys Leu Thr Glu Glu Ala Leu Asp Val Ser
            260                 265                 270
Asp His Phe Pro Val Glu Phe Lys Leu Lys
        275                 280
```

```
<210> SEQ ID NO 10
<211> LENGTH: 290
<212> TYPE: PRT
<213> ORGANISM: Homo sapiens

<400> SEQUENCE: 10

Met Ser Arg Glu Leu Ala Pro Leu Leu Leu Leu Leu Ser Ile His
1               5                   10                  15
Ser Ala Leu Ala Met Arg Ile Cys Ser Phe Asn Val Arg Ser Phe Gly
                20                  25                  30
Glu Ser Lys Gln Glu Asp Lys Asn Ala Met Asp Val Ile Val Lys Val
            35                  40                  45
Ile Lys Arg Cys Asp Ile Ile Leu Val Met Glu Ile Lys Asp Ser Asn
        50                  55                  60
Asn Arg Ile Cys Pro Ile Leu Met Glu Lys Leu Asn Arg Asn Ser Arg
65                  70                  75                  80
Arg Gly Ile Thr Tyr Asn Tyr Val Ile Ser Ser Arg Leu Gly Arg Asn
                 85                  90                  95
Thr Tyr Lys Glu Gln Tyr Ala Phe Leu Tyr Lys Glu Lys Leu Val Ser
            100                 105                 110
Val Lys Arg Ser Tyr His Tyr His Asp Tyr Gln Asp Gly Asp Ala Asp
        115                 120                 125
Val Phe Ser Arg Glu Pro Phe Val Trp Phe Gln Ser Pro His Thr
    130                 135                 140
Ala Val Lys Asp Phe Val Ile Ile Pro Leu His Thr Thr Pro Glu Thr
145                 150                 155                 160
Ser Val Lys Glu Ile Asp Glu Leu Val Glu Val Tyr Thr Asp Val Lys
                165                 170                 175
```

His Arg Trp Gly Leu Glu Asn Phe Ile Phe Met Gly Asp Phe Asn Ala
            180                 185                 190

Gly Cys Ser Tyr Val Arg Pro Ser Gln Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Ala Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
    275                 280                 285

Asn Ser
    290

<210> SEQ ID NO 11
<211> LENGTH: 291
<212> TYPE: PRT
<213> ORGANISM: Homo sapiens

<400> SEQUENCE: 11

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Gly Leu Glu Asn Phe Ile Phe Met Gly Asp Phe Asn Ala
            180                 185                 190

Gly Cys Ser Tyr Val Arg Pro Ser Gln Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp

```
                      245                 250                 255
Phe Gln Ala Ala Tyr Lys Leu Thr Glu Glu Ala Leu Asp Val Ser
                260                 265                 270

Asp His Phe Pro Val Glu Phe Lys Leu Gln Ser Ser Arg Ala Phe Thr
            275                 280                 285

Asn Ser Lys
        290

<210> SEQ ID NO 12
<211> LENGTH: 292
<212> TYPE: PRT
<213> ORGANISM: Homo sapiens

<400> SEQUENCE: 12

Met Ser Arg Glu Leu Ala Pro Leu Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Cys Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
    130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Gly Leu Glu Asn Phe Ile Phe Met Gly Asp Phe Asn Ala
            180                 185                 190

Gly Cys Ser Tyr Val Arg Pro Ser Gln Trp Lys Asn Ile Arg Leu Arg
        195                 200                 205

Thr Asp Pro Arg Phe Val Trp Leu Ile Gly Asp Gln Glu Asp Thr Thr
    210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Ala Ala Tyr Lys Leu Thr Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys
    290

<210> SEQ ID NO 13
<211> LENGTH: 305
```

<212> TYPE: PRT
<213> ORGANISM: Homo sapiens

<400> SEQUENCE: 13

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

Glu Ser Lys Gln Glu Asp Lys Asn Ala Met Asp Val Ile Val Lys Val
        35                  40                  45

Ile Lys Arg Cys Asp Ile Ile Leu Val Met Glu Ile Lys Asp Ser Asn
    50                  55                  60

Asn Arg Ile Ala Pro Ile Leu Met Glu Lys Leu Asn Arg Asn Ser Arg
65                  70                  75                  80

Arg Gly Ile Thr Tyr Asn Tyr Val Ile Ser Ser Arg Leu Gly Arg Asn
                85                  90                  95

Thr Tyr Lys Glu Gln Tyr Ala Phe Leu Tyr Lys Glu Lys Leu Val Ser
            100                 105                 110

Val Lys Arg Ser Tyr His Tyr His Asp Tyr Gln Asp Gly Asp Ala Asp
        115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Glu Ala Leu Asp Val Ser
            260                 265                 270

Asp His Phe Pro Val Glu Phe Lys Leu Gln Ser Ser Arg Ala Phe Thr
        275                 280                 285

Asn Ser Lys Lys Ser Val Thr Leu Arg Lys Lys Thr Lys Ser Lys Arg
290                 295                 300

Ser
305

<210> SEQ ID NO 14
<211> LENGTH: 282
<212> TYPE: PRT
<213> ORGANISM: Homo sapiens

<400> SEQUENCE: 14

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
            20                  25                  30

```
Glu Ser Lys Gln Glu Asp Lys Asn Ala Met Asp Val Ile Val Lys Val
         35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Asn Ser Arg
 65                  70                  75                  80

Arg Gly Ile Thr Tyr Asn Tyr Val Ile Ser Ser Arg Leu Gly Arg Asn
                 85                  90                  95

Thr Tyr Lys Glu Gln Tyr Ala Phe Leu Tyr Lys Glu Lys Leu Val Ser
             100                 105                 110

Val Lys Arg Ser Tyr His Tyr His Asp Tyr Gln Asp Gly Asp Ala Asp
         115                 120                 125

Val Phe Ser Arg Glu Pro Phe Val Val Trp Phe Gln Ser Pro His Thr
130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
            180                 185                 190

Gly Cys Ser Tyr Val Pro Lys Lys Ala Trp Lys Asn Ile Arg Leu Arg
        195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
            260                 265                 270

Asp His Tyr Pro Val Glu Val Met Leu Lys
        275                 280

<210> SEQ ID NO 15
<211> LENGTH: 282
<212> TYPE: PRT
<213> ORGANISM: Homo sapiens

<400> SEQUENCE: 15

Met Ser Arg Glu Leu Ala Pro Leu Leu Leu Leu Leu Ser Ile His
 1               5                  10                  15

Ser Ala Leu Ala Met Arg Ile Cys Ser Phe Asn Val Arg Ser Phe Gly
             20                  25                  30

Glu Ser Lys Gln Glu Asp Lys Asn Ala Met Asp Val Ile Val Lys Val
         35                  40                  45

Ile Lys Arg Cys Asp Ile Ile Leu Val Met Glu Ile Lys Asp Ser Asn
 50                  55                  60

Asn Arg Ile Cys Pro Ile Leu Met Glu Lys Leu Asn Arg Asn Ser Arg
 65                  70                  75                  80

Arg Gly Ile Thr Tyr Asn Tyr Val Ile Ser Ser Arg Leu Gly Arg Asn
                 85                  90                  95

Thr Tyr Lys Glu Gln Tyr Ala Phe Leu Tyr Lys Glu Lys Leu Val Ser
             100                 105                 110

Val Lys Arg Ser Tyr His Tyr His Asp Tyr Gln Asp Gly Asp Ala Asp
         115                 120                 125
```

```
Val Phe Ser Arg Glu Pro Phe Val Trp Phe Gln Ser Pro His Thr
        130                 135                 140

Ala Val Lys Asp Phe Val Ile Ile Pro Leu His Thr Thr Pro Glu Thr
145                 150                 155                 160

Ser Val Lys Glu Ile Asp Glu Leu Val Glu Val Tyr Thr Asp Val Lys
                165                 170                 175

His Arg Trp Lys Ala Glu Asn Phe Ile Phe Met Gly Asp Phe Asn Ala
                180                 185                 190

Gly Cys Ser Tyr Val Pro Lys Lys Ala Trp Lys Asn Ile Arg Leu Arg
                195                 200                 205

Thr Asp Pro Arg Phe Val Trp Leu Ile Gly Asp Gln Glu Asp Thr Thr
210                 215                 220

Val Lys Lys Ser Thr Asn Cys Ala Tyr Asp Arg Ile Val Leu Arg Gly
225                 230                 235                 240

Gln Glu Ile Val Ser Ser Val Val Pro Lys Ser Asn Ser Val Phe Asp
                245                 250                 255

Phe Gln Lys Ala Tyr Lys Leu Thr Glu Glu Ala Leu Asp Val Ser
                260                 265                 270

Asp His Phe Pro Val Glu Phe Lys Leu Gln
                275                 280

<210> SEQ ID NO 16
<211> LENGTH: 254
<212> TYPE: PRT
<213> ORGANISM: Homo sapiens

<400> SEQUENCE: 16

Met Ser Arg Glu Leu Ala Pro Leu Leu Leu Leu Leu Ser Ile His
1               5                   10                  15

Ser Ala Leu Ala Met Arg Ile Cys Ser Phe Asn Val Arg Ser Phe Gly
                20                  25                  30

Glu Ser Lys Gln Glu Asp Lys Asn Ala Met Asp Val Ile Val Lys Val
            35                  40                  45

Ile Lys Arg Cys Asp Ile Ile Leu Val Met Glu Ile Lys Asp Ser Asn
50                  55                  60

Asn Arg Ile Cys Pro Ile Leu Met Glu Lys Leu Asn Arg Glu Lys Leu
65                  70                  75                  80

Val Ser Val Lys Arg Ser Tyr His Tyr His Asp Tyr Gln Asp Gly Asp
                85                  90                  95

Ala Asp Val Phe Ser Arg Glu Pro Phe Val Val Trp Phe Gln Ser Pro
                100                 105                 110

His Thr Ala Val Lys Asp Phe Val Ile Ile Pro Leu His Thr Thr Pro
            115                 120                 125

Glu Thr Ser Val Lys Glu Ile Asp Glu Leu Val Glu Val Tyr Thr Asp
        130                 135                 140

Val Lys His Arg Trp Lys Ala Glu Asn Phe Ile Phe Met Gly Asp Phe
145                 150                 155                 160

Asn Ala Gly Cys Ser Tyr Val Pro Lys Lys Ala Trp Lys Asn Ile Arg
                165                 170                 175

Leu Arg Thr Asp Pro Arg Phe Val Trp Leu Ile Gly Asp Gln Glu Asp
                180                 185                 190

Thr Thr Val Lys Lys Ser Thr Asn Cys Ala Tyr Asp Arg Ile Val Leu
                195                 200                 205

Arg Gly Gln Glu Ile Val Ser Ser Val Val Pro Lys Ser Asn Ser Val
```

```
            210                 215                 220

Phe Asp Phe Gln Lys Ala Tyr Lys Leu Thr Glu Glu Ala Leu Asp
225                 230                 235                 240

Val Ser Asp His Phe Pro Val Glu Phe Lys Leu Gln Ser Ser
                245                 250

<210> SEQ ID NO 17
<211> LENGTH: 847
<212> TYPE: PRT
<213> ORGANISM: Artificial Sequence
<220> FEATURE:
<223> OTHER INFORMATION: Synthetic Sequence

<400> SEQUENCE: 17

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
```

-continued

```
                325                 330                 335
Arg His Pro Asp Tyr Ser Val Val Leu Leu Arg Leu Ala Lys Thr
                340                 345                 350
Tyr Glu Thr Thr Leu Glu Lys Cys Cys Ala Ala Asp Pro His Glu
                355                 360                 365
Cys Tyr Ala Lys Val Phe Asp Glu Phe Lys Pro Leu Val Glu Pro
                370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
Val Gly Ser Lys Cys Cys Lys His Pro Glu Ala Lys Arg Met Pro Cys
                435                 440                 445
Ala Glu Asp Tyr Leu Ser Val Val Leu Asn Gln Leu Cys Val Leu His
                450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
                515                 520                 525
Leu Val Glu Leu Val Lys His Lys Pro Lys Ala Thr Lys Glu Gln Leu
                530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Met Arg Ile Cys Ser Phe Asn
                580                 585                 590
Val Arg Ser Phe Gly Glu Ser Lys Gln Glu Asp Lys Asn Ala Met Asp
                595                 600                 605
Val Ile Val Lys Val Ile Lys Arg Cys Asp Ile Ile Leu Val Met Glu
                610                 615                 620
Ile Lys Asp Ser Asn Asn Arg Ile Cys Pro Ile Leu Met Glu Lys Leu
625                 630                 635                 640
Asn Arg Asn Ser Arg Arg Gly Ile Thr Tyr Asn Tyr Val Ile Ser Ser
                645                 650                 655
Arg Leu Gly Arg Asn Thr Tyr Lys Glu Gln Tyr Ala Phe Leu Tyr Lys
                660                 665                 670
Glu Lys Leu Val Ser Val Lys Arg Ser Tyr His Tyr His Asp Tyr Gln
                675                 680                 685
Asp Gly Asp Ala Asp Val Phe Ser Arg Glu Pro Phe Val Val Trp Phe
                690                 695                 700
Gln Ser Pro His Thr Ala Val Lys Asp Phe Val Ile Ile Pro Leu His
705                 710                 715                 720
Thr Thr Pro Glu Thr Ser Val Lys Glu Ile Asp Glu Leu Val Glu Val
                725                 730                 735
Tyr Thr Asp Val Lys His Arg Trp Lys Ala Glu Asn Phe Ile Phe Met
                740                 745                 750
```

```
Gly Asp Phe Asn Ala Gly Cys Ser Tyr Val Pro Lys Lys Ala Trp Lys
            755                 760                 765

Asn Ile Arg Leu Arg Thr Asp Pro Arg Phe Val Trp Leu Ile Gly Asp
    770                 775                 780

Gln Glu Asp Thr Thr Val Lys Lys Ser Thr Asn Cys Ala Tyr Asp Arg
785                 790                 795                 800

Ile Val Leu Arg Gly Gln Glu Ile Val Ser Ser Val Val Pro Lys Ser
                805                 810                 815

Asn Ser Val Phe Asp Phe Gln Lys Ala Tyr Lys Leu Thr Glu Glu Glu
                820                 825                 830

Ala Leu Asp Val Ser Asp His Tyr Pro Val Glu Val Met Leu Lys
                835                 840                 845
```

<210> SEQ ID NO 18
<211> LENGTH: 852
<212> TYPE: PRT
<213> ORGANISM: Artificial Sequence
<220> FEATURE:
<223> OTHER INFORMATION: Synthetic Sequence

<400> SEQUENCE: 18

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
    115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
    195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
        420                 425                 430
Val Gly Ser Lys Cys Cys Lys His Pro Glu Ala Lys Arg Met Pro Cys
    435                 440                 445
Ala Glu Asp Tyr Leu Ser Val Val Leu Asn Gln Leu Cys Val Leu His
    450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
        500                 505                 510
Ile Cys Thr Leu Ser Glu Lys Glu Arg Gln Ile Lys Lys Gln Thr Ala
    515                 520                 525
Leu Val Glu Leu Val Lys His Lys Pro Lys Ala Thr Lys Glu Gln Leu
    530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Gly Gly Gly Ser Met Arg
        580                 585                 590
Ile Cys Ser Phe Asn Val Arg Ser Phe Gly Glu Ser Lys Gln Glu Asp
    595                 600                 605
Lys Asn Ala Met Asp Val Val Lys Val Ile Lys Arg Cys Asp Ile
    610                 615                 620
Ile Leu Val Met Glu Ile Lys Asp Ser Asn Asn Arg Ile Cys Pro Ile
625                 630                 635                 640
Leu Met Glu Lys Leu Asn Arg Asn Ser Arg Arg Gly Ile Thr Tyr Asn
                645                 650                 655
Tyr Val Ile Ser Ser Arg Leu Gly Arg Asn Thr Tyr Lys Glu Gln Tyr
        660                 665                 670
Ala Phe Leu Tyr Lys Glu Lys Leu Val Ser Val Lys Arg Ser Tyr His
    675                 680                 685
```

```
Tyr His Asp Tyr Gln Asp Gly Asp Ala Asp Val Phe Ser Arg Glu Pro
    690             695                 700
Phe Val Val Trp Phe Gln Ser Pro His Thr Ala Val Lys Asp Phe Val
705                 710                 715                 720
Ile Ile Pro Leu His Thr Thr Pro Glu Thr Ser Val Lys Glu Ile Asp
                725                 730                 735
Glu Leu Val Glu Val Tyr Thr Asp Val Lys His Arg Trp Lys Ala Glu
            740                 745                 750
Asn Phe Ile Phe Met Gly Asp Phe Asn Ala Gly Cys Ser Tyr Val Pro
            755                 760                 765
Lys Lys Ala Trp Lys Asn Ile Arg Leu Arg Thr Asp Pro Arg Phe Val
770                 775                 780
Trp Leu Ile Gly Asp Gln Glu Asp Thr Thr Val Lys Lys Ser Thr Asn
785                 790                 795                 800
Cys Ala Tyr Asp Arg Ile Val Leu Arg Gly Gln Glu Ile Val Ser Ser
                805                 810                 815
Val Val Pro Lys Ser Asn Ser Val Phe Asp Phe Gln Lys Ala Tyr Lys
                820                 825                 830
Leu Thr Glu Glu Glu Ala Leu Asp Val Ser Asp His Tyr Pro Val Glu
            835                 840                 845
Val Met Leu Lys
        850

<210> SEQ ID NO 19
<211> LENGTH: 862
<212> TYPE: PRT
<213> ORGANISM: Artificial Sequence
<220> FEATURE:
<223> OTHER INFORMATION: Synthetic Sequence

<400> SEQUENCE: 19

Asp Ala His Lys Ser Glu Val Ala His Arg Phe Lys Asp Leu Gly Glu
1               5                   10                  15
Glu Asn Phe Lys Ala Leu Val Leu Ile Ala Phe Ala Gln Tyr Leu Gln
            20                  25                  30
Gln Cys Pro Phe Glu Asp His Val Lys Leu Val Asn Glu Val Thr Glu
        35                  40                  45
Phe Ala Lys Thr Cys Val Ala Asp Glu Ser Ala Glu Asn Cys Asp Lys
    50                  55                  60
Ser Leu His Thr Leu Phe Gly Asp Lys Leu Cys Thr Val Ala Thr Leu
65                  70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
```

-continued

```
Ser Ala Lys Gln Arg Leu Lys Cys Ala Ser Leu Gln Lys Phe Gly Glu
            195                 200                 205
Arg Ala Phe Lys Ala Trp Ala Val Ala Arg Leu Ser Gln Arg Phe Pro
        210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                    245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                    325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
        370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                    405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                    485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
        530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                    565                 570                 575
Ala Ala Ser Gln Ala Ala Leu Gly Leu Gly Gly Gly Ser Gly Gly
            580                 585                 590
Gly Gly Ser Gly Gly Gly Gly Ser Met Arg Ile Cys Ser Phe Asn Val
        595                 600                 605
Arg Ser Phe Gly Glu Ser Lys Gln Glu Asp Lys Asn Ala Met Asp Val
```

```
                  610                 615                 620
Ile Val Lys Val Ile Lys Arg Cys Asp Ile Ile Leu Val Met Glu Ile
625                 630                 635                 640

Lys Asp Ser Asn Asn Arg Ile Cys Pro Ile Leu Met Glu Lys Leu Asn
                    645                 650                 655

Arg Asn Ser Arg Arg Gly Ile Thr Tyr Asn Tyr Val Ile Ser Ser Arg
                660                 665                 670

Leu Gly Arg Asn Thr Tyr Lys Glu Gln Tyr Ala Phe Leu Tyr Lys Glu
                675                 680                 685

Lys Leu Val Ser Val Lys Arg Ser Tyr His Tyr His Asp Tyr Gln Asp
                690                 695                 700

Gly Asp Ala Asp Val Phe Ser Arg Glu Pro Phe Val Val Trp Phe Gln
705                 710                 715                 720

Ser Pro His Thr Ala Val Lys Asp Phe Val Ile Pro Leu His Thr
                725                 730                 735

Thr Pro Glu Thr Ser Val Lys Glu Ile Asp Glu Leu Val Glu Val Tyr
                740                 745                 750

Thr Asp Val Lys His Arg Trp Lys Ala Glu Asn Phe Ile Phe Met Gly
                755                 760                 765

Asp Phe Asn Ala Gly Cys Ser Tyr Val Pro Lys Lys Ala Trp Lys Asn
770                 775                 780

Ile Arg Leu Arg Thr Asp Pro Arg Phe Val Trp Leu Ile Gly Asp Gln
785                 790                 795                 800

Glu Asp Thr Thr Val Lys Lys Ser Thr Asn Cys Ala Tyr Asp Arg Ile
                805                 810                 815

Val Leu Arg Gly Gln Glu Ile Val Ser Val Val Pro Lys Ser Asn
                820                 825                 830

Ser Val Phe Asp Phe Gln Lys Ala Tyr Lys Leu Thr Glu Glu Ala
                835                 840                 845

Leu Asp Val Ser Asp His Tyr Pro Val Glu Val Met Leu Lys
                850                 855                 860

<210> SEQ ID NO 20
<211> LENGTH: 852
<212> TYPE: PRT
<213> ORGANISM: Artificial Sequence
<220> FEATURE:
<223> OTHER INFORMATION: Synthetic Sequence

<400> SEQUENCE: 20

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
                20                  25                  30

Asp Ile Ile Leu Val Met Glu Ile Lys Asp Ser Asn Asn Arg Ile Cys
            35                  40                  45

Pro Ile Leu Met Glu Lys Leu Asn Arg Asn Ser Arg Arg Gly Ile Thr
        50                  55                  60

Tyr Asn Tyr Val Ile Ser Ser Arg Leu Gly Arg Asn Thr Tyr Lys Glu
65                  70                  75                  80

Gln Tyr Ala Phe Leu Tyr Lys Glu Lys Leu Val Ser Val Lys Arg Ser
                85                  90                  95

Tyr His Tyr His Asp Tyr Gln Asp Gly Asp Ala Asp Val Phe Ser Arg
                100                 105                 110

Glu Pro Phe Val Val Trp Phe Gln Ser Pro His Thr Ala Val Lys Asp
```

```
            115                 120                 125
Phe Val Ile Ile Pro Leu His Thr Thr Pro Glu Thr Ser Val Lys Glu
            130                 135                 140
Ile Asp Glu Leu Val Glu Val Tyr Thr Asp Val Lys His Arg Trp Lys
145                 150                 155                 160
Ala Glu Asn Phe Ile Phe Met Gly Asp Phe Asn Ala Gly Cys Ser Tyr
                165                 170                 175
Val Pro Lys Lys Ala Trp Lys Asn Ile Arg Leu Arg Thr Asp Pro Arg
            180                 185                 190
Phe Val Trp Leu Ile Gly Asp Gln Glu Asp Thr Thr Val Lys Lys Ser
            195                 200                 205
Thr Asn Cys Ala Tyr Asp Arg Ile Val Leu Arg Gly Gln Glu Ile Val
210                 215                 220
Ser Ser Val Val Pro Lys Ser Asn Ser Val Phe Asp Phe Gln Lys Ala
225                 230                 235                 240
Tyr Lys Leu Thr Glu Glu Ala Leu Asp Val Ser Asp His Tyr Pro
                245                 250                 255
Val Glu Val Met Leu Lys Gly Gly Gly Ser Asp Ala His Lys Ser
                260                 265                 270
Glu Val Ala His Arg Phe Lys Asp Leu Gly Glu Asn Phe Lys Ala
            275                 280                 285
Leu Val Leu Ile Ala Phe Ala Gln Tyr Leu Gln Gln Cys Pro Phe Glu
290                 295                 300
Asp His Val Lys Leu Val Asn Glu Val Thr Glu Phe Ala Lys Thr Cys
305                 310                 315                 320
Val Ala Asp Glu Ser Ala Glu Asn Cys Asp Lys Ser Leu His Thr Leu
                325                 330                 335
Phe Gly Asp Lys Leu Cys Thr Val Ala Thr Leu Arg Glu Thr Tyr Gly
                340                 345                 350
Glu Met Ala Asp Cys Cys Ala Lys Gln Glu Pro Glu Arg Asn Glu Cys
                355                 360                 365
Phe Leu Gln His Lys Asp Asp Asn Pro Asn Leu Pro Arg Leu Val Arg
370                 375                 380
Pro Glu Val Asp Val Met Cys Thr Ala Phe His Asp Asn Glu Glu Thr
385                 390                 395                 400
Phe Leu Lys Lys Tyr Leu Tyr Glu Ile Ala Arg Arg His Pro Tyr Phe
                405                 410                 415
Tyr Ala Pro Glu Leu Leu Phe Phe Ala Lys Arg Tyr Lys Ala Ala Phe
                420                 425                 430
Thr Glu Cys Cys Gln Ala Ala Asp Lys Ala Ala Cys Leu Leu Pro Lys
            435                 440                 445
Leu Asp Glu Leu Arg Asp Glu Gly Lys Ala Ser Ser Ala Lys Gln Arg
            450                 455                 460
Leu Lys Cys Ala Ser Leu Gln Lys Phe Gly Glu Arg Ala Phe Lys Ala
465                 470                 475                 480
Trp Ala Val Ala Arg Leu Ser Gln Arg Phe Pro Lys Ala Glu Phe Ala
                485                 490                 495
Glu Val Ser Lys Leu Val Thr Asp Leu Thr Lys Val His Thr Glu Cys
                500                 505                 510
Cys His Gly Asp Leu Leu Glu Cys Ala Asp Asp Arg Ala Asp Leu Ala
            515                 520                 525
Lys Tyr Ile Cys Glu Asn Gln Asp Ser Ile Ser Ser Lys Leu Lys Glu
            530                 535                 540
```

```
Cys Cys Glu Lys Pro Leu Leu Glu Lys Ser His Cys Ile Ala Glu Val
545                 550                 555                 560

Glu Asn Asp Glu Met Pro Ala Asp Leu Pro Ser Leu Ala Ala Asp Phe
                565                 570                 575

Val Glu Ser Lys Asp Val Cys Lys Asn Tyr Ala Glu Ala Lys Asp Val
            580                 585                 590

Phe Leu Gly Met Phe Leu Tyr Glu Tyr Ala Arg Arg His Pro Asp Tyr
            595                 600             605

Ser Val Val Leu Leu Leu Arg Leu Ala Lys Thr Tyr Glu Thr Thr Leu
610                 615                 620

Glu Lys Cys Cys Ala Ala Ala Asp Pro His Glu Cys Tyr Ala Lys Val
625                 630                 635                 640

Phe Asp Glu Phe Lys Pro Leu Val Glu Glu Pro Gln Asn Leu Ile Lys
                645                 650                 655

Gln Asn Cys Glu Leu Phe Glu Gln Leu Gly Glu Tyr Lys Phe Gln Asn
            660                 665                 670

Ala Leu Leu Val Arg Tyr Thr Lys Lys Val Pro Gln Val Ser Thr Pro
            675                 680                 685

Thr Leu Val Glu Val Ser Arg Asn Leu Gly Lys Val Gly Ser Lys Cys
690                 695                 700

Cys Lys His Pro Glu Ala Lys Arg Met Pro Cys Ala Glu Asp Tyr Leu
705                 710                 715                 720

Ser Val Val Leu Asn Gln Leu Cys Val Leu His Glu Lys Thr Pro Val
                725                 730                 735

Ser Asp Arg Val Thr Lys Cys Cys Thr Glu Ser Leu Val Asn Arg Arg
            740                 745                 750

Pro Cys Phe Ser Ala Leu Glu Val Asp Glu Thr Tyr Val Pro Lys Glu
            755                 760                 765

Phe Asn Ala Glu Thr Phe Thr Phe His Ala Asp Ile Cys Thr Leu Ser
770                 775                 780

Glu Lys Glu Arg Gln Ile Lys Lys Gln Thr Ala Leu Val Glu Leu Val
785                 790                 795                 800

Lys His Lys Pro Lys Ala Thr Lys Glu Gln Leu Lys Ala Val Met Asp
                805                 810                 815

Asp Phe Ala Ala Phe Val Glu Lys Cys Cys Lys Ala Asp Asp Lys Glu
            820                 825                 830

Thr Cys Phe Ala Glu Glu Gly Lys Lys Leu Val Ala Ala Ser Gln Ala
            835                 840                 845

Ala Leu Gly Leu
    850

<210> SEQ ID NO 21
<211> LENGTH: 862
<212> TYPE: PRT
<213> ORGANISM: Artificial Sequence
<220> FEATURE:
<223> OTHER INFORMATION: Synthetic Sequence

<400> SEQUENCE: 21

Met Arg Ile Cys Ser Phe Asn Val Arg Ser Phe Gly Glu Ser Lys Gln
1               5                   10                  15

Glu Asp Lys Asn Ala Met Asp Val Ile Val Lys Val Ile Lys Arg Cys
            20                  25                  30

Asp Ile Ile Leu Val Met Glu Ile Lys Asp Ser Asn Asn Arg Ile Cys
        35                  40                  45
```

```
Pro Ile Leu Met Glu Lys Leu Asn Arg Asn Ser Arg Arg Gly Ile Thr
    50                  55                  60
Tyr Asn Tyr Val Ile Ser Ser Arg Leu Gly Arg Asn Thr Tyr Lys Glu
65                  70                  75                  80
Gln Tyr Ala Phe Leu Tyr Lys Glu Lys Leu Val Ser Val Lys Arg Ser
                85                  90                  95
Tyr His Tyr His Asp Tyr Gln Asp Gly Asp Ala Asp Val Phe Ser Arg
            100                 105                 110
Glu Pro Phe Val Val Trp Phe Gln Ser Pro His Thr Ala Val Lys Asp
        115                 120                 125
Phe Val Ile Ile Pro Leu His Thr Thr Pro Glu Thr Ser Val Lys Glu
    130                 135                 140
Ile Asp Glu Leu Val Glu Val Tyr Thr Asp Val Lys His Arg Trp Lys
145                 150                 155                 160
Ala Glu Asn Phe Ile Phe Met Gly Asp Phe Asn Ala Gly Cys Ser Tyr
                165                 170                 175
Val Pro Lys Lys Ala Trp Lys Asn Ile Arg Leu Arg Thr Asp Pro Arg
            180                 185                 190
Phe Val Trp Leu Ile Gly Asp Gln Glu Asp Thr Thr Val Lys Lys Ser
        195                 200                 205
Thr Asn Cys Ala Tyr Asp Arg Ile Val Leu Arg Gly Gln Glu Ile Val
    210                 215                 220
Ser Ser Val Val Pro Lys Ser Asn Ser Val Phe Asp Phe Gln Lys Ala
225                 230                 235                 240
Tyr Lys Leu Thr Glu Glu Glu Ala Leu Asp Val Ser Asp His Tyr Pro
                245                 250                 255
Val Glu Val Met Leu Lys Gly Gly Gly Ser Gly Gly Gly Gly Ser
            260                 265                 270
Gly Gly Gly Gly Ser Asp Ala His Lys Ser Glu Val Ala His Arg Phe
        275                 280                 285
Lys Asp Leu Gly Glu Glu Asn Phe Lys Ala Leu Val Leu Ile Ala Phe
    290                 295                 300
Ala Gln Tyr Leu Gln Gln Cys Pro Phe Glu Asp His Val Lys Leu Val
305                 310                 315                 320
Asn Glu Val Thr Glu Phe Ala Lys Thr Cys Val Ala Asp Glu Ser Ala
                325                 330                 335
Glu Asn Cys Asp Lys Ser Leu His Thr Leu Phe Gly Asp Lys Leu Cys
            340                 345                 350
Thr Val Ala Thr Leu Arg Glu Thr Tyr Gly Glu Met Ala Asp Cys Cys
        355                 360                 365
Ala Lys Gln Glu Pro Glu Arg Asn Glu Cys Phe Leu Gln His Lys Asp
    370                 375                 380
Asp Asn Pro Asn Leu Pro Arg Leu Val Arg Pro Glu Val Asp Val Met
385                 390                 395                 400
Cys Thr Ala Phe His Asp Asn Glu Glu Thr Phe Leu Lys Lys Tyr Leu
                405                 410                 415
Tyr Glu Ile Ala Arg Arg His Pro Tyr Phe Tyr Ala Pro Glu Leu Leu
            420                 425                 430
Phe Phe Ala Lys Arg Tyr Lys Ala Ala Phe Thr Glu Cys Cys Gln Ala
        435                 440                 445
Ala Asp Lys Ala Ala Cys Leu Leu Pro Lys Leu Asp Glu Leu Arg Asp
    450                 455                 460
```

```
Glu Gly Lys Ala Ser Ser Ala Lys Gln Arg Leu Lys Cys Ala Ser Leu
465                 470                 475                 480

Gln Lys Phe Gly Glu Arg Ala Phe Lys Ala Trp Ala Val Ala Arg Leu
            485                 490                 495

Ser Gln Arg Phe Pro Lys Ala Glu Phe Ala Glu Val Ser Lys Leu Val
                500                 505                 510

Thr Asp Leu Thr Lys Val His Thr Glu Cys Cys His Gly Asp Leu Leu
            515                 520                 525

Glu Cys Ala Asp Asp Arg Ala Asp Leu Ala Lys Tyr Ile Cys Glu Asn
        530                 535                 540

Gln Asp Ser Ile Ser Ser Lys Leu Lys Glu Cys Cys Glu Lys Pro Leu
545                 550                 555                 560

Leu Glu Lys Ser His Cys Ile Ala Glu Val Glu Asn Asp Glu Met Pro
                565                 570                 575

Ala Asp Leu Pro Ser Leu Ala Ala Asp Phe Val Glu Ser Lys Asp Val
            580                 585                 590

Cys Lys Asn Tyr Ala Glu Ala Lys Asp Val Phe Leu Gly Met Phe Leu
        595                 600                 605

Tyr Glu Tyr Ala Arg Arg His Pro Asp Tyr Ser Val Val Leu Leu Leu
610                 615                 620

Arg Leu Ala Lys Thr Tyr Glu Thr Thr Leu Glu Lys Cys Cys Ala Ala
625                 630                 635                 640

Ala Asp Pro His Glu Cys Tyr Ala Lys Val Phe Asp Glu Phe Lys Pro
                645                 650                 655

Leu Val Glu Glu Pro Gln Asn Leu Ile Lys Gln Asn Cys Glu Leu Phe
            660                 665                 670

Glu Gln Leu Gly Glu Tyr Lys Phe Gln Asn Ala Leu Leu Val Arg Tyr
        675                 680                 685

Thr Lys Lys Val Pro Gln Val Ser Thr Pro Thr Leu Val Glu Val Ser
690                 695                 700

Arg Asn Leu Gly Lys Val Gly Ser Lys Cys Cys Lys His Pro Glu Ala
705                 710                 715                 720

Lys Arg Met Pro Cys Ala Glu Asp Tyr Leu Ser Val Val Leu Asn Gln
                725                 730                 735

Leu Cys Val Leu His Glu Lys Thr Pro Val Ser Asp Arg Val Thr Lys
            740                 745                 750

Cys Cys Thr Glu Ser Leu Val Asn Arg Arg Pro Cys Phe Ser Ala Leu
        755                 760                 765

Glu Val Asp Glu Thr Tyr Val Pro Lys Glu Phe Asn Ala Glu Thr Phe
770                 775                 780

Thr Phe His Ala Asp Ile Cys Thr Leu Ser Glu Lys Glu Arg Gln Ile
785                 790                 795                 800

Lys Lys Gln Thr Ala Leu Val Glu Leu Val Lys His Lys Pro Lys Ala
                805                 810                 815

Thr Lys Glu Gln Leu Lys Ala Val Met Asp Asp Phe Ala Ala Phe Val
            820                 825                 830

Glu Lys Cys Cys Lys Ala Asp Asp Lys Glu Thr Cys Phe Ala Glu Glu
        835                 840                 845

Gly Lys Lys Leu Val Ala Ala Ser Gln Ala Ala Leu Gly Leu
    850                 855                 860

<210> SEQ ID NO 22
<211> LENGTH: 885
<212> TYPE: PRT
```

<213> ORGANISM: Artificial Sequence
<220> FEATURE:
<223> OTHER INFORMATION: Synthetic Sequence

<400> SEQUENCE: 22

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
370                 375                 380

Gln Asn Leu Ile Lys Gln Asn Cys Glu Leu Phe Glu Gln Leu Gly Glu

```
385                 390                 395                 400
Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
                450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
                530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Gly Gly Gly Ser Gly Gly
                580                 585                 590

Gly Gly Ser Gly Gly Gly Ser Met Arg Ile Cys Ser Phe Asn Val
                595                 600                 605

Arg Ser Phe Gly Glu Ser Lys Gln Glu Asp Lys Asn Ala Met Asp Val
                610                 615                 620

Ile Val Lys Val Ile Lys Arg Cys Asp Ile Ile Leu Val Met Glu Ile
625                 630                 635                 640

Lys Asp Ser Asn Asn Arg Ile Cys Pro Ile Leu Met Glu Lys Leu Asn
                645                 650                 655

Arg Asn Ser Arg Arg Gly Ile Thr Tyr Asn Tyr Val Ile Ser Ser Arg
                660                 665                 670

Leu Gly Arg Asn Thr Tyr Lys Glu Gln Tyr Ala Phe Leu Tyr Lys Glu
                675                 680                 685

Lys Leu Val Ser Val Lys Arg Ser Tyr His Tyr His Asp Tyr Gln Asp
                690                 695                 700

Gly Asp Ala Asp Val Phe Ser Arg Glu Pro Phe Val Val Trp Phe Gln
705                 710                 715                 720

Ser Pro His Thr Ala Val Lys Asp Phe Val Ile Pro Leu His Thr
                725                 730                 735

Thr Pro Glu Thr Ser Val Lys Glu Ile Asp Glu Leu Val Glu Val Tyr
                740                 745                 750

Thr Asp Val Lys His Arg Trp Lys Ala Glu Asn Phe Ile Phe Met Gly
                755                 760                 765

Asp Phe Asn Ala Gly Cys Ser Tyr Val Pro Lys Lys Ala Trp Lys Asn
                770                 775                 780

Ile Arg Leu Arg Thr Asp Pro Arg Phe Val Trp Leu Ile Gly Asp Gln
785                 790                 795                 800

Glu Asp Thr Thr Val Lys Lys Ser Thr Asn Cys Ala Tyr Asp Arg Ile
                805                 810                 815
```

```
Val Leu Arg Gly Gln Glu Ile Val Ser Ser Val Pro Lys Ser Asn
            820                 825                 830

Ser Val Phe Asp Phe Gln Lys Ala Tyr Lys Leu Thr Glu Glu Ala
            835                 840                 845

Leu Asp Val Ser Asp His Phe Pro Val Glu Phe Lys Leu Gln Ser Ser
850                 855                 860

Arg Ala Phe Thr Asn Ser Lys Lys Ser Val Thr Leu Arg Lys Lys Thr
865                 870                 875                 880

Lys Ser Lys Arg Ser
                885

<210> SEQ ID NO 23
<211> LENGTH: 884
<212> TYPE: PRT
<213> ORGANISM: Artificial Sequence
<220> FEATURE:
<223> OTHER INFORMATION: Synthetic Sequence

<400> SEQUENCE: 23

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285
```

```
Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ala Pro Ala Pro Ala Pro Ala
            580                 585                 590

Pro Ala Pro Ala Pro Ala Pro Met Arg Ile Cys Ser Phe Asn Val Arg
            595                 600                 605

Ser Phe Gly Glu Ser Lys Gln Glu Asp Lys Asn Ala Met Asp Val Ile
    610                 615                 620

Val Lys Val Ile Lys Arg Cys Asp Ile Ile Leu Val Met Glu Ile Lys
625                 630                 635                 640

Asp Ser Asn Asn Arg Ile Cys Pro Ile Leu Met Glu Lys Leu Asn Arg
                645                 650                 655

Asn Ser Arg Arg Gly Ile Thr Tyr Asn Tyr Val Ile Ser Ser Arg Leu
            660                 665                 670

Gly Arg Asn Thr Tyr Lys Glu Gln Tyr Ala Phe Leu Tyr Lys Glu Lys
        675                 680                 685

Leu Val Ser Val Lys Arg Ser Tyr His Tyr His Asp Tyr Gln Asp Gly
    690                 695                 700
```

-continued

```
Asp Ala Asp Val Phe Ser Arg Glu Pro Phe Val Trp Phe Gln Ser
705                 710                 715                 720

Pro His Thr Ala Val Lys Asp Phe Val Ile Ile Pro Leu His Thr Thr
                725                 730                 735

Pro Glu Thr Ser Val Lys Glu Ile Asp Glu Leu Val Glu Val Tyr Thr
                740                 745                 750

Asp Val Lys His Arg Trp Lys Ala Glu Asn Phe Ile Phe Met Gly Asp
                755                 760                 765

Phe Asn Ala Gly Cys Ser Tyr Val Pro Lys Lys Ala Trp Lys Asn Ile
            770                 775                 780

Arg Leu Arg Thr Asp Pro Arg Phe Val Trp Leu Ile Gly Asp Gln Glu
785                 790                 795                 800

Asp Thr Thr Val Lys Lys Ser Thr Asn Cys Ala Tyr Asp Arg Ile Val
                805                 810                 815

Leu Arg Gly Gln Glu Ile Val Ser Ser Val Pro Lys Ser Asn Ser
            820                 825                 830

Val Phe Asp Phe Gln Lys Ala Tyr Lys Leu Thr Glu Glu Ala Leu
        835                 840                 845

Asp Val Ser Asp His Phe Pro Val Glu Phe Lys Leu Gln Ser Ser Arg
850                 855                 860

Ala Phe Thr Asn Ser Lys Ser Val Thr Leu Arg Lys Lys Thr Lys
865                 870                 875                 880

Ser Lys Arg Ser

<210> SEQ ID NO 24
<211> LENGTH: 882
<212> TYPE: PRT
<213> ORGANISM: Artificial Sequence
<220> FEATURE:
<223> OTHER INFORMATION: Synthetic Sequence

<400> SEQUENCE: 24

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
```

-continued

```
            180                 185                 190
Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
            210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                    245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
            290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                    325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
            370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                    405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
            450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                    485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
            515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                    565                 570                 575

Ala Ala Ser Gln Ala Ala Leu Gly Leu Ala Glu Ala Ala Lys Glu
            580                 585                 590

Ala Ala Ala Lys Ala Met Arg Ile Cys Ser Phe Asn Val Arg Ser Phe
            595                 600                 605
```

```
Gly Glu Ser Lys Gln Glu Asp Lys Asn Ala Met Asp Val Ile Val Lys
    610                 615                 620

Val Ile Lys Arg Cys Asp Ile Ile Leu Val Met Glu Ile Lys Asp Ser
625                 630                 635                 640

Asn Asn Arg Ile Cys Pro Ile Leu Met Glu Lys Leu Asn Arg Asn Ser
                645                 650                 655

Arg Arg Gly Ile Thr Tyr Asn Tyr Val Ile Ser Ser Arg Leu Gly Arg
            660                 665                 670

Asn Thr Tyr Lys Glu Gln Tyr Ala Phe Leu Tyr Lys Glu Lys Leu Val
        675                 680                 685

Ser Val Lys Arg Ser Tyr His Tyr His Asp Tyr Gln Asp Gly Asp Ala
    690                 695                 700

Asp Val Phe Ser Arg Glu Pro Phe Val Val Trp Phe Gln Ser Pro His
705                 710                 715                 720

Thr Ala Val Lys Asp Phe Val Ile Ile Pro Leu His Thr Thr Pro Glu
                725                 730                 735

Thr Ser Val Lys Glu Ile Asp Glu Leu Val Glu Val Tyr Thr Asp Val
            740                 745                 750

Lys His Arg Trp Lys Ala Glu Asn Phe Ile Phe Met Gly Asp Phe Asn
        755                 760                 765

Ala Gly Cys Ser Tyr Val Pro Lys Lys Ala Trp Lys Asn Ile Arg Leu
    770                 775                 780

Arg Thr Asp Pro Arg Phe Val Trp Leu Ile Gly Asp Gln Glu Asp Thr
785                 790                 795                 800

Thr Val Lys Lys Ser Thr Asn Cys Ala Tyr Asp Arg Ile Val Leu Arg
                805                 810                 815

Gly Gln Glu Ile Val Ser Ser Val Pro Lys Ser Asn Ser Val Phe
            820                 825                 830

Asp Phe Gln Lys Ala Tyr Lys Leu Thr Glu Glu Ala Leu Asp Val
        835                 840                 845

Ser Asp His Phe Pro Val Glu Phe Lys Leu Gln Ser Ser Arg Ala Phe
    850                 855                 860

Thr Asn Ser Lys Lys Ser Val Thr Leu Arg Lys Lys Thr Lys Ser Lys
865                 870                 875                 880

Arg Ser

<210> SEQ ID NO 25
<211> LENGTH: 854
<212> TYPE: PRT
<213> ORGANISM: Artificial Sequence
<220> FEATURE:
<223> OTHER INFORMATION: Synthetic Sequence

<400> SEQUENCE: 25

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80
```

```
Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
                180                 185                 190

Ser Ala Lys Gln Arg Leu Lys Cys Ala Ser Leu Gln Lys Phe Gly Glu
            195                 200                 205

Arg Ala Phe Lys Ala Trp Ala Val Ala Arg Leu Ser Gln Arg Phe Pro
        210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
                260                 265                 270

Ser Lys Leu Lys Glu Cys Cys Glu Lys Pro Leu Leu Glu Lys Ser His
            275                 280                 285

Cys Ile Ala Glu Val Glu Asn Asp Glu Met Pro Ala Asp Leu Pro Ser
        290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
            355                 360                 365

Cys Tyr Ala Lys Val Phe Asp Glu Phe Lys Pro Leu Val Glu Glu Pro
        370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
            435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
```

```
                500             505             510
Ile Cys Thr Leu Ser Glu Lys Glu Arg Gln Ile Lys Lys Gln Thr Ala
                515             520             525
Leu Val Glu Leu Val Lys His Lys Pro Lys Ala Thr Lys Glu Gln Leu
                530             535             540
Lys Ala Val Met Asp Asp Phe Ala Phe Val Glu Lys Cys Cys Lys
545             550             555             560
Ala Asp Asp Lys Glu Thr Cys Phe Ala Glu Glu Gly Lys Lys Leu Val
                565             570             575
Ala Ala Ser Gln Ala Ala Leu Gly Leu Ser Gly Gly Ser Gly Ser Ser
                580             585             590
Met Arg Ile Cys Ser Phe Asn Val Arg Ser Phe Gly Glu Ser Lys Gln
                595             600             605
Glu Asp Lys Asn Ala Met Asp Val Ile Val Lys Val Ile Lys Arg Cys
                610             615             620
Asp Ile Ile Leu Val Met Glu Ile Lys Asp Ser Asn Asn Arg Ile Cys
625             630             635             640
Pro Ile Leu Met Glu Lys Leu Asn Arg Asn Ser Arg Arg Gly Ile Thr
                645             650             655
Tyr Asn Tyr Val Ile Ser Ser Arg Leu Gly Arg Asn Thr Tyr Lys Glu
                660             665             670
Gln Tyr Ala Phe Leu Tyr Lys Glu Lys Leu Val Ser Val Lys Arg Ser
                675             680             685
Tyr His Tyr His Asp Tyr Gln Asp Gly Asp Ala Asp Val Phe Ser Arg
                690             695             700
Glu Pro Phe Val Val Trp Phe Gln Ser Pro His Thr Ala Val Lys Asp
705             710             715             720
Phe Val Ile Ile Pro Leu His Thr Thr Pro Glu Thr Ser Val Lys Glu
                725             730             735
Ile Asp Glu Leu Val Glu Val Tyr Thr Asp Val Lys His Arg Trp Lys
                740             745             750
Ala Glu Asn Phe Ile Phe Met Gly Asp Phe Asn Ala Gly Cys Ser Tyr
                755             760             765
Val Pro Lys Lys Ala Trp Lys Asn Ile Arg Leu Arg Thr Asp Pro Arg
                770             775             780
Phe Val Trp Leu Ile Gly Asp Gln Glu Asp Thr Thr Val Lys Lys Ser
785             790             795             800
Thr Asn Cys Ala Tyr Asp Arg Ile Val Leu Arg Gly Gln Glu Ile Val
                805             810             815
Ser Ser Val Val Pro Lys Ser Asn Ser Val Phe Asp Phe Gln Lys Ala
                820             825             830
Tyr Lys Leu Thr Glu Glu Glu Ala Leu Asp Val Ser Asp His Phe Pro
                835             840             845
Val Glu Phe Lys Leu Gln
    850

<210> SEQ ID NO 26
<211> LENGTH: 863
<212> TYPE: PRT
<213> ORGANISM: Artificial Sequence
<220> FEATURE:
<223> OTHER INFORMATION: Synthetic Sequence

<400> SEQUENCE: 26

Asp Ala His Lys Ser Glu Val Ala His Arg Phe Lys Asp Leu Gly Glu
```

-continued

```
 1               5                   10                  15
Glu Asn Phe Lys Ala Leu Val Leu Ile Ala Phe Ala Gln Tyr Leu Gln
                20                  25                  30
Gln Cys Pro Phe Glu Asp His Val Lys Leu Val Asn Glu Val Thr Glu
                35                  40                  45
Phe Ala Lys Thr Cys Val Ala Asp Glu Ser Ala Glu Asn Cys Asp Lys
                50                  55                  60
Ser Leu His Thr Leu Phe Gly Asp Lys Leu Cys Thr Val Ala Thr Leu
 65                 70                  75                  80
Arg Glu Thr Tyr Gly Glu Met Ala Asp Cys Cys Ala Lys Gln Glu Pro
                85                  90                  95
Glu Arg Asn Glu Cys Phe Leu Gln His Lys Asp Asp Asn Pro Asn Leu
                100                 105                 110
Pro Arg Leu Val Arg Pro Glu Val Asp Val Met Cys Thr Ala Phe His
                115                 120                 125
Asp Asn Glu Glu Thr Phe Leu Lys Lys Tyr Leu Tyr Glu Ile Ala Arg
                130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
                180                 185                 190
Ser Ala Lys Gln Arg Leu Lys Cys Ala Ser Leu Gln Lys Phe Gly Glu
                195                 200                 205
Arg Ala Phe Lys Ala Trp Ala Val Ala Arg Leu Ser Gln Arg Phe Pro
                210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
                260                 265                 270
Ser Lys Leu Lys Glu Cys Cys Glu Lys Pro Leu Leu Glu Lys Ser His
                275                 280                 285
Cys Ile Ala Glu Val Glu Asn Asp Glu Met Pro Ala Asp Leu Pro Ser
                290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
                355                 360                 365
Cys Tyr Ala Lys Val Phe Asp Glu Phe Lys Pro Leu Val Glu Glu Pro
                370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
                420                 425                 430
```

```
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
            500                 505                 510
Ile Cys Thr Leu Ser Glu Lys Glu Arg Gln Ile Lys Lys Gln Thr Ala
        515                 520                 525
Leu Val Glu Leu Val Lys His Lys Pro Lys Ala Thr Lys Glu Gln Leu
530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Ser Gly Gly Ser Gly Gly Ser
            580                 585                 590
Gly Gly Ser Gly Gly Ser Gly Ser Met Arg Ile Cys Ser Phe Asn
        595                 600                 605
Val Arg Ser Phe Gly Glu Ser Lys Gln Glu Asp Lys Asn Ala Met Asp
        610                 615                 620
Val Ile Val Lys Val Ile Lys Arg Cys Asp Ile Ile Leu Val Met Glu
625                 630                 635                 640
Ile Lys Asp Ser Asn Asn Arg Ile Cys Pro Ile Leu Met Glu Lys Leu
                645                 650                 655
Asn Arg Asn Ser Arg Arg Gly Ile Thr Tyr Asn Tyr Val Ile Ser Ser
            660                 665                 670
Arg Leu Gly Arg Asn Thr Tyr Lys Glu Gln Tyr Ala Phe Leu Tyr Lys
        675                 680                 685
Glu Lys Leu Val Ser Val Lys Arg Ser Tyr His Tyr His Asp Tyr Gln
        690                 695                 700
Asp Gly Asp Ala Asp Val Phe Ser Arg Glu Pro Phe Val Val Trp Phe
705                 710                 715                 720
Gln Ser Pro His Thr Ala Val Lys Asp Phe Val Ile Ile Pro Leu His
                725                 730                 735
Thr Thr Pro Glu Thr Ser Val Lys Glu Ile Asp Glu Leu Val Glu Val
            740                 745                 750
Tyr Thr Asp Val Lys His Arg Trp Lys Ala Glu Asn Phe Ile Phe Met
        755                 760                 765
Gly Asp Phe Asn Ala Gly Cys Ser Tyr Val Pro Lys Lys Ala Trp Lys
        770                 775                 780
Asn Ile Arg Leu Arg Thr Asp Pro Arg Phe Val Trp Leu Ile Gly Asp
785                 790                 795                 800
Gln Glu Asp Thr Thr Val Lys Lys Ser Thr Asn Cys Ala Tyr Asp Arg
                805                 810                 815
Ile Val Leu Arg Gly Gln Glu Ile Val Ser Ser Val Val Pro Lys Ser
            820                 825                 830
Asn Ser Val Phe Asp Phe Gln Lys Ala Tyr Lys Leu Thr Glu Glu
        835                 840                 845
```

```
Ala Leu Asp Val Ser Asp His Phe Pro Val Glu Phe Lys Leu Gln
    850                 855                 860
```

<210> SEQ ID NO 27
<211> LENGTH: 878
<212> TYPE: PRT
<213> ORGANISM: Artificial Sequence
<220> FEATURE:
<223> OTHER INFORMATION: Synthetic Sequence

<400> SEQUENCE: 27

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350
```

```
Tyr Glu Thr Thr Leu Glu Lys Cys Cys Ala Ala Asp Pro His Glu
            355                 360                 365

Cys Tyr Ala Lys Val Phe Asp Glu Phe Lys Pro Leu Val Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
            420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
        450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
        530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ser Gly Gly Ser Gly Gly Ser
            580                 585                 590

Gly Gly Ser Gly Gly Ser Gly Gly Ser Gly Gly Ser Gly Gly Ser Gly
        595                 600                 605

Gly Ser Gly Gly Ser Gly Ser Ser Met Arg Ile Cys Ser Phe Asn Val
        610                 615                 620

Arg Ser Phe Gly Glu Ser Lys Gln Glu Asp Lys Asn Ala Met Asp Val
625                 630                 635                 640

Ile Val Lys Val Ile Lys Arg Cys Asp Ile Ile Leu Val Met Glu Ile
                645                 650                 655

Lys Asp Ser Asn Asn Arg Ile Cys Pro Ile Leu Met Glu Lys Leu Asn
            660                 665                 670

Arg Asn Ser Arg Arg Gly Ile Thr Tyr Asn Tyr Val Ile Ser Ser Arg
        675                 680                 685

Leu Gly Arg Asn Thr Tyr Lys Glu Gln Tyr Ala Phe Leu Tyr Lys Glu
        690                 695                 700

Lys Leu Val Ser Val Lys Arg Ser Tyr His Tyr His Asp Tyr Gln Asp
705                 710                 715                 720

Gly Asp Ala Asp Val Phe Ser Arg Glu Pro Phe Val Val Trp Phe Gln
                725                 730                 735

Ser Pro His Thr Ala Val Lys Asp Phe Val Ile Ile Pro Leu His Thr
            740                 745                 750

Thr Pro Glu Thr Ser Val Lys Glu Ile Asp Glu Leu Val Glu Val Tyr
        755                 760                 765

Thr Asp Val Lys His Arg Trp Lys Ala Glu Asn Phe Ile Phe Met Gly
```

```
            770                 775                 780
Asp Phe Asn Ala Gly Cys Ser Tyr Val Pro Lys Lys Ala Trp Lys Asn
785                 790                 795                 800

Ile Arg Leu Arg Thr Asp Pro Arg Phe Val Trp Leu Ile Gly Asp Gln
                805                 810                 815

Glu Asp Thr Thr Val Lys Lys Ser Thr Asn Cys Ala Tyr Asp Arg Ile
            820                 825                 830

Val Leu Arg Gly Gln Glu Ile Val Ser Ser Val Val Pro Lys Ser Asn
            835                 840                 845

Ser Val Phe Asp Phe Gln Lys Ala Tyr Lys Leu Thr Glu Glu Glu Ala
        850                 855                 860

Leu Asp Val Ser Asp His Phe Pro Val Glu Phe Lys Leu Gln
865                 870                 875

<210> SEQ ID NO 28
<211> LENGTH: 1494
<212> TYPE: PRT
<213> ORGANISM: Artificial Sequence
<220> FEATURE:
<223> OTHER INFORMATION: Synthetic Sequence

<400> SEQUENCE: 28

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
                20                  25                  30

Gln Cys Pro Phe Glu Asp His Val Lys Leu Val Asn Glu Val Thr Glu
            35                  40                  45

Phe Ala Lys Thr Cys Val Ala Asp Glu Ser Ala Glu Asn Cys Asp Lys
        50                  55                  60

Ser Leu His Thr Leu Phe Gly Asp Lys Leu Cys Thr Val Ala Thr Leu
65              70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
```

```
                260             265                 270
Ser Lys Leu Lys Glu Cys Cys Glu Lys Pro Leu Leu Glu Lys Ser His
            275                 280             285
Cys Ile Ala Glu Val Glu Asn Asp Glu Met Pro Ala Asp Leu Pro Ser
            290                 295             300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
                340                 345                 350
Tyr Glu Thr Thr Leu Glu Lys Cys Cys Ala Ala Ala Asp Pro His Glu
            355                 360                 365
Cys Tyr Ala Lys Val Phe Asp Glu Phe Lys Pro Leu Val Glu Glu Pro
            370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
            435                 440                 445
Ala Glu Asp Tyr Leu Ser Val Val Leu Asn Gln Leu Cys Val Leu His
            450                 455                 460
Glu Lys Thr Pro Val Ser Asp Arg Val Thr Lys Cys Cys Thr Glu Ser
465                 470                 475                 480
Leu Val Asn Arg Arg Pro Cys Phe Ser Ala Leu Glu Val Asp Glu Thr
                485                 490                 495
Tyr Val Pro Lys Glu Phe Asn Ala Glu Thr Phe Thr Phe His Ala Asp
                500                 505                 510
Ile Cys Thr Leu Ser Glu Lys Glu Arg Gln Ile Lys Lys Gln Thr Ala
            515                 520                 525
Leu Val Glu Leu Val Lys His Lys Pro Lys Ala Thr Lys Glu Gln Leu
            530                 535                 540
Lys Ala Val Met Asp Asp Phe Ala Ala Phe Val Glu Lys Cys Cys Lys
545                 550                 555                 560
Ala Asp Asp Lys Glu Thr Cys Phe Ala Glu Glu Gly Lys Lys Leu Val
                565                 570                 575
Ala Ala Ser Gln Ala Ala Leu Gly Leu Ser Gly Ser Gly Gly Ser
            580                 585                 590
Gly Gly Ser Gly Gly Ser Gly Ser Gly Gly Ser Gly Gly Ser Gly
            595                 600                 605
Gly Ser Gly Gly Ser Gly Ser Ser Met Arg Ile Cys Ser Phe Asn Val
            610                 615                 620
Arg Ser Phe Gly Glu Ser Lys Gln Glu Asp Lys Asn Ala Met Asp Val
625                 630                 635                 640
Ile Val Lys Val Ile Lys Arg Cys Asp Ile Leu Val Met Glu Ile
                645                 650                 655
Lys Asp Ser Asn Asn Arg Ile Cys Pro Ile Leu Met Glu Lys Leu Asn
                660                 665                 670
Arg Asn Ser Arg Arg Gly Ile Thr Tyr Asn Tyr Val Ile Ser Ser Arg
            675                 680                 685
```

-continued

Leu Gly Arg Asn Thr Tyr Lys Glu Gln Tyr Ala Phe Leu Tyr Lys Glu
690                 695                 700

Lys Leu Val Ser Val Lys Arg Ser Tyr His Tyr His Asp Tyr Gln Asp
705                 710                 715                 720

Gly Asp Ala Asp Val Phe Ser Arg Glu Pro Phe Val Val Trp Phe Gln
                725                 730                 735

Ser Pro His Thr Ala Val Lys Asp Phe Val Ile Ile Pro Leu His Thr
            740                 745                 750

Thr Pro Glu Thr Ser Val Lys Glu Ile Asp Glu Leu Val Glu Val Tyr
        755                 760                 765

Thr Asp Val Lys His Arg Trp Lys Ala Glu Asn Phe Ile Phe Met Gly
770                 775                 780

Asp Phe Asn Ala Gly Cys Ser Tyr Val Pro Lys Lys Ala Trp Lys Asn
785                 790                 795                 800

Ile Arg Leu Arg Thr Asp Pro Arg Phe Val Trp Leu Ile Gly Asp Gln
                805                 810                 815

Glu Asp Thr Thr Val Lys Lys Ser Thr Asn Cys Ala Tyr Asp Arg Ile
            820                 825                 830

Val Leu Arg Gly Gln Glu Ile Val Ser Ser Val Val Pro Lys Ser Asn
        835                 840                 845

Ser Val Phe Asp Phe Gln Lys Ala Tyr Lys Leu Thr Glu Glu Glu Ala
850                 855                 860

Leu Asp Val Ser Asp His Phe Pro Val Glu Phe Lys Leu Gln Ser Ser
865                 870                 875                 880

Gly Gly Ser Gly Gly Ser Gly Gly Ser Gly Gly Ser Gly Gly Ser Gly
                885                 890                 895

Gly Ser Gly Gly Ser Gly Gly Ser Gly Gly Ser Gly Asp Ala His
            900                 905                 910

Lys Ser Glu Val Ala His Arg Phe Lys Asp Leu Gly Glu Glu Asn Phe
        915                 920                 925

Lys Ala Leu Val Leu Ile Ala Phe Ala Gln Tyr Leu Gln Gln Cys Pro
930                 935                 940

Phe Glu Asp His Val Lys Leu Val Asn Glu Val Thr Glu Phe Ala Lys
945                 950                 955                 960

Thr Cys Val Ala Asp Glu Ser Ala Glu Asn Cys Asp Lys Ser Leu His
                965                 970                 975

Thr Leu Phe Gly Asp Lys Leu Cys Thr Val Ala Thr Leu Arg Glu Thr
            980                 985                 990

Tyr Gly Glu Met Ala Asp Cys Cys Ala Lys Gln Glu Pro Glu Arg Asn
        995                 1000                1005

Glu Cys Phe Leu Gln His Lys Asp Asp Asn Pro Asn Leu Pro Arg
1010                1015                1020

Leu Val Arg Pro Glu Val Asp Val Met Cys Thr Ala Phe His Asp
1025                1030                1035

Asn Glu Glu Thr Phe Leu Lys Lys Tyr Leu Tyr Glu Ile Ala Arg
1040                1045                1050

Arg His Pro Tyr Phe Tyr Ala Pro Glu Leu Leu Phe Phe Ala Lys
1055                1060                1065

Arg Tyr Lys Ala Ala Phe Thr Glu Cys Cys Gln Ala Ala Asp Lys
1070                1075                1080

Ala Ala Cys Leu Leu Pro Lys Leu Asp Glu Leu Arg Asp Glu Gly
1085                1090                1095

```
Lys Ala Ser Ser Ala Lys Gln Arg Leu Lys Cys Ala Ser Leu Gln
    1100                1105                1110
Lys Phe Gly Glu Arg Ala Phe Lys Ala Trp Ala Val Ala Arg Leu
    1115                1120                1125
Ser Gln Arg Phe Pro Lys Ala Glu Phe Ala Glu Val Ser Lys Leu
    1130                1135                1140
Val Thr Asp Leu Thr Lys Val His Thr Glu Cys Cys His Gly Asp
    1145                1150                1155
Leu Leu Glu Cys Ala Asp Asp Arg Ala Asp Leu Ala Lys Tyr Ile
    1160                1165                1170
Cys Glu Asn Gln Asp Ser Ile Ser Ser Lys Leu Lys Glu Cys Cys
    1175                1180                1185
Glu Lys Pro Leu Leu Glu Lys Ser His Cys Ile Ala Glu Val Glu
    1190                1195                1200
Asn Asp Glu Met Pro Ala Asp Leu Pro Ser Leu Ala Ala Asp Phe
    1205                1210                1215
Val Glu Ser Lys Asp Val Cys Lys Asn Tyr Ala Glu Ala Lys Asp
    1220                1225                1230
Val Phe Leu Gly Met Phe Leu Tyr Glu Tyr Ala Arg Arg His Pro
    1235                1240                1245
Asp Tyr Ser Val Val Leu Leu Leu Arg Leu Ala Lys Thr Tyr Glu
    1250                1255                1260
Thr Thr Leu Glu Lys Cys Cys Ala Ala Ala Asp Pro His Glu Cys
    1265                1270                1275
Tyr Ala Lys Val Phe Asp Glu Phe Lys Pro Leu Val Glu Glu Pro
    1280                1285                1290
Gln Asn Leu Ile Lys Gln Asn Cys Glu Leu Phe Glu Gln Leu Gly
    1295                1300                1305
Glu Tyr Lys Phe Gln Asn Ala Leu Leu Val Arg Tyr Thr Lys Lys
    1310                1315                1320
Val Pro Gln Val Ser Thr Pro Thr Leu Val Glu Val Ser Arg Asn
    1325                1330                1335
Leu Gly Lys Val Gly Ser Lys Cys Cys Lys His Pro Glu Ala Lys
    1340                1345                1350
Arg Met Pro Cys Ala Glu Asp Tyr Leu Ser Val Val Leu Asn Gln
    1355                1360                1365
Leu Cys Val Leu His Glu Lys Thr Pro Val Ser Asp Arg Val Thr
    1370                1375                1380
Lys Cys Cys Thr Glu Ser Leu Val Asn Arg Arg Pro Cys Phe Ser
    1385                1390                1395
Ala Leu Glu Val Asp Glu Thr Tyr Val Pro Lys Glu Phe Asn Ala
    1400                1405                1410
Glu Thr Phe Thr Phe His Ala Asp Ile Cys Thr Leu Ser Glu Lys
    1415                1420                1425
Glu Arg Gln Ile Lys Lys Gln Thr Ala Leu Val Glu Leu Val Lys
    1430                1435                1440
His Lys Pro Lys Ala Thr Lys Glu Gln Leu Lys Ala Val Met Asp
    1445                1450                1455
Asp Phe Ala Ala Phe Val Glu Lys Cys Cys Lys Ala Asp Asp Lys
    1460                1465                1470
Glu Thr Cys Phe Ala Glu Glu Gly Lys Lys Leu Val Ala Ala Ser
    1475                1480                1485
Gln Ala Ala Leu Gly Leu
```

-continued

1490

<210> SEQ ID NO 29
<211> LENGTH: 879
<212> TYPE: PRT
<213> ORGANISM: Artificial Sequence
<220> FEATURE:
<223> OTHER INFORMATION: Synthetic Sequence

<400> SEQUENCE: 29

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270

Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
            340                 345                 350

Tyr Glu Thr Thr Leu Glu Lys Cys Cys Ala Ala Ala Asp Pro His Glu

```
                355                 360                 365
Cys Tyr Ala Lys Val Phe Asp Glu Phe Lys Pro Leu Val Glu Pro
370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
                435                 440                 445

Ala Glu Asp Tyr Leu Ser Val Val Leu Asn Gln Leu Cys Val Leu His
                450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
                530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ser Gly Gly Ser Gly Gly Ser
                580                 585                 590

Gly Gly Ser Gly Gly Ser Gly Gly Ser Gly Gly Ser Gly Gly Ser Gly
                595                 600                 605

Gly Ser Gly Gly Ser Gly Ser Ser Met Arg Ile Cys Ser Phe Asn Val
                610                 615                 620

Arg Ser Phe Gly Glu Ser Lys Gln Glu Asp Lys Asn Ala Met Asp Val
625                 630                 635                 640

Ile Val Lys Val Ile Lys Arg Cys Asp Ile Ile Leu Val Met Glu Ile
                645                 650                 655

Lys Asp Ser Asn Asn Arg Ile Cys Pro Ile Leu Met Glu Lys Leu Asn
                660                 665                 670

Arg Glu Gln Tyr Ala Phe Leu Tyr Lys Glu Lys Leu Val Ser Val Lys
                675                 680                 685

Arg Ser Tyr His Tyr His Asp Tyr Gln Asp Gly Asp Ala Asp Val Phe
                690                 695                 700

Ser Arg Glu Pro Phe Val Val Trp Phe Gln Ser Pro His Thr Ala Val
705                 710                 715                 720

Lys Asp Phe Val Ile Ile Pro Leu His Thr Thr Pro Glu Thr Ser Val
                725                 730                 735

Lys Glu Ile Asp Glu Leu Val Glu Val Tyr Thr Asp Val Lys His Arg
                740                 745                 750

Trp Lys Ala Glu Asn Phe Ile Phe Met Gly Asp Phe Asn Ala Gly Cys
                755                 760                 765

Ser Tyr Val Pro Lys Lys Ala Trp Lys Asn Ile Arg Leu Arg Thr Asp
                770                 775                 780
```

```
Pro Arg Phe Val Trp Leu Ile Gly Asp Gln Glu Asp Thr Thr Val Lys
785                 790                 795                 800

Lys Ser Thr Asn Cys Ala Tyr Asp Arg Ile Val Leu Arg Gly Gln Glu
            805                 810                 815

Ile Val Ser Ser Val Val Pro Lys Ser Asn Ser Val Phe Asp Phe Gln
        820                 825                 830

Lys Ala Tyr Lys Leu Thr Glu Glu Ala Leu Asp Val Ser Asp His
    835                 840                 845

Phe Pro Val Glu Phe Lys Leu Gln Ser Ser Arg Ala Phe Thr Asn Ser
850                 855                 860

Lys Lys Ser Val Thr Leu Arg Lys Lys Thr Lys Ser Lys Arg Ser
865                 870                 875
```

<210> SEQ ID NO 30
<211> LENGTH: 856
<212> TYPE: PRT
<213> ORGANISM: Artificial Sequence
<220> FEATURE:
<223> OTHER INFORMATION: Synthetic Sequence

<400> SEQUENCE: 30

```
Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
        35                  40                  45

Phe Ala Lys Thr Cys Val Ala Asp Glu Ser Ala Glu Asn Cys Asp Lys
    50                  55                  60

Ser Leu His Thr Leu Phe Gly Asp Lys Leu Cys Thr Val Ala Thr Leu
65                  70                  75                  80

Arg Glu Thr Tyr Gly Glu Met Ala Asp Cys Cys Ala Lys Gln Glu Pro
                85                  90                  95

Glu Arg Asn Glu Cys Phe Leu Gln His Lys Asp Asp Asn Pro Asn Leu
            100                 105                 110

Pro Arg Leu Val Arg Pro Glu Val Asp Val Met Cys Thr Ala Phe His
        115                 120                 125

Asp Asn Glu Glu Thr Phe Leu Lys Lys Tyr Leu Tyr Glu Ile Ala Arg
    130                 135                 140

Arg His Pro Tyr Phe Tyr Ala Pro Glu Leu Leu Phe Phe Ala Lys Arg
145                 150                 155                 160

Tyr Lys Ala Ala Phe Thr Glu Cys Cys Gln Ala Ala Asp Lys Ala Ala
                165                 170                 175

Cys Leu Leu Pro Lys Leu Asp Glu Leu Arg Asp Glu Gly Lys Ala Ser
            180                 185                 190

Ser Ala Lys Gln Arg Leu Lys Cys Ala Ser Leu Gln Lys Phe Gly Glu
        195                 200                 205

Arg Ala Phe Lys Ala Trp Ala Val Ala Arg Leu Ser Gln Arg Phe Pro
    210                 215                 220

Lys Ala Glu Phe Ala Glu Val Ser Lys Leu Val Thr Asp Leu Thr Lys
225                 230                 235                 240

Val His Thr Glu Cys Cys His Gly Asp Leu Leu Glu Cys Ala Asp Asp
                245                 250                 255

Arg Ala Asp Leu Ala Lys Tyr Ile Cys Glu Asn Gln Asp Ser Ile Ser
            260                 265                 270
```

```
Ser Lys Leu Lys Glu Cys Cys Glu Lys Pro Leu Leu Glu Lys Ser His
        275                 280                 285

Cys Ile Ala Glu Val Glu Asn Asp Glu Met Pro Ala Asp Leu Pro Ser
    290                 295                 300

Leu Ala Ala Asp Phe Val Glu Ser Lys Asp Val Cys Lys Asn Tyr Ala
305                 310                 315                 320

Glu Ala Lys Asp Val Phe Leu Gly Met Phe Leu Tyr Glu Tyr Ala Arg
                325                 330                 335

Arg His Pro Asp Tyr Ser Val Val Leu Leu Leu Arg Leu Ala Lys Thr
                340                 345                 350

Tyr Glu Thr Thr Leu Glu Lys Cys Cys Ala Ala Ala Asp Pro His Glu
        355                 360                 365

Cys Tyr Ala Lys Val Phe Asp Glu Phe Lys Pro Leu Val Glu Glu Pro
    370                 375                 380

Gln Asn Leu Ile Lys Gln Asn Cys Glu Leu Phe Glu Gln Leu Gly Glu
385                 390                 395                 400

Tyr Lys Phe Gln Asn Ala Leu Leu Val Arg Tyr Thr Lys Lys Val Pro
                405                 410                 415

Gln Val Ser Thr Pro Thr Leu Val Glu Val Ser Arg Asn Leu Gly Lys
                420                 425                 430

Val Gly Ser Lys Cys Cys Lys His Pro Glu Ala Lys Arg Met Pro Cys
        435                 440                 445

Ala Glu Asp Tyr Leu Ser Val Val Leu Asn Gln Leu Cys Val Leu His
    450                 455                 460

Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
                500                 505                 510

Ile Cys Thr Leu Ser Glu Lys Glu Arg Gln Ile Lys Lys Gln Thr Ala
        515                 520                 525

Leu Val Glu Leu Val Lys His Lys Pro Lys Ala Thr Lys Glu Gln Leu
    530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu Ser Gly Gly Ser Gly Gly Ser
                580                 585                 590

Gly Gly Ser Gly Gly Ser Gly Gly Ser Gly Gly Ser Gly Gly Ser Gly
        595                 600                 605

Gly Ser Gly Gly Ser Gly Ser Ser Met Arg Ile Cys Ser Phe Asn Val
    610                 615                 620

Arg Ser Phe Gly Glu Ser Lys Gln Glu Asp Lys Asn Ala Met Asp Val
625                 630                 635                 640

Ile Val Lys Val Ile Lys Arg Cys Asp Ile Ile Leu Val Met Glu Ile
                645                 650                 655

Lys Asp Ser Asn Asn Arg Ile Cys Pro Ile Leu Met Glu Lys Leu Asn
                660                 665                 670

Arg Glu Gln Tyr Ala Phe Leu Tyr Lys Glu Lys Leu Val Ser Val Lys
        675                 680                 685
```

```
         Arg Ser Tyr His Tyr His Asp Tyr Gln Asp Gly Asp Ala Asp Val Phe
             690                 695                 700

Ser Arg Glu Pro Phe Val Val Trp Phe Gln Ser Pro His Thr Ala Val
         705                 710                 715                 720

Lys Asp Phe Val Ile Ile Pro Leu His Thr Thr Pro Glu Thr Ser Val
                         725                 730                 735

Lys Glu Ile Asp Glu Leu Val Glu Val Tyr Thr Asp Val Lys His Arg
                     740                 745                 750

Trp Lys Ala Glu Asn Phe Ile Phe Met Gly Asp Phe Asn Ala Gly Cys
                 755                 760                 765

Ser Tyr Val Pro Lys Lys Ala Trp Lys Asn Ile Arg Leu Arg Thr Asp
             770                 775                 780

Pro Arg Phe Val Trp Leu Ile Gly Asp Gln Glu Asp Thr Thr Val Lys
         785                 790                 795                 800

Lys Ser Thr Asn Cys Ala Tyr Asp Arg Ile Val Leu Arg Gly Gln Glu
                         805                 810                 815

Ile Val Ser Ser Val Val Pro Lys Ser Asn Ser Val Phe Asp Phe Gln
                     820                 825                 830

Lys Ala Tyr Lys Leu Thr Glu Glu Ala Leu Asp Val Ser Asp His
                 835                 840                 845

Phe Pro Val Glu Phe Lys Leu Gln
             850                 855

<210> SEQ ID NO 31
<211> LENGTH: 5
<212> TYPE: PRT
<213> ORGANISM: Artificial Sequence
<220> FEATURE:
<223> OTHER INFORMATION: Synthetic Sequence

<400> SEQUENCE: 31

Gly Gly Gly Gly Ser
1               5

<210> SEQ ID NO 32
<211> LENGTH: 15
<212> TYPE: PRT
<213> ORGANISM: Artificial Sequence
<220> FEATURE:
<223> OTHER INFORMATION: Synthetic Sequence

<400> SEQUENCE: 32

Gly Gly Gly Gly Ser Gly Gly Gly Gly Ser Gly Gly Gly Gly Ser
1               5                   10                  15

<210> SEQ ID NO 33
<211> LENGTH: 14
<212> TYPE: PRT
<213> ORGANISM: Artificial Sequence
<220> FEATURE:
<223> OTHER INFORMATION: Synthetic Sequence

<400> SEQUENCE: 33

Ala Pro Ala Pro Ala Pro Ala Pro Ala Pro Ala Pro Ala Pro
1               5                   10

<210> SEQ ID NO 34
<211> LENGTH: 12
<212> TYPE: PRT
<213> ORGANISM: Artificial Sequence
<220> FEATURE:
<223> OTHER INFORMATION: Synthetic Sequence
```

```
<400> SEQUENCE: 34

Ala Glu Ala Ala Ala Lys Glu Ala Ala Ala Lys Ala
1               5                   10

<210> SEQ ID NO 35
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 35

Ser Gly Gly Ser Gly Ser Ser
1               5

<210> SEQ ID NO 36
<211> LENGTH: 16
<212> TYPE: PRT
<213> ORGANISM: Artificial Sequence
<220> FEATURE:
<223> OTHER INFORMATION: Synthetic Sequence

<400> SEQUENCE: 36

Ser Gly Gly Ser Gly Gly Ser Gly Gly Ser Gly Gly Ser Gly Ser Ser
1               5                   10                  15

<210> SEQ ID NO 37
<211> LENGTH: 31
<212> TYPE: PRT
<213> ORGANISM: Artificial Sequence
<220> FEATURE:
<223> OTHER INFORMATION: Synthetic Sequence

<400> SEQUENCE: 37

Ser Gly Gly Ser Gly Gly Ser Gly Gly Ser Gly Gly Ser Gly Gly Ser
1               5                   10                  15

Gly Gly Ser Gly Gly Ser Gly Gly Ser Gly Gly Ser Gly Ser Ser
            20                  25                  30

<210> SEQ ID NO 38
<211> LENGTH: 29
<212> TYPE: PRT
<213> ORGANISM: Artificial Sequence
<220> FEATURE:
<223> OTHER INFORMATION: Synthetic Sequence

<400> SEQUENCE: 38

Gly Gly Ser Gly Gly Ser Gly Gly Ser Gly Gly Ser Gly Gly Ser Gly
1               5                   10                  15

Gly Ser Gly Gly Ser Gly Gly Ser Gly Gly Ser Gly Ser
            20                  25

<210> SEQ ID NO 39
<211> LENGTH: 585
<212> TYPE: PRT
<213> ORGANISM: Homo sapiens

<400> SEQUENCE: 39

Asp Ala His Lys Ser Glu Val Ala His Arg Phe Lys Asp Leu Gly Glu
1               5                   10                  15

Glu Asn Phe Lys Ala Leu Val Leu Ile Ala Phe Ala Gln Tyr Leu Gln
            20                  25                  30

Gln Cys Pro Phe Glu Asp His Val Lys Leu Val Asn Glu Val Thr Glu
```

```
            35                  40                  45
Phe Ala Lys Thr Cys Val Ala Asp Glu Ser Ala Glu Asn Cys Asp Lys
 50                  55                  60
Ser Leu His Thr Leu Phe Gly Asp Lys Leu Cys Thr Val Ala Thr Leu
 65                  70                  75                  80
Arg Glu Thr Tyr Gly Glu Met Ala Asp Cys Cys Ala Lys Gln Glu Pro
                 85                  90                  95
Glu Arg Asn Glu Cys Phe Leu Gln His Lys Asp Asp Asn Pro Asn Leu
            100                 105                 110
Pro Arg Leu Val Arg Pro Glu Val Asp Val Met Cys Thr Ala Phe His
        115                 120                 125
Asp Asn Glu Glu Thr Phe Leu Lys Lys Tyr Leu Tyr Glu Ile Ala Arg
    130                 135                 140
Arg His Pro Tyr Phe Tyr Ala Pro Glu Leu Leu Phe Phe Ala Lys Arg
145                 150                 155                 160
Tyr Lys Ala Ala Phe Thr Glu Cys Cys Gln Ala Ala Asp Lys Ala Ala
                165                 170                 175
Cys Leu Leu Pro Lys Leu Asp Glu Leu Arg Asp Glu Gly Lys Ala Ser
            180                 185                 190
Ser Ala Lys Gln Arg Leu Lys Cys Ala Ser Leu Gln Lys Phe Gly Glu
        195                 200                 205
Arg Ala Phe Lys Ala Trp Ala Val Ala Arg Leu Ser Gln Arg Phe Pro
    210                 215                 220
Lys Ala Glu Phe Ala Glu Val Ser Lys Leu Val Thr Asp Leu Thr Lys
225                 230                 235                 240
Val His Thr Glu Cys Cys His Gly Asp Leu Leu Glu Cys Ala Asp Asp
                245                 250                 255
Arg Ala Asp Leu Ala Lys Tyr Ile Cys Glu Asn Gln Asp Ser Ile Ser
            260                 265                 270
Ser Lys Leu Lys Glu Cys Cys Glu Lys Pro Leu Leu Glu Lys Ser His
        275                 280                 285
Cys Ile Ala Glu Val Glu Asn Asp Glu Met Pro Ala Asp Leu Pro Ser
    290                 295                 300
Leu Ala Ala Asp Phe Val Glu Ser Lys Asp Val Cys Lys Asn Tyr Ala
305                 310                 315                 320
Glu Ala Lys Asp Val Phe Leu Gly Met Phe Leu Tyr Glu Tyr Ala Arg
                325                 330                 335
Arg His Pro Asp Tyr Ser Val Val Leu Leu Leu Arg Leu Ala Lys Thr
            340                 345                 350
Tyr Glu Thr Thr Leu Glu Lys Cys Cys Ala Ala Ala Asp Pro His Glu
        355                 360                 365
Cys Tyr Ala Lys Val Phe Asp Glu Phe Lys Pro Leu Val Glu Glu Pro
    370                 375                 380
Gln Asn Leu Ile Lys Gln Asn Cys Glu Leu Phe Glu Gln Leu Gly Glu
385                 390                 395                 400
Tyr Lys Phe Gln Asn Ala Leu Leu Val Arg Tyr Thr Lys Lys Val Pro
                405                 410                 415
Gln Val Ser Thr Pro Thr Leu Val Glu Val Ser Arg Asn Leu Gly Lys
            420                 425                 430
Val Gly Ser Lys Cys Cys Lys His Pro Glu Ala Lys Arg Met Pro Cys
        435                 440                 445
Ala Glu Asp Tyr Leu Ser Val Val Leu Asn Gln Leu Cys Val Leu His
    450                 455                 460
```

```
Glu Lys Thr Pro Val Ser Asp Arg Val Thr Lys Cys Cys Thr Glu Ser
465                 470                 475                 480

Leu Val Asn Arg Arg Pro Cys Phe Ser Ala Leu Glu Val Asp Glu Thr
                485                 490                 495

Tyr Val Pro Lys Glu Phe Asn Ala Glu Thr Phe Thr Phe His Ala Asp
            500                 505                 510

Ile Cys Thr Leu Ser Glu Lys Glu Arg Gln Ile Lys Lys Gln Thr Ala
                515                 520                 525

Leu Val Glu Leu Val Lys His Lys Pro Lys Ala Thr Lys Glu Gln Leu
            530                 535                 540

Lys Ala Val Met Asp Asp Phe Ala Ala Phe Val Glu Lys Cys Cys Lys
545                 550                 555                 560

Ala Asp Asp Lys Glu Thr Cys Phe Ala Glu Glu Gly Lys Lys Leu Val
                565                 570                 575

Ala Ala Ser Gln Ala Ala Leu Gly Leu
            580                 585

<210> SEQ ID NO 40
<211> LENGTH: 625
<212> TYPE: PRT
<213> ORGANISM: Homo sapiens

<400> SEQUENCE: 40

Met Ile Phe Leu Tyr Gln Val Val His Phe Ile Leu Phe Thr Ser Val
1               5                   10                  15

Ser Gly Glu Cys Val Thr Gln Leu Leu Lys Asp Thr Cys Phe Glu Gly
                20                  25                  30

Gly Asp Ile Thr Thr Val Phe Thr Pro Ser Ala Lys Tyr Cys Gln Val
            35                  40                  45

Val Cys Thr Tyr His Pro Arg Cys Leu Leu Phe Thr Phe Thr Ala Glu
        50                  55                  60

Ser Pro Ser Glu Asp Pro Thr Arg Trp Phe Thr Cys Val Leu Lys Asp
65                  70                  75                  80

Ser Val Thr Glu Thr Leu Pro Arg Val Asn Arg Thr Ala Ala Ile Ser
                85                  90                  95

Gly Tyr Ser Phe Lys Gln Cys Ser His Gln Ile Ser Ala Cys Asn Lys
                100                 105                 110

Asp Ile Tyr Val Asp Leu Asp Met Lys Gly Ile Asn Tyr Asn Ser Ser
            115                 120                 125

Val Ala Lys Ser Ala Gln Glu Cys Gln Glu Arg Cys Thr Asp Asp Val
        130                 135                 140

His Cys His Phe Phe Thr Tyr Ala Thr Arg Gln Phe Pro Ser Leu Glu
145                 150                 155                 160

His Arg Asn Ile Cys Leu Leu Lys His Thr Gln Thr Gly Thr Pro Thr
                165                 170                 175

Arg Ile Thr Lys Leu Asp Lys Val Val Ser Gly Phe Ser Leu Lys Ser
            180                 185                 190

Cys Ala Leu Ser Asn Leu Ala Cys Ile Arg Asp Ile Phe Pro Asn Thr
        195                 200                 205

Val Phe Ala Asp Ser Asn Ile Asp Ser Val Met Ala Pro Asp Ala Phe
    210                 215                 220

Val Cys Gly Arg Ile Cys Thr His His Pro Gly Cys Leu Phe Phe Thr
225                 230                 235                 240

Phe Phe Ser Gln Glu Trp Pro Lys Glu Ser Gln Arg Asn Leu Cys Leu
```

```
                        245                 250                 255
Leu Lys Thr Ser Glu Ser Gly Leu Pro Ser Thr Arg Ile Lys Lys Ser
                    260                 265                 270

Lys Ala Leu Ser Gly Phe Ser Leu Gln Ser Cys Arg His Ser Ile Pro
                275                 280                 285

Val Phe Cys His Ser Ser Phe Tyr His Asp Thr Asp Phe Leu Gly Glu
            290                 295                 300

Glu Leu Asp Ile Val Ala Ala Lys Ser His Glu Ala Cys Gln Lys Leu
305                 310                 315                 320

Cys Thr Asn Ala Val Arg Cys Gln Phe Phe Thr Tyr Thr Pro Ala Gln
                325                 330                 335

Ala Ser Cys Asn Glu Gly Lys Gly Lys Cys Tyr Leu Lys Leu Ser Ser
                340                 345                 350

Asn Gly Ser Pro Thr Lys Ile Leu His Gly Arg Gly Gly Ile Ser Gly
                355                 360                 365

Tyr Thr Leu Arg Leu Cys Lys Met Asp Asn Glu Cys Thr Thr Lys Ile
                370                 375                 380

Lys Pro Arg Ile Val Gly Gly Thr Ala Ser Val Arg Gly Glu Trp Pro
385                 390                 395                 400

Trp Gln Val Thr Leu His Thr Thr Ser Pro Thr Gln Arg His Leu Cys
                405                 410                 415

Gly Gly Ser Ile Ile Gly Asn Gln Trp Ile Leu Thr Ala Ala His Cys
                420                 425                 430

Phe Tyr Gly Val Glu Ser Pro Lys Ile Leu Arg Val Tyr Ser Gly Ile
                435                 440                 445

Leu Asn Gln Ser Glu Ile Lys Glu Asp Thr Ser Phe Phe Gly Val Gln
450                 455                 460

Glu Ile Ile Ile His Asp Gln Tyr Lys Met Ala Glu Ser Gly Tyr Asp
465                 470                 475                 480

Ile Ala Leu Leu Lys Leu Glu Thr Thr Val Asn Tyr Thr Asp Ser Gln
                485                 490                 495

Arg Pro Ile Cys Leu Pro Ser Lys Gly Asp Arg Asn Val Ile Tyr Thr
                500                 505                 510

Asp Cys Trp Val Thr Gly Trp Gly Tyr Arg Lys Leu Arg Asp Lys Ile
                515                 520                 525

Gln Asn Thr Leu Gln Lys Ala Lys Ile Pro Leu Val Thr Asn Glu Glu
                530                 535                 540

Cys Gln Lys Arg Tyr Arg Gly His Lys Ile Thr His Lys Met Ile Cys
545                 550                 555                 560

Ala Gly Tyr Arg Glu Gly Gly Lys Asp Ala Cys Lys Gly Asp Ser Gly
                565                 570                 575

Gly Pro Leu Ser Cys Lys His Asn Glu Val Trp His Leu Val Gly Ile
                580                 585                 590

Thr Ser Trp Gly Glu Gly Cys Ala Gln Arg Glu Arg Pro Gly Val Tyr
                595                 600                 605

Thr Asn Val Val Glu Tyr Val Asp Trp Ile Leu Glu Lys Thr Gln Ala
                610                 615                 620

Val
625

<210> SEQ ID NO 41
<211> LENGTH: 638
<212> TYPE: PRT
<213> ORGANISM: Homo sapiens
```

<400> SEQUENCE: 41

```
Met Ile Leu Phe Lys Gln Ala Thr Tyr Phe Ile Ser Leu Phe Ala Thr
1               5                   10                  15

Val Ser Cys Gly Cys Leu Thr Gln Leu Tyr Glu Asn Ala Phe Phe Arg
            20                  25                  30

Gly Gly Asp Val Ala Ser Met Tyr Thr Pro Asn Ala Gln Tyr Cys Gln
        35                  40                  45

Met Arg Cys Thr Phe His Pro Arg Cys Leu Leu Phe Ser Phe Leu Pro
    50                  55                  60

Ala Ser Ser Ile Asn Asp Met Glu Lys Arg Phe Gly Cys Phe Leu Lys
65                  70                  75                  80

Asp Ser Val Thr Gly Thr Leu Pro Lys Val His Arg Thr Gly Ala Val
                85                  90                  95

Ser Gly His Ser Leu Lys Gln Cys Gly His Gln Ile Ser Ala Cys His
            100                 105                 110

Arg Asp Ile Tyr Lys Gly Val Asp Met Arg Gly Val Asn Phe Asn Val
        115                 120                 125

Ser Lys Val Ser Ser Val Glu Glu Cys Gln Lys Arg Cys Thr Asn Asn
130                 135                 140

Ile Arg Cys Gln Phe Phe Ser Tyr Ala Thr Gln Thr Phe His Lys Ala
145                 150                 155                 160

Glu Tyr Arg Asn Asn Cys Leu Leu Lys Tyr Ser Pro Gly Gly Thr Pro
                165                 170                 175

Thr Ala Ile Lys Val Leu Ser Asn Val Glu Ser Gly Phe Ser Leu Lys
            180                 185                 190

Pro Cys Ala Leu Ser Glu Ile Gly Cys His Met Asn Ile Phe Gln His
        195                 200                 205

Leu Ala Phe Ser Asp Val Asp Val Ala Arg Val Leu Thr Pro Asp Ala
210                 215                 220

Phe Val Cys Arg Thr Ile Cys Thr Tyr His Pro Asn Cys Leu Phe Phe
225                 230                 235                 240

Thr Phe Tyr Thr Asn Val Trp Lys Ile Glu Ser Gln Arg Asn Val Cys
                245                 250                 255

Leu Leu Lys Thr Ser Glu Ser Gly Thr Pro Ser Ser Ser Thr Pro Gln
            260                 265                 270

Glu Asn Thr Ile Ser Gly Tyr Ser Leu Leu Thr Cys Lys Arg Thr Leu
        275                 280                 285

Pro Glu Pro Cys His Ser Lys Ile Tyr Pro Gly Val Asp Phe Gly Gly
        290                 295                 300

Glu Glu Leu Asn Val Thr Phe Val Lys Gly Val Asn Val Cys Gln Glu
305                 310                 315                 320

Thr Cys Thr Lys Met Ile Arg Cys Gln Phe Phe Thr Tyr Ser Leu Leu
                325                 330                 335

Pro Glu Asp Cys Lys Glu Glu Cys Lys Cys Phe Leu Arg Leu Ser
            340                 345                 350

Met Asp Gly Ser Pro Thr Arg Ile Ala Tyr Gly Thr Gln Gly Ser Ser
        355                 360                 365

Gly Tyr Ser Leu Arg Leu Cys Asn Thr Gly Asp Asn Ser Val Cys Thr
        370                 375                 380

Thr Lys Thr Ser Thr Arg Ile Val Gly Gly Thr Asn Ser Ser Trp Gly
385                 390                 395                 400

Glu Trp Pro Trp Gln Val Ser Leu Gln Val Lys Leu Thr Ala Gln Arg
```

```
                    405                 410                 415
His Leu Cys Gly Gly Ser Leu Ile Gly His Gln Trp Val Leu Thr Ala
                420                 425                 430

Ala His Cys Phe Asp Gly Leu Pro Leu Gln Asp Val Trp Arg Ile Tyr
            435                 440                 445

Ser Gly Ile Leu Asn Leu Ser Asp Ile Thr Lys Asp Thr Pro Phe Ser
        450                 455                 460

Gln Ile Lys Glu Ile Ile His Gln Asn Tyr Lys Val Ser Glu Gly
465                 470                 475                 480

Asn His Asp Ile Ala Leu Ile Lys Leu Gln Ala Pro Leu Asn Tyr Thr
                485                 490                 495

Glu Phe Gln Lys Pro Ile Cys Leu Pro Ser Lys Gly Asp Thr Ser Thr
            500                 505                 510

Ile Tyr Thr Asn Cys Trp Val Thr Gly Trp Gly Phe Ser Lys Glu Lys
        515                 520                 525

Gly Glu Ile Gln Asn Ile Leu Gln Lys Val Asn Ile Pro Leu Val Thr
    530                 535                 540

Asn Glu Glu Cys Gln Lys Arg Tyr Gln Asp Tyr Lys Ile Thr Gln Arg
545                 550                 555                 560

Met Val Cys Ala Gly Tyr Lys Glu Gly Gly Lys Asp Ala Cys Lys Gly
                565                 570                 575

Asp Ser Gly Gly Pro Leu Val Cys Lys His Asn Gly Met Trp Arg Leu
            580                 585                 590

Val Gly Ile Thr Ser Trp Gly Glu Gly Cys Ala Arg Arg Glu Gln Pro
        595                 600                 605

Gly Val Tyr Thr Lys Val Ala Glu Tyr Met Asp Trp Ile Leu Glu Lys
    610                 615                 620

Thr Gln Ser Ser Asp Gly Lys Ala Gln Met Gln Ser Pro Ala
625                 630                 635

<210> SEQ ID NO 42
<211> LENGTH: 25
<212> TYPE: PRT
<213> ORGANISM: Artificial Sequence
<220> FEATURE:
<223> OTHER INFORMATION: Synthetic Sequence

<400> SEQUENCE: 42

Cys Thr Thr Lys Ile Lys Pro Arg Ile Val Gly Gly Thr Ala Ser Val
1               5                   10                  15

Arg Gly Glu Trp Pro Trp Gln Val Thr
            20                  25

<210> SEQ ID NO 43
<211> LENGTH: 13
<212> TYPE: PRT
<213> ORGANISM: Artificial Sequence
<220> FEATURE:
<223> OTHER INFORMATION: Synthetic Sequence

<400> SEQUENCE: 43

Gly Gly Gly Gly Ser Pro Arg Ile Gly Gly Gly Gly Ser
1               5                   10

<210> SEQ ID NO 44
<211> LENGTH: 26
<212> TYPE: PRT
<213> ORGANISM: Artificial Sequence
<220> FEATURE:
```

<223> OTHER INFORMATION: Synthetic Sequence

<400> SEQUENCE: 44

Val Cys Thr Thr Lys Thr Ser Thr Arg Ile Val Gly Gly Thr Asn Ser
1               5                   10                  15

Ser Trp Gly Glu Trp Pro Trp Gln Val Ser
            20                  25

<210> SEQ ID NO 45
<211> LENGTH: 7
<212> TYPE: PRT
<213> ORGANISM: Artificial Sequence
<220> FEATURE:
<223> OTHER INFORMATION: Synthetic Sequence

<400> SEQUENCE: 45

Ser Thr Arg Ile Val Gly Gly
1               5

<210> SEQ ID NO 46
<211> LENGTH: 81
<212> TYPE: PRT
<213> ORGANISM: Saccharomyces cerevisiae

<400> SEQUENCE: 46

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Ser Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser

<210> SEQ ID NO 47
<211> LENGTH: 24
<212> TYPE: PRT
<213> ORGANISM: Homo sapiens

<400> SEQUENCE: 47

Met Lys Trp Val Thr Phe Ile Ser Leu Leu Phe Leu Phe Ser Ser Ala
1               5                   10                  15

Tyr Ser Arg Gly Val Phe Arg Arg
            20

<210> SEQ ID NO 48
<211> LENGTH: 20
<212> TYPE: PRT
<213> ORGANISM: Homo sapiens

<400> SEQUENCE: 48

Met Ser Arg Glu Leu Ala Pro Leu Leu Leu Leu Leu Leu Ser Ile His
1               5                   10                  15

Ser Ala Leu Ala
            20

ENGINEERING OF DNASE ENZYMES FOR MANUFACTURING AND THERAPY

RELATED APPLICATIONS

The present application claims the benefit of, and priority to, US Provisional Application No. 62/742,682 filed Oct. 8, 2018; 62/775,563 filed Dec. 5, 2018; 62/779,104 filed Dec. 13, 2018; U.S. Pat. No. 62,808,601 filed Feb. 21, 2019; and 62/846,904 filed May 13, 2019, the contents of which are hereby incorporated by reference in their entireties.

FIELD OF THE INVENTION

This invention relates to the field of engineered DNASE enzymes.

BACKGROUND

Inflammation is an essential host response to control invading microbes and heal damaged tissues. Uncontrolled and persistent inflammation causes tissue injury in a plethora of inflammatory disorders. Neutrophils are the predominant leukocytes in acute inflammation. During infections, neutrophils generate neutrophil extracellular traps (NETs), lattices of DNA-filaments decorated with toxic histones and enzymes that immobilize and neutralize bacteria. However, inappropriately released NETs may harm host cells due to their cytotoxic, proinflammatory, and prothrombotic activity.

DNASE1 (D1) forms along with DNASE1-LIKE 1 (D1L1), DNASE1-LIKE 2 (D1L2) and DNASE1-LIKE 3 (D1L3), the DNASE1-protein family, a group of homologous secreted DNase enzymes. DNASE2A and DNASE2B form an additional group of homologous extracellular DNase enzymes. DNASE1- and DNASE2-protein family members are evolutionary conserved and expressed in various species, including humans. Recombinant human DNASE1- and DNASE2-protein family members provide drug candidates for NET-associated diseases. While D1 has been developed for some therapeutic applications in patients, the conditions for large-scale manufacturing of the other members of the DNASE1-protein family have not been described. Furthermore, the physical, enzymatic, and pharmacokinetic properties of these enzymes are not ideal for clinical applications. Thus, there is a need for defining a manufacturing process for D1L1, D1L2, and D1L3 enzymes, and for engineering DNases for use in therapy, including for degrading NETs.

SUMMARY OF THE DISCLOSURE

The present invention provides engineered human extracellular DNASE proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by extracellular DNA, extracellular chromatin, and neutrophil extracellular trap (NET) accumulation and/or release. In accordance with aspects of the invention, the DNase variants described herein are more suitable for therapy and/or more amenable to large-scale manufacturing. In some embodiments, the DNase variants described herein have benefits for medical therapy, including systemic therapy. Such benefits include slower drug elimination, e.g., increased circulatory half-life (e.g., serum half-life), an extended duration of pharmacodynamic activity, high chromatin-degrading activity, and protease resistance.

In some aspects, the invention provides a D1L3 variant, wherein the D1L3 variant has one or more of increased protein stability, slower drug elimination and increased duration of pharmacodynamic activity, resistance to proteolytic degradation, higher production levels with in vitro expression systems, better suitability for purification, and not substantially less, the same, or better chromatin and/or NET-degrading activity as compared to wild-type D1L3 Isoform 1 enzyme of SEQ ID NO:4 or wild-type D1L3 Isoform 2 enzyme of SEQ ID NO:5.

In some embodiments, the D1L3 variant is a fusion protein that comprises an amino acid sequence that is at least 80% identical to the mature enzyme defined by SEQ ID NO:4 or SEQ ID NO:5, an albumin amino acid sequence at the N-terminus of the mature enzyme, and optionally a linking amino acid sequence between the albumin amino acid sequence (the albumin domain) and the D1L3 amino acid sequence (the D1L3 domain). In these embodiments, the D1L3 exhibits slower elimination (e.g., improved circulatory half-life or serum half-life) and an extended duration of pharmacodynamic activity, including for systemic therapy. In some embodiments, the fusion of albumin with linking sequence to the D1L3 domain does not substantially impact chromatin-degrading activity of the enzyme (e.g., a measured using an in vitro assay) as compared to the enzyme without an albumin fusion.

In these embodiments, the D1L3 domain of the fusion protein has a deletion of all or part of the C-terminal basic domain that is present in the wild-type D1L3 enzyme. Deletion or inactivation of the C-terminal basic domain substantially improves chromatin degrading activity. That is, removal of the C-terminal basic domain (BD) activates the wild-type D1L3 enzyme for degrading chromatin.

In some embodiments, the D1L3 variant has one or more building block substitutions from D1. For example, the D1L3 variant may have the building block substitution of Q282_S305delinsK, which includes a deletion of the C-terminal basic domain, which domain is absent in D1. In some embodiments, the D1L3 variant has an amino acid substitution at the position corresponding to position 101 of SEQ ID NO:4. The substitution can be Arg based on the corresponding building block from D1, or in some embodiments is Lys. Substitutions at this position can enhance chromatin-degrading activity of a D1L3 variant.

The linker where present may be a flexible linker, a rigid linker, or a physiologically-cleavable linker, such as a protease-cleavable linker. For example, the linker may be a hydrophilic amino acid sequence, and may be predominately constructed from amino acids selected from Gly, Ala, Ser, Thr, and Pro. In some embodiments, the variant is a flexible linker that is predominately glycine and serine residues (e.g., $(G_yS)_n$ linkers, where y is from 1 to 5, and n is from 1 to 20). In some embodiments, the linker is an α-helical linker. In some embodiments, the linker has at least 15 amino acids, or at least 25 amino acids. In various embodiments, longer linkers of at least 15 amino acids can provide improvements in yield upon expression in mammalian and non-mammalian expression systems, such as CHO cells or *Pichia pastoris*. Further, and surprisingly, longer linker sequences showed improved chromatin-degrading activity in an in vitro chromatin-degrading assay, as compared to shorter linker sequences.

In various embodiments, the D1L3 variant comprises the amino acid sequence of any one of SEQ ID NOS: 17 to 30, in each case optionally having from one to twenty amino acid modifications independently selected from insertions, deletions, or substitutions. These sequences provide exemplary fusion proteins between D1L3 (or D1L3 variants) with albumin sequences, including with various linker designs. In some embodiments, the amino acid modifications are in the D1L3 domain, the albumin domain, or both domains. In some embodiments, the variant has the amino acid sequence of SEQ ID NO: 19, SEQ ID NO: 22, SEQ ID NO: 26, SEQ ID NO: 27, SEQ ID NO: 28, SEQ ID NO: 29, or SEQ ID NO: 30. In these embodiments, the D1L3 variant comprises, in order from N-terminus to C-terminus: an albumin amino acid sequence, an intermediate or long flexible linker, and a D1L3 amino acid sequence (i.e., including D1L3 variants). SEQ ID NO: 28 further comprises an albumin fusion at the C-terminus through a long flexible peptide linker.

In other embodiments, the linker is cleavable by a protease, such as a coagulation pathway protease, such as activated Factor XII. In certain embodiments, the linker contains amino acid sequence of Factor XI and/or prekallikrein. In other embodiments, the linker includes a peptide sequence that is targeted for cleavage by a neutrophil specific protease, such as neutrophil elastase, cathepsin G, or proteinase 3.

In some aspects, the invention provides variants of extracellular DNASE enzymes engineered to have advantages in manufacturing, providing for production of the recombinant enzyme suitable for use in therapy. In various embodiments, the invention provides a recombinant D1, D1L1, D1L2, and D1L3 variant comprising one or more amino acid substitutions in cysteine residues (or PEGylation of Cys residues) resulting in reduced intra- and inter-molecular cross-linking via disulfide bridges during protein expression.

In other aspects, the invention provides variants of extracellular DNASE enzymes engineered to have advantages in protease resistance, for improving in vivo exposure, e.g., slowing elimination, e.g. extending half-life (e.g., serum half-life), and extending duration of pharmacodynamic activity, as well as reducing proteolysis during recombinant enzyme production. This disclosure identifies, for example, D1L3 residues that are sensitive to proteolysis by plasmin, thrombin, and/or trypsin, as well as residues (e.g., paired basic amino acids) that are sensitive to proteases produced by mammalian and non-mammalian cell lines. Engineered mutation of these residues can confer these advantages in protease resistance.

In other aspects, the invention provides a method for recombinant production of extracellular DNASE proteins, including variants thereof described herein. In some embodiments, the method employs a non-mammalian expression system, e.g., a eukaryotic non-mammalian expression system, such as *Pichia pastoris*. In some embodiments, the *Pichia pastoris* encodes the DNase enzyme with its native signal peptide allowing for secretion from host cells. In some embodiments, the expression system is a mammalian cell expression system, such as Chinese Hamster Ovary (CHO) cells.

In some embodiments, the recombinant expression system has a deletion or inactivation of one or more proteases that cleave at paired basic amino acids. Exemplary enzymes include Furin (expressed by CHO cells) and Aspartic proteinase 3 (Ysp1) and Kexin (Kex2) expressed by *Pichia pastoris*. In some embodiments, these enzymes are not genetically deleted or inactivated, but their activity is inhibited with a protease inhibitor during recombinant protein production.

In some embodiments, the growth medium for the non-mammalian expression system or mammalian expression system is supplemented with polyanions such as dextran sulfate, heparins, ferric citrate, and EDTA. In further embodiments, the growth medium of *Pichia pastoris* or other expression system is supplemented with dextran sulfate that has an average molecular weight of between 5 kDa and 100 kDa. For example, the polyanion may be added to the culture in an amount sufficient to complex with the recombinant protein produced. In some embodiments, the recombinant extracellular DNASE proteins and variants thereof from the culture medium of non-mammalian expression system or mammalian expression system, are purified through a method that includes the dissociation of recombinant extracellular DNASE proteins and variants from polyanions such as dextran sulfate, heparins, and EDTA.

In other aspects, the invention provides isolated polynucleotides encoding the D1, D1L1, D1L2, or D1L3 variants, as well as vectors and host cells. Polynucleotides may be encoding mRNA or DNA. Host cells can be cells of a recombinant expression system, including bacterial or eukaryotic, whether non-mammalian such as *Pichia pastoris*, or mammalian such as CHO cells. In other embodiments, the host cell can be delivered for DNASE therapy. For example, the invention in some embodiments provides host cells, e.g., human cells, e.g., white blood cells, modified to secrete one or more of the extracellular DNASE proteins described herein, and intended for administration as a therapeutic agent.

The invention further provides pharmaceutical compositions comprising the extracellular DNASE protein or variant thereof as described herein, or optionally the polynucleotide or the vector as described, and a pharmaceutically acceptable carrier. The pharmaceutical composition may be formulated for any administration route.

In other aspects, the invention provides a method for treating a subject in need of extracellular DNA degradation, extracellular chromatin degradation, extracellular trap (ET) degradation and/or neutrophil extracellular trap (NET) degradation, by administering a therapeutically effective amount of the extracellular DNASE or variant thereof or composition described herein.

Other aspects and embodiments of the invention will be apparent from the following detailed description.

DESCRIPTION OF FIGURES

FIGS. 6A-C illustrate the use of anion exchange surface and cation exchange surface for affinity purification of dextran sulfate-complexed D1L3. FIG. 6A shows that polyanions, such as dextran sulfate (DS), form a complex with D1L3. The D1L3-DS-complex prevents the interaction and scavenging of D1L3 by negatively charged surfaces during the production process. FIG. 6B and FIG. 6C show the two-step purification process of D1L3 from DS-D1L3-complexes.

FIG. 7 lists trypsin cleavage site mutation strategies to limit D1L3 degradation.

FIG. 9 illustrates plasmin cleavage site mutation strategies to limit D1L3 degradation.

FIG. 11 lists plasmin cleavage sites based on plasmin digestion and shows mutation strategies to limit D1L3 degradation.

FIGS. 12A-B show that D1L3 has a propensity to misfold when expressed in CHO cells. FIG. 12A illustrates a simple expression vector for D1L3 expression using the native secretory signal peptide. Supernatants of stable pools were analyzed by Western Blot using an anti-DNASE1L3 antibody, and FIG. 12B shows the presence of high molecular weight aggregates under non-reducing conditions, which are resolved under reducing conditions.

FIG. 14 lists the cysteine residues in D1L3, and shows mutation strategies to limit high molecular weight aggregates during protein expression.

FIGS. 16A-B illustrate the expression of D1L3 in *Pichia pastoris* using either the native secretory signal or α-mating factor from *Saccharomyces cerevisiae* (αMF). FIG. 16A shows that the N-terminus of D1L3 was led by the alpha-mating factor (aMF) pre-pro secretion leader from *Saccharomyces cerevisiae*. FIG. 16B shows that the secretory signal from αMF resulted in glycosylation and non-processing of the signal peptide.

FIGS. 17A-C illustrate that a fusion construct of αMF, human serum albumin (HSA), linker sequence, and D1L3 is not glycosylated in *P. pastoris* expression system, and retains chromatin-degrading activity. FIG. 17A shows the fusion construct with αMF, human serum albumin (HSA), linker sequence, and D1L3. FIG. 17B shows that the fusion construct is not glycosylated in *P. pastoris* expression system, and FIG. 17C shows that the fusion construct retains chromatin-degrading activity.

FIG. 18 illustrates the expression levels human serum albumin (HSA) fusion constructs of Basic Domain Deleted-DNASE1L3 (BDD-D1L3) or wild-type DNASE1L3 (D1L3) in *Pichia pastoris*. The HSA is fused either to the N- or C-terminus of BDD-D1L3 or D1L3. Two linker sequences, L1 and L2, were placed between HSA and BDD-D1L3 or D1L3.

FIG. 19 illustrates the expression levels human serum albumin (HSA) fusion constructs of wild-type DNASE1L3 (D1L3) in *Pichia pastoris*. The HSA is fused to the N-terminus of D1L3. Three different linker sequences (L2, L3, L4) were placed between HSA and D1L3.

FIG. 21A shows that Dnase1$^{-/-}$Dnase1l3$^{-/-}$ mice injected with SED ID NO: 14 and SEQ ID NO: 19 show similar chromatin degrading activity in serum. FIG. 21B shows that SEQ ID NO: 19 has a circulation half-life of 3.3 days in mice expressing the human FcRn receptor.

FIG. 22 illustrates the expression levels and chromatin degrading activity of human serum albumin (HSA) fusion constructs of Basic Domain Deleted-DNASE1L3 (BDD-D1L3) produced in *Pichia pastoris*. The HSA is fused to the N-terminus and C-terminus of BDD-D1L3. Two different linker sequences (L7 and L8) were placed between HSA and BDD-D1L3.

FIG. 23A shows a fusion construct with HSA and a linker. FIG. 23B shows a linker cleavable by Factor XIIa. The sequences of a linker containing a human Factor XI sequence (SEQ ID NO: 42) and a linker containing a human prekallikrein (SEQ ID NO: 44) are shown.

DESCRIPTION OF THE INVENTION

Figure 1:
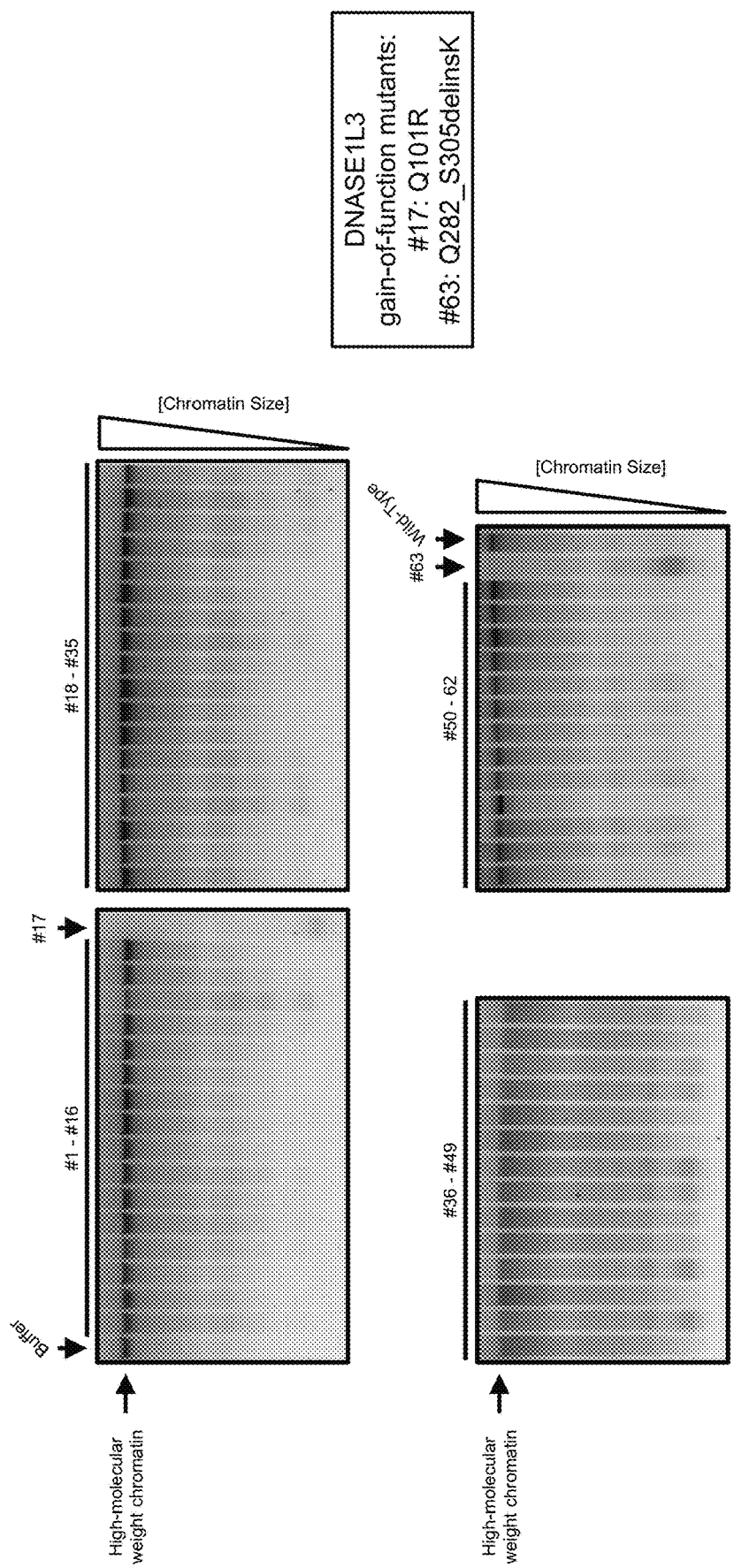
FIG. 1 illustrates that the mutations Q101R and Q282_S305delinsK in SEQ ID NO: 4 increase the activity to degrade high-molecular weight chromatin of DNASE1L3. CHO cells were transiently transfected with wild-type DNASE1L3 or DNASE1L3 with building block substitutions. Supernatants of transfected cells were incubated with purified nuclei (high-molecular weight chromatin) or buffer. DNA was isolated and analyzed by agarose gel electrophoresis. The figure shows the agarose gel stained with a DNA dye.

The present invention provides candidates of engineered human extracellular DNASE proteins (e.g., variants of DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)) that are useful for treating conditions characterized by extracellular DNA, extracellular chromatin, and neutrophil extracellular trap (NET) accumulation and/or release. In accordance with aspects of the invention, the DNase variants described herein are more suitable and/or effective for therapy and/or are more amenable to large-scale manufacturing. In some embodiments, the DNase variants described herein have benefits for systemic therapy. Such benefits include longer exposure (e.g., slower elimination, longer circulatory half-life), extended duration of pharmacodynamic action, improved chromatin-degrading activity, and protease resistance.

Definitions

As used herein and in the claims, the singular forms "a," "an," and "the" include the singular and the plural reference unless the context clearly indicates otherwise. Thus, for example, a reference to "an agent" includes a single agent and a plurality of such agents.

The term "chromatinase" refers to a class of deoxyribonuclease enzyme that exhibits more than a negligible ability to cut, cleave or digest chromatin, i.e., DNA associated with one or more histone proteins. Human DNASE1L3 is a chromatinase. Generally, the various DNASE1L3 variants disclosed herein are chromatinases. Not all DNASE enzymes are chromatinases. For example, human DNASE1 has essentially no ability to cut, cleave, or digest chromatin and is not a chromatinase.

As used herein with reference to a drug, "half-life" refers to the elimination half-life of the concentration of the drug in an animal, as measured in a matrix of interest, e.g., serum or plasma. The skilled person will understand that not all drugs exhibit first-order kinetics or do so during all phases of elimination. In such cases, the skilled person will understand that the terms "half-life extension" or "extended half-life" are expressions that refer to a slower rate of elimination.

"Isolated" means altered or removed from the natural state. For example, a nucleic acid or a peptide naturally present in a living animal is not "isolated," but the same nucleic acid or peptide partially or completely separated from the coexisting materials of its natural state is "isolated." An isolated nucleic acid or protein can exist in substantially purified form, or can exist in a non-native environment such as, for example, a host cell.

As used herein, "neutrophil extracellular trap" and the acronym "NET" refer to a network of extracellular fibers comprising nuclear contents, e.g., DNA bound to histone proteins that are released from an immune cell, typically a neutrophil, in a programmed fashion.

Unless otherwise specified, a "nucleotide sequence or nucleic acid encoding an amino acid sequence" includes all nucleotide sequences that are degenerate versions of each other and that encode the same amino acid sequence. The phrase nucleotide sequence that encodes a protein or an RNA may also include introns to the extent that the nucleotide sequence encoding the protein may in some version contain an intron(s).

The terms "about" and "approximately" include an amount that is ±10% of an associated numerical value.

The term "extracellular DNASE" refers to extracellular DNASE proteins of the DNASE1- and DNASE2-family (e.g., DNASE1 (D1), DNASE1-LIKE 1 (D1L1), DNASE1-LIKE 2 (D1L2), DNASE1-LIKE 3 Isoform 1 (D1L3), DNASE1-LIKE 3 Isoform 2 (D1L3-2), DNASE2A (D2A), and DNASE2B (D2B)).

In some aspects and embodiments, the extracellular DNASE or variant thereof is fused, optionally by means of an interposed linker, to a half-life extending moiety, such as albumin, transferrin, an Fc, or elastin-like protein, or a variant thereof. See, e.g., U.S. Pat. No. 9,458,218, which is hereby incorporated by reference in its entirety. In some embodiments, the extracellular DNASE or variant thereof is dimerized by an immunoglobulin hinge region. For example, the engineered enzymes described herein may also include an Fc-fusion domain (e.g., a hinge and CH2 domains and CH3 domains of an immunoglobulin). In some embodiments, the DNASE (e.g., D1L3 variant) is fused to an albumin amino acid sequence or domain, e.g., human albumin or a fragment or variant thereof. See, for example, WO 2015/066550 and U.S. Pat. No. 9,221,896, which are hereby incorporated by reference in their entirety. Albumin can be joined to the DNASE, optionally with an interposed linker, at the N-terminus and/or the C-terminus of the engineered extracellular DNASE or variant thereof. An exemplary albumin amino acid sequence is provided by SEQ ID NO: 39. In some embodiments, D1L3 and D1, or variants as described herein, are together dimerized by an Fc hinge region, creating a dimeric molecule with synergistic functional properties for degrading NETs. In some embodiments, the extracellular DNASE or variant thereof is fused at the N-terminus to an albumin amino acid sequence, through a peptide linker. The peptide linker may be a flexible linker, a rigid linker, or in some embodiments a physiologically-cleavable linker (e.g., a protease-cleavable linker). In some embodiments, the linker is 5 to 100 amino acids in length, or is 5 to 50 amino acids in length. In still other embodiments, the linker is an organic molecule, group, polymer (e.g., PEG), or chemical moiety that is covalently coupled to the extracellular DNASE and half-life extending moiety (e.g., albumin).

In some aspects, the invention provides a D1L3 variant, wherein the D1L3 variant has one or more of increased protein stability, increased pharmacokinetic exposure and duration of pharmacodynamic activity, resistance to proteolytic degradation, higher production levels with in vitro expression systems, better suitability for purification, and not substantially less, the same, or better chromatin and/or NET-degrading activity as compared to wild-type D1L3 Isoform 1 enzyme of SEQ ID NO:4 or wild-type D1L3 Isoform 2 enzyme of SEQ ID NO:5. As used herein, unless stated to the contrary, the term "D1L3" includes either Isoform 1 or Isoform 2.

The DNA- and/or chromatin- and/or NET-degrading activity of an enzyme, e.g. a D1L3 variant, can be measured in vitro, for example by incubation of the enzyme with DNA, chromatin, or NETs, obtained, e.g., from purified nuclei, DNA, or ex vivo blood or neutrophils induced to form NETs. Alternatively, the DNA- and/or chromatin- and/or NET-degrading activity of an enzyme, e.g. a D1L3 variant, can be measured in vivo, for example by administering the enzyme to a subject, wherein the subject produces or is induced to produce extracellular DNA, chromatin, or NETs, and measuring the effect of the enzyme on concentrations of DNA, chromatin, or NET levels in a matrix, e.g. serum, preferably with a parallel negative control, or by temporally comparing the concentrations before and after administration of the enzyme.

In some embodiments, the D1L3 variant has approximately the same chromatin- and/or NET-degrading activity as compared to wild-type D1L3 Isoform 1 enzyme of SEQ ID NO:4 or wild-type D1L3 Isoform 2 enzyme of SEQ ID NO:5. In some embodiments, D1L3 variant has higher chromatin- and/or NET-degrading activity as compared to wild-type D1L3 Isoform 1 enzyme of SEQ ID NO:4 or wild-type D1L3 Isoform 2 enzyme of SEQ ID NO:5.

In some embodiments, the D1L3 variant is a fusion protein comprising an albumin domain, an optional linker, and a D1L3 domain. In some embodiments, the albumin domain and optional linker are located on the N-terminal side of the D1L3 domain. In some embodiments, the albumin domain and optional linker are located on the C-terminal side of the D1L3 domain. In all such embodiments, the optional linker is interposed between the albumin domain and the D1L3 domain.

In some embodiments, the albumin amino acid sequence or domain of the fusion protein is at least about 75%, or at least about 80%, or at least about 85%, at least 90%, at least 95%, at least 97%, at least 98%, or at least 99% identical to the reference albumin sequence defined by SEQ ID NO: 39. In some embodiments, the albumin amino acid sequence or domain comprises or consists of the reference albumin sequence defined by SEQ ID NO:39. In various embodiments, the albumin amino acid sequence binds to the neonatal Fc receptor (FcRn), e.g., human FcRn. The albumin amino acid sequence may be a variant of wild-type HSA (e.g., as represented by SEQ ID NO: 39). In various embodiments, albumin variants may have from one to twenty, or from one to ten amino acid modifications independently selected from deletions, substitutions, and insertions with respect to SEQ ID NO: 39. In some embodiments, the albumin amino acid sequence is any mammalian albumin amino acid sequence.

In some embodiments, the albumin amino acid sequence or domain is a fragment of full-length albumin, as represented by SEQ ID NO: 39. The term "fragment," when used in the context of albumin, refers to any fragment of full-length albumin or a variant thereof (as described above) that extends the half-life of a DNASE enzyme to which it is fused or conjugated, relative to the corresponding non-fused DNASE. In some embodiments, a fragment of an albumin can refer to an amino acid sequence comprising a fusion of multiple domains of albumin (see, e.g., WO2011/124718), such as domains I and III, and domains II and III. Generally, a fragment of albumin has at least about 100 amino acids or at least about 200 or at least about 300 amino acids of the full-length sequence. In various embodiments, the albumin fragment maintains the ability to bind human FcRn.

In some embodiments, the D1L3-like domain of the fusion protein is at least about 85%, or at least about 90%, or at least about 95%, at least about 97%, or at least about 98%, or at least about 99% identical to the mature D1L3 enzyme reference sequence defined by SEQ ID NO:4 or SEQ ID NO:5. In some embodiments, the D1L3 domain comprises or consists of the reference sequence defined by SEQ ID NO:4 or SEQ ID NO:5. In some embodiments, the reference sequence does not include the C-terminal basic domain of SEQ ID NO: 4 or 5 defined by the C-terminal 23 amino acids.

In some embodiments, the fusion protein comprises an D1L3 domain, wherein the amino acid sequence of the D1L3 domain is at least about 80% identical to the mature enzyme defined by SEQ ID NO:4 or SEQ ID NO:5. The fusion protein can further comprise the albumin amino acid sequence or domain at the N-terminus of the mature enzyme, and a linking amino acid sequence between the albumin amino acid sequence and the amino acid sequence of the mature enzyme. In some embodiments, the D1L3 domain comprises an amino acid sequence that is at least about 90% identical to the mature enzyme reference sequence defined by SEQ ID NO:4 or SEQ ID NO:5. In some embodiments, the reference sequence does not include the C-terminal basic domain of SEQ ID NO: 4 or 5 defined by the C-terminal 23 amino acids. The fusion protein comprising the D1L3 domain exhibits improved circulatory half-life and duration of pharmacodynamic effect, including for systemic therapy. In addition, the fusion of albumin with linking sequence does not substantially impact (or in some embodiments does not have any negative impact on) chromatin-degrading activity as determined using an in vitro chromatin-degrading assay, as compared to the variant without an albumin fusion.

When referring to sequence identity with wild-type DNase enzymes, and unless stated otherwise, sequences refer to mature enzymes lacking the signal peptide. Further, unless stated otherwise, amino acid positions are numbered with respect to the full-translated DNase sequence, including signal peptide, for clarity. Accordingly, for example, reference to sequence identity to the enzyme of SEQ ID NO:4 (human D1L3, Isoform 1) refers to a percent identity with the mature enzyme having M21 at the N-terminus. Similarly, reference to sequence identity to the enzyme of SEQ ID NO:1 (human D1) refers to a percent identity with the mature enzyme having L23 at the N-terminus.

In some embodiments, the D1L3 has a deletion of all or part of the C-terminal basic domain. The C-terminal basic domain is defined as the C-terminal 23 amino acids of SEQ ID NO:4 or SEQ ID NO:5. Deletion or inactivation of the C-terminal basic domain of D1L3 substantially improves chromatin degrading activity. See FIGS. 1, 2, and 4. In some embodiments, the D1L3 variant has a deletion of C-terminal basic domain amino acids, such as at least 5 amino acids, or in some embodiments at least 10 amino acids, or in some embodiments at least 15 amino acids, or in some embodiments at least 20 amino acids of the C-terminal basic domain. In some embodiments, the D1L3 variant has a deletion of the entire C-terminal basic domain defined by the C-terminal 23 amino acids of SEQ ID NO:4 or SEQ ID NO:5. Exemplary BD deletions include Q282_S305delinsK (see SEQ ID NO: 9), S305delinsK (see SEQ ID NO: 10), K292_S305del (see SEQ ID NO: 11), and S293_S305del (see SEQ ID NO: 12). In some embodiments, the C-terminus of the D1L3 domain (having a BD deletion) has from 1 to 10 or from 1 to 5 amino acids at the C-terminus that do not align with the C-terminal BD, and which do not negatively impact chromatin degrading activity in an in vitro assay.

In some embodiments, the D1L3 variant is an engineered fusion protein comprising: a DNASE1L3 domain of a sequence selected from SEQ ID NO:8 through SEQ ID NO:16; a linker of a sequence selected from SEQ ID NO:31 through SEQ ID NO:38; and an albumin domain having the sequence of SEQ ID NO:39 or a variants or fragment as described. In some embodiments, the D1L3 variant has one or more building block substitutions from D1, which are described in PCT/US2018/04708, which is hereby incorporated by reference.

In some embodiments, the D1L3 sequence or domain contains a building block substitution from D1, which can be selected from one or more of: M21_R22delinsLK, C24_S25delinsAA, V28_S30delinsIQT, S34T, Q36_V44delinsMSNATLVSY, K47_K50delinsQILS, C52Y, I55_M58delinsIALVQE, I60_K61delinsVR, N64_I70delinsHLTAVGK, M72_K74delinsLDN, R77_I83delinsQDAPD, N86H, I89V, S91_R92delinsEP, T97S, Q101R, A103L, L105V, K107_L110delinsRPDQ, V113_R115delinsAVD, H118Y, H120D, Y122_A127delinsGCEPCGN, V129T, S131N, F135_V136delinsAI, W138R, Q140_H143 delinFSRF, A145_D148delinsEVRE, V150A, I152V, T156_T157delinsAA, E159_S161delinsGDA, K163A, E167A, V169_E170delinsYD, T173L, K176_R178delinsQEK, K180_A181 delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259A, K262G, T264_E267delinsSDQL, L269_V271delinsQAI, F275Y, F279_K280delinsVM, Q282_S205delinsK, wherein each of the foregoing substitutions is numbered with respect to SEQ ID NO: 4.

For example, the D1L3 variant may have the building block substitution from D1 of Q282_S305delinsK, which includes a deletion of the C terminal basic domain, which is absent in D1. In some embodiments, the D1L3 enzyme has an amino acid substitution at the position corresponding to position 101 of SEQ ID NO:4. The substitution can be Arg based on the corresponding building block from D1, or in some embodiments is Lys. Substitutions at this position can enhance chromatin-degrading activity of D1L3. Other substitutions at this position will likely show similar properties.

Linkers where present can be selected from flexible, rigid, and cleavable peptide linkers. Flexible linkers are predominately or entirely composed of small, non-polar or polar residues such as Gly, Ser and Thr. An exemplary flexible linker comprises $(Gly_ySer)_n$ linkers, where y is from 1 to 10 (e.g., from 1 to 5), and n is from 1 to about 10, and in some embodiments, is from 3 to about 6. In exemplary embodiments, y is from 2 to 4, and n is from 3 to 8. Due to their flexibility, these linkers are unstructured. More rigid linkers include polyproline or poly Pro-Ala motifs and α-helical linkers. An exemplary α-helical linker is $A(EAAAK)_nA$, where n is as defined above (e.g., from 1 to 10, or 2 to 6). Generally, linkers can be predominately composed of amino acids selected from Gly, Ser, Thr, Ala, and Pro. Exemplary linker sequences contain at least 10 amino acids, and may be in the range of 15 to 35 amino acids. Exemplary linker designs are provided as SEQ ID NOS: 31 to 38.

Figure 20:
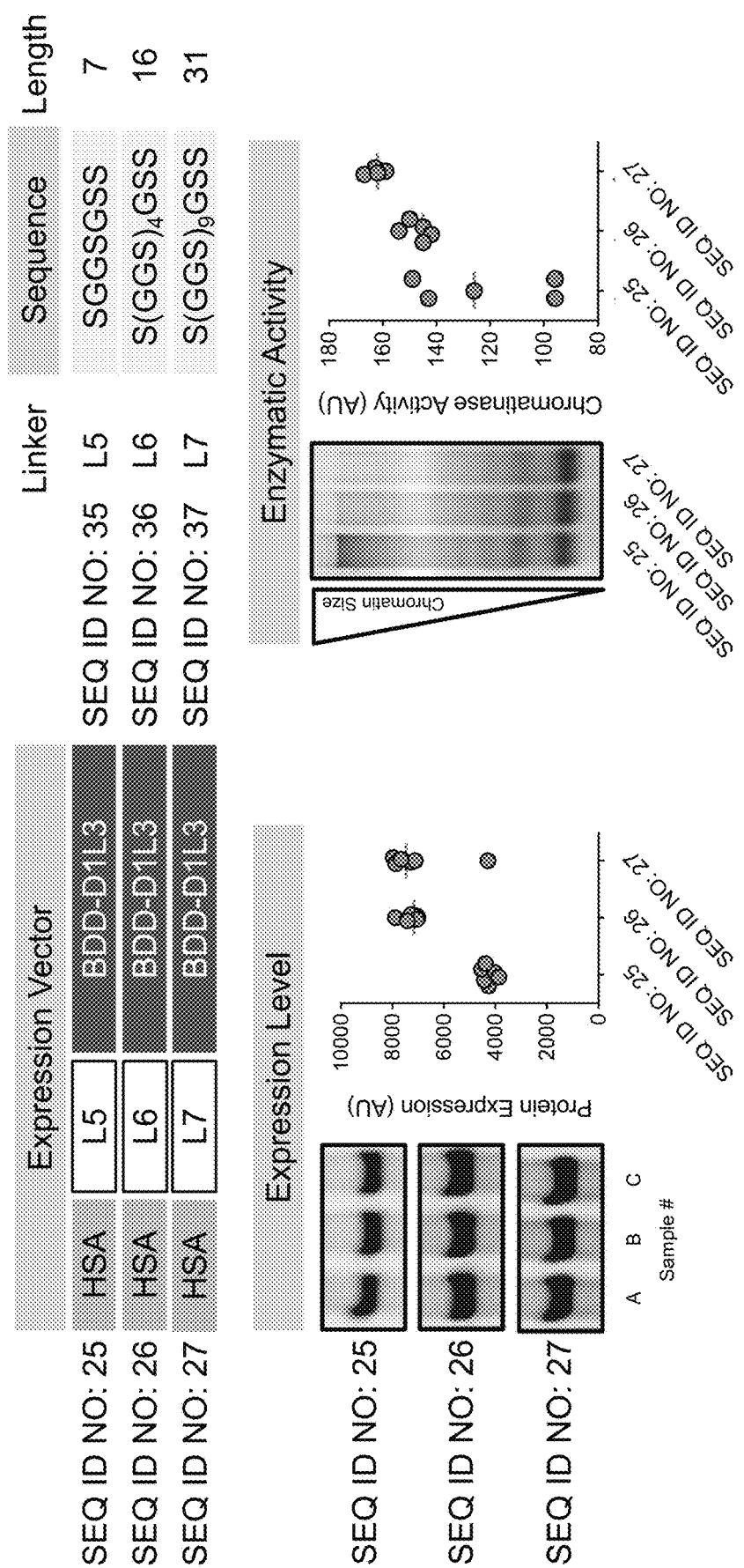
FIG. 20 illustrates the expression levels and chromatin degrading activity of human serum albumin (HSA) fusion constructs of Basic Domain Deleted-DNASE1L3 (BDD-D1L3) produced in *Pichia pastoris*. The HSA is fused to the N-terminus of BDD-D1L3. Three different linker sequences (L5, L6, L7) were placed between HSA and D1L3.
Figure 21B:
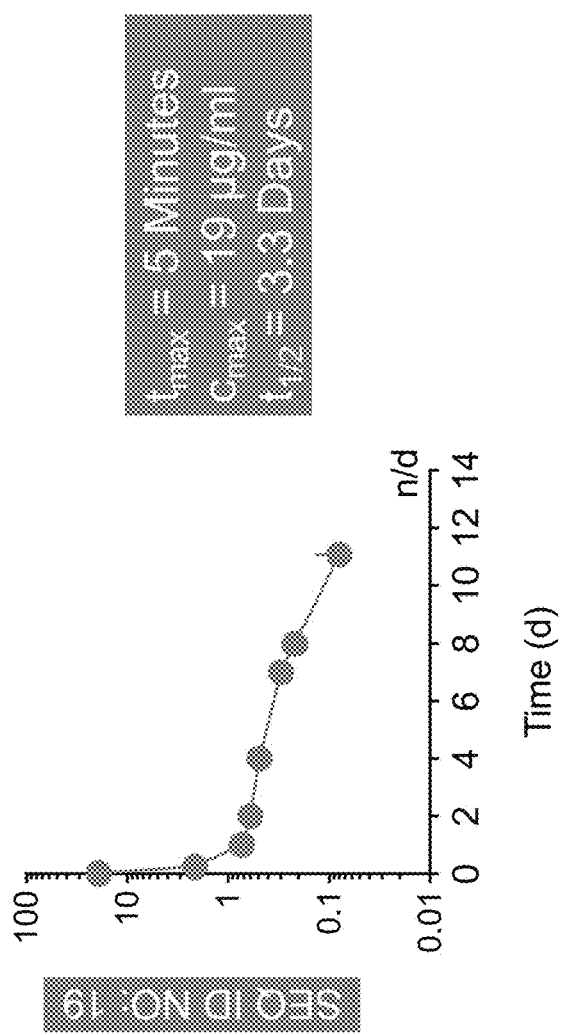
FIGS. 21A-B show the serum chromatin degrading activity and circulation half-life of albumin D1L3 fusion proteins.
Figure 21A:
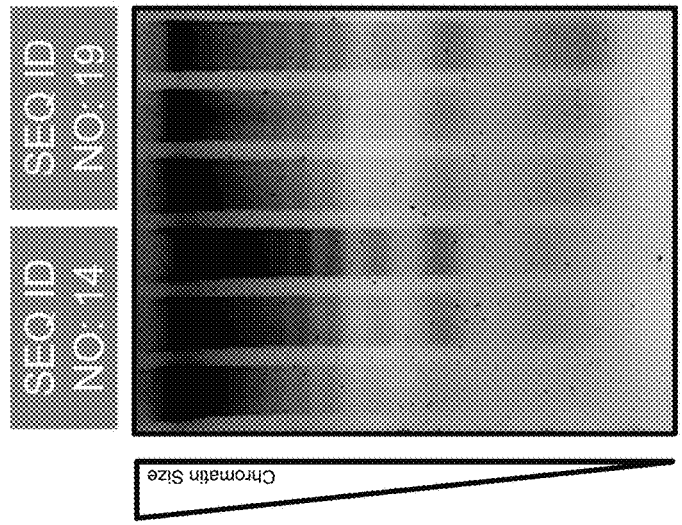

In some embodiments, the variant comprises a linker, wherein the amino acid sequence of the linker is predominately glycine and serine residues, or consists essentially of glycine and serine residues. In some embodiments, the ratio of Ser and Gly in the linker is, respectively, from about 1:1 to about 1:10, from about 1:2 to about 1:6, or about 1:4. Exemplary linker sequences comprise S(GGS)₄GSS (SEQ ID NO: 36), S(GGS)₉GS (SEQ ID NO: 37), (GGS)₉GS (SEQ ID NO: 39). In some embodiments, the linker has at least 10 amino acids, or at least 15 amino acids, or at least 20 amino acids, or at least 25 amino acids. For example, the linker may have a length of from 15 to 30 amino acids. In various embodiments, longer linkers of at least 15 amino acids can provide improvements in yield upon expression in *Pichia pastoris*. See FIG. 20. Further, and surprisingly, longer linker sequences showed improved chromatin-degrading activity, as compared to shorter linker sequences. See FIG. 20.

In various embodiments, D1L3 variant is a fusion protein comprising the amino acid sequence of any one of SEQ ID NOS: 17 to 30. In other embodiments, the D1L3 variant is a fusion protein comprising the amino acid sequence of any one of SEQ ID NOS: 17 to 30 and having from one to twenty or from one to ten, or from one to five amino acid modifications independently selected from amino acid insertions, deletions, or substitutions with respect to the reference sequence selected from SEQ ID NOS: 17 to 30. In some embodiments, the amino acid modifications are in the D1L3 domain, the albumin domain, or in both domains of the fusion protein. In some embodiments, the variant has the amino acid sequence of SEQ ID NO: 19, SEQ ID NO: 22, SEQ ID NO: 26, SEQ ID NO: 27, SEQ ID NO: 28, SEQ ID NO: 29, or SEQ ID NO: 30. In these embodiments, the albumin amino acid sequence is fused at the N-terminus or N-terminal side of D1L3 (or variant) through an intermediate or long flexible linker.

In other embodiments, the linker is a physiologically-cleavable linker, such as a protease-cleavable linker. For example, the protease may be a coagulation pathway protease, such as activated Factor XII. In certain embodiments, the linker comprises the amino acid sequence of Factor XI (SEQ ID NO: 42) and/or prekallikrein (SEQ ID NO: 44 or 45) or a physiologically cleavable fragment thereof. In selected embodiments, the linker amino acid sequence from Factor XI contains all or parts of SEQ ID NO: 42 (e.g., parts of SEQ ID NO:42, including modifications of SEQ ID NO:42 that allow for cleavage by Factor XIIa). In some embodiments, the linker amino acid sequence from prekallikrein contains all or parts of SEQ ID NO: 44 (e.g., parts of SEQ ID NO: 44, including modifications of SEQ ID NO: 44 that allow for cleavage by Factor XIIa). In other embodiments, the linker includes a peptide sequence that is targeted for cleavage by a neutrophil specific protease, such as neutrophil elastase, cathepsin G, and proteinase 3.

Some exemplary embodiments of D1L3 fusion proteins comprise a combination of three amino acid sequences that can be independently selected from sequences disclosed herein, and such sequences arranged in order from N-terminus to C-terminus:

```
Fusion 1:
SEQ ID NO: 4, SEQ ID NO: 31, SEQ ID NO: 39;

Fusion 2:
SEQ ID NO: 5, SEQ ID NO: 31, SEQ ID NO: 39;

Fusion 3:
SEQ ID NO: 8, SEQ ID NO: 31, SEQ ID NO: 39;

Fusion 4:
SEQ ID NO: 9, SEQ ID NO: 31, SEQ ID NO: 39;

Fusion 5:
SEQ ID NO: 10, SEQ ID NO: 31, SEQ ID NO: 39;

Fusion 6:
SEQ ID NO: 11, SEQ ID NO: 31, SEQ ID NO: 39;

Fusion 7:
SEQ ID NO: 12 SEQ ID NO: 31, SEQ ID NO: 39;
```

-continued

Fusion 8:
SEQ ID NO: 13, SEQ ID NO: 31, SEQ ID NO: 39;

Fusion 9:
SEQ ID NO: 14, SEQ ID NO: 31, SEQ ID NO: 39;

Fusion 10:
SEQ ID NO: 15, SEQ ID NO: 31, SEQ ID NO: 39;

Fusion 11:
SEQ ID NO: 16, SEQ ID NO: 31, SEQ ID NO: 39;

Fusion 12:
SEQ ID NO: 4, SEQ ID NO: 32, SEQ ID NO: 39;

Fusion 13:
SEQ ID NO: 5, SEQ ID NO: 32, SEQ ID NO: 39;

Fusion 14:
SEQ ID NO: 8, SEQ ID NO: 32, SEQ ID NO: 39;

Fusion 15:
SEQ ID NO: 9, SEQ ID NO: 32, SEQ ID NO: 39;

Fusion 16:
SEQ ID NO: 10, SEQ ID NO: 32, SEQ ID NO: 39;

Fusion 17:
SEQ ID NO: 11, SEQ ID NO: 32, SEQ ID NO: 39;

Fusion 18:
SEQ ID NO: 12 SEQ ID NO: 32, SEQ ID NO: 39;

Fusion 19:
SEQ ID NO: 13, SEQ ID NO: 32, SEQ ID NO: 39;

Fusion 20:
SEQ ID NO: 14, SEQ ID NO: 32, SEQ ID NO: 39;

Fusion 21:
SEQ ID NO: 15, SEQ ID NO: 32, SEQ ID NO: 39;

Fusion 22:
SEQ ID NO: 16, SEQ ID NO: 32, SEQ ID NO: 39;

Fusion 23:
SEQ ID NO: 4, SEQ ID NO: 33, SEQ ID NO: 39;

Fusion 24:
SEQ ID NO: 5, SEQ ID NO: 33, SEQ ID NO: 39;

Fusion 25:
SEQ ID NO: 8, SEQ ID NO: 33, SEQ ID NO: 39;

Fusion 26:
SEQ ID NO: 9, SEQ ID NO: 33, SEQ ID NO: 39;

Fusion 27:
SEQ ID NO: 10, SEQ ID NO: 33, SEQ ID NO: 39;

Fusion 28:
SEQ ID NO: 11, SEQ ID NO: 33, SEQ ID NO: 39;

Fusion 29:
SEQ ID NO: 12 SEQ ID NO: 33, SEQ ID NO: 39;

Fusion 30:
SEQ ID NO: 13, SEQ ID NO: 33, SEQ ID NO: 39;

Fusion 31:
SEQ ID NO: 14, SEQ ID NO: 33, SEQ ID NO: 39;

Fusion 32:
SEQ ID NO: 15, SEQ ID NO: 33, SEQ ID NO: 39;

Fusion 33:
SEQ ID NO: 16, SEQ ID NO: 33, SEQ ID NO: 39;

Fusion 34:
SEQ ID NO: 4, SEQ ID NO: 34, SEQ ID NO: 39;

Fusion 35:
SEQ ID NO: 5, SEQ ID NO: 34, SEQ ID NO: 39;

Fusion 36:
SEQ ID NO: 8, SEQ ID NO: 34, SEQ ID NO: 39;

Fusion 37:
SEQ ID NO: 9, SEQ ID NO: 34, SEQ ID NO: 39;

Fusion 38:
SEQ ID NO: 10, SEQ ID NO: 34, SEQ ID NO: 39;

Fusion 39:
SEQ ID NO: 11, SEQ ID NO: 34, SEQ ID NO: 39;

Fusion 40:
SEQ ID NO: 12 SEQ ID NO: 34, SEQ ID NO: 39;

Fusion 41:
SEQ ID NO: 13, SEQ ID NO: 34, SEQ ID NO: 39;

Fusion 42:
SEQ ID NO: 14, SEQ ID NO: 34, SEQ ID NO: 39;

Fusion 43:
SEQ ID NO: 15, SEQ ID NO: 34, SEQ ID NO: 39;

Fusion 44:
SEQ ID NO: 16, SEQ ID NO: 34, SEQ ID NO: 39;

Fusion 45:
SEQ ID NO: 4, SEQ ID NO: 35, SEQ ID NO: 39;

Fusion 46:
SEQ ID NO: 5, SEQ ID NO: 35, SEQ ID NO: 39;

Fusion 47:
SEQ ID NO: 8, SEQ ID NO: 35, SEQ ID NO: 39;

Fusion 48:
SEQ ID NO: 9, SEQ ID NO: 35, SEQ ID NO: 39;

Fusion 49:
SEQ ID NO: 10, SEQ ID NO: 35, SEQ ID NO: 39;

Fusion 50:
SEQ ID NO: 11, SEQ ID NO: 35, SEQ ID NO: 39;

Fusion 51:
SEQ ID NO: 12 SEQ ID NO: 35, SEQ ID NO: 39;

Fusion 52:
SEQ ID NO: 13, SEQ ID NO: 35, SEQ ID NO: 39;

Fusion 53:
SEQ ID NO: 14, SEQ ID NO: 35, SEQ ID NO: 39;

Fusion 54:
SEQ ID NO: 15, SEQ ID NO: 35, SEQ ID NO: 39;

Fusion 55:
SEQ ID NO: 16, SEQ ID NO: 35, SEQ ID NO: 39;

Fusion 56:
SEQ ID NO: 4, SEQ ID NO: 36, SEQ ID NO: 39;

Fusion 57:
SEQ ID NO: 5, SEQ ID NO: 36, SEQ ID NO: 39;

Fusion 58:
SEQ ID NO: 8, SEQ ID NO: 36, SEQ ID NO: 39;

Fusion 59:
SEQ ID NO: 9, SEQ ID NO: 36, SEQ ID NO: 39;

Fusion 60:
SEQ ID NO: 10, SEQ ID NO: 36, SEQ ID NO: 39;

Fusion 61:
SEQ ID NO: 11, SEQ ID NO: 36, SEQ ID NO: 39;

-continued

Fusion 62:
SEQ ID NO: 12 SEQ ID NO: 36, SEQ ID NO: 39;

Fusion 63:
SEQ ID NO: 13, SEQ ID NO: 36, SEQ ID NO: 39;

Fusion 64:
SEQ ID NO: 14, SEQ ID NO: 36, SEQ ID NO: 39;

Fusion 65:
SEQ ID NO: 15, SEQ ID NO: 36, SEQ ID NO: 39;

Fusion 66:
SEQ ID NO: 16, SEQ ID NO: 36, SEQ ID NO: 39;

Fusion 67:
SEQ ID NO: 4, SEQ ID NO: 37, SEQ ID NO: 39;

Fusion 68:
SEQ ID NO: 5, SEQ ID NO: 37, SEQ ID NO: 39;

Fusion 69:
SEQ ID NO: 8, SEQ ID NO: 37, SEQ ID NO: 39;

Fusion 70:
SEQ ID NO: 9, SEQ ID NO: 37, SEQ ID NO: 39;

Fusion 71:
SEQ ID NO: 10, SEQ ID NO: 37, SEQ ID NO: 39;

Fusion 72:
SEQ ID NO: 11, SEQ ID NO: 37, SEQ ID NO: 39;

Fusion 73:
SEQ ID NO: 12 SEQ ID NO: 37, SEQ ID NO: 39;

Fusion 74:
SEQ ID NO: 13, SEQ ID NO: 37, SEQ ID NO: 39;

Fusion 75:
SEQ ID NO: 14, SEQ ID NO: 37, SEQ ID NO: 39;

Fusion 76:
SEQ ID NO: 15, SEQ ID NO: 37, SEQ ID NO: 39;

Fusion 77:
SEQ ID NO: 16, SEQ ID NO: 37, SEQ ID NO: 39;

Fusion 78:
SEQ ID NO: 4, SEQ ID NO: 38, SEQ ID NO: 39;

Fusion 79:
SEQ ID NO: 5, SEQ ID NO: 38, SEQ ID NO: 39;

Fusion 80:
SEQ ID NO: 8, SEQ ID NO: 38, SEQ ID NO: 39;

Fusion 81:
SEQ ID NO: 9, SEQ ID NO: 38, SEQ ID NO: 39;

Fusion 82:
SEQ ID NO: 10, SEQ ID NO: 38, SEQ ID NO: 39;

Fusion 83:
SEQ ID NO: 11, SEQ ID NO: 38, SEQ ID NO: 39;

Fusion 84:
SEQ ID NO: 12 SEQ ID NO: 38, SEQ ID NO: 39;

Fusion 85:
SEQ ID NO: 13, SEQ ID NO: 38, SEQ ID NO: 39;

Fusion 86:
SEQ ID NO: 14, SEQ ID NO: 38, SEQ ID NO: 39;

Fusion 87:
SEQ ID NO: 15, SEQ ID NO: 38, SEQ ID NO: 39;

Fusion 88:
SEQ ID NO: 16, SEQ ID NO: 38, SEQ ID NO: 39;

Fusion 89:
SEQ ID NO: 4, SEQ ID NO: 42, SEQ ID NO: 39;

Fusion 90:
SEQ ID NO: 5, SEQ ID NO: 42, SEQ ID NO: 39;

Fusion 91:
SEQ ID NO: 8, SEQ ID NO: 42, SEQ ID NO: 39;

Fusion 92:
SEQ ID NO: 9, SEQ ID NO: 42, SEQ ID NO: 39;

Fusion 93:
SEQ ID NO: 10, SEQ ID NO: 42, SEQ ID NO: 39;

Fusion 94:
SEQ ID NO: 11, SEQ ID NO: 42, SEQ ID NO: 39;

Fusion 95:
SEQ ID NO: 12 SEQ ID NO: 42, SEQ ID NO: 39;

Fusion 96:
SEQ ID NO: 13, SEQ ID NO: 42, SEQ ID NO: 39;

Fusion 97:
SEQ ID NO: 14, SEQ ID NO: 42, SEQ ID NO: 39;

Fusion 98:
SEQ ID NO: 15, SEQ ID NO: 42, SEQ ID NO: 39;

Fusion 99:
SEQ ID NO: 16, SEQ ID NO: 42, SEQ ID NO: 39

Fusion 100:
SEQ ID NO: 4, SEQ ID NO: 43, SEQ ID NO: 39;

Fusion 101:
SEQ ID NO: 5, SEQ ID NO: 43, SEQ ID NO: 39;

Fusion 102:
SEQ ID NO: 8, SEQ ID NO: 43, SEQ ID NO: 39;

Fusion 103:
SEQ ID NO: 9, SEQ ID NO: 43, SEQ ID NO: 39;

Fusion 104:
SEQ ID NO: 10, SEQ ID NO: 43, SEQ ID NO: 39;

Fusion 105:
SEQ ID NO: 11, SEQ ID NO: 43, SEQ ID NO: 39;

Fusion 106:
SEQ ID NO: 12 SEQ ID NO: 43, SEQ ID NO: 39;

Fusion 107:
SEQ ID NO: 13, SEQ ID NO: 43, SEQ ID NO: 39;

Fusion 108:
SEQ ID NO: 14, SEQ ID NO: 43, SEQ ID NO: 39;

Fusion 109:
SEQ ID NO: 15, SEQ ID NO: 43, SEQ ID NO: 39;

Fusion 110:
SEQ ID NO: 16, SEQ ID NO: 43, SEQ ID NO: 39;

Fusion 111:
SEQ ID NO: 4, SEQ ID NO: 44, SEQ ID NO: 39;

Fusion 112:
SEQ ID NO: 5, SEQ ID NO: 44, SEQ ID NO: 39;

Fusion 113:
SEQ ID NO: 8, SEQ ID NO: 44, SEQ ID NO: 39;

Fusion 114:
SEQ ID NO: 9, SEQ ID NO: 44, SEQ ID NO: 39;

Fusion 115:
SEQ ID NO: 10, SEQ ID NO: 44, SEQ ID NO: 39;

-continued

```
Fusion 116:
SEQ ID NO: 11, SEQ ID NO: 44, SEQ ID NO: 39;

Fusion 117:
SEQ ID NO: 12 SEQ ID NO: 44, SEQ ID NO: 39;

Fusion 118:
SEQ ID NO: 13, SEQ ID NO: 44, SEQ ID NO: 39;

Fusion 119:
SEQ ID NO: 14, SEQ ID NO: 44, SEQ ID NO: 39;

Fusion 120:
SEQ ID NO: 15, SEQ ID NO: 44, SEQ ID NO: 39;

Fusion 121:
SEQ ID NO: 16, SEQ ID NO: 44, SEQ ID NO: 39;

Fusion 122:
SEQ ID NO: 4, SEQ ID NO: 45, SEQ ID NO: 39;

Fusion 123:
SEQ ID NO: 5, SEQ ID NO: 45, SEQ ID NO: 39;

Fusion 124:
SEQ ID NO: 8, SEQ ID NO: 45, SEQ ID NO: 39;

Fusion 125:
SEQ ID NO: 9, SEQ ID NO: 45, SEQ ID NO: 39;

Fusion 126:
SEQ ID NO: 10, SEQ ID NO: 45, SEQ ID NO: 39;

Fusion 127:
SEQ ID NO: 11, SEQ ID NO: 45, SEQ ID NO: 39;

Fusion 128:
SEQ ID NO: 12 SEQ ID NO: 45, SEQ ID NO: 39;

Fusion 129:
SEQ ID NO: 13, SEQ ID NO: 45, SEQ ID NO: 39;

Fusion 130:
SEQ ID NO: 14, SEQ ID NO: 45, SEQ ID NO: 39;

Fusion 131:
SEQ ID NO: 15, SEQ ID NO: 45, SEQ ID NO: 39;

Fusion 132:
SEQ ID NO: 16, SEQ ID NO: 45, SEQ ID NO: 39;
```

In some embodiments, the fusion protein is synthesized with a signal peptide. The signal peptide may be removed during secretion from the host cell. Exemplary signal peptides are shown SEQ ID NOS: 4 to 16 and SEQ ID NOS: 44 to 46. In some embodiments, the fusion protein is the mature protein, that is, lacking a signal peptide.

In various embodiments, the fusion protein is selected from fusion proteins 1 to 132, and the selected fusion protein may optionally have up to 20 (or up to 10) amino acid modifications independently selected from amino acid deletions, insertions, and substitutions.

In some aspects, the invention provides variants of extracellular DNASE enzymes engineered to have advantages in manufacturing, providing for production of the recombinant enzyme suitable for use in therapy, and which can optionally be used in connection with fusion protein embodiments (including albumin fusion embodiments) as already described. In various embodiments, the invention provides a recombinant D1, D1L1, D1L2, and D1L3 variant comprising one or more amino acid substitutions or deletions of cysteine residues resulting in reduced intra- and inter-molecular cross-linking via disulfide bridges during protein expression. For example, the DNase variant may lack one, two, or three cysteine residues present in the wild-type sequence (e.g., one, two, or three cysteine residues are deleted), or has one or more of such cysteine(s) substituted with other amino acid(s). In some embodiments, the one or more cysteine residues are substituted with an amino acid independently selected from Ala, Gly, and Ser, or one or more of the cysteine residues are substituted as part of a building block substitution. In some embodiments, the one or more cysteine residues that are substituted is/are not conserved between other members of the D1 protein family (e.g., D1, D1L1, D1L2, and D1L3). In some embodiments, the engineered enzyme comprises or further comprises at least one building block substitution from another member of the D1 protein family and/or other point mutation that results in increased protein stability, increased resistance towards degradation by proteases, increased bioavailability, and substantially the same or better DNA and/or chromatin and/or NET-degrading activity (in vitro or in vivo) as compared to the wild-type enzyme. In some embodiments, the substitutions and/or modifications include, among other modifications, only a single modification in cysteine residues. In some embodiments, removal of a single cysteine residue is sufficient for significant advantages in manufacturing.

In other aspects, the invention provides variants of extracellular DNASE enzymes engineered to have advantages in protease resistance, for improving in vivo half-life as well as reducing proteolysis during recombinant enzyme production. This disclosure identifies, for example, D1L3 residues that are sensitive to proteolysis by plasmin, thrombin, and/or trypsin, as well as residues (e.g., paired basic amino acids) that are sensitive to proteases produced by mammalian and non-mammalian cell lines.

The recombinant extracellular DNASE variants described herein may have a combination of point mutations including substitutions in cysteine residues, substitutions in protease-sensitive residues, and/or may comprise one or more block substitutions. Building Block Protein Engineering (BBPE) is described in PCT/US18/47084 and U.S. 62/800,790, the disclosures of which are hereby incorporated by reference. BBPE involves providing a protein-protein alignment of donor and recipient extracellular DNASE enzyme and identifying variable amino acid sequences for transfer ("building block"). The variable amino acid(s) are flanked by one or more conserved amino acids in the donor and recipient extracellular DNASE enzymes (upstream and downstream of the building block). These building blocks can be swapped between recipient and donor proteins, to produce a chimeric enzyme.

In other aspects, the invention provides a method for recombinant production of extracellular DNASE proteins, including variants thereof described herein. In some embodiments, the method employs a non-mammalian expression system, such as *Pichia pastoris*. In some embodiments, the *Pichia pastoris* encodes the DNase enzyme with the native signal peptide allowing for secretion from host cells. In some embodiments, the expression system is a mammalian cell expression system, such as Chinese Hamster Ovary (CHO) cells. In some embodiments, by removing cysteine residues that are unnecessary for activity, the invention avoids inter-molecular and intra-molecular disulfide bonds that otherwise form and hinder recombinant production. In some embodiments, substantial reductions in erroneous inter-molecular and intra-molecular disulfide bonds can be achieved with the substitution of a single cysteine residue.

In some embodiments, the recombinant expression system has a deletion or inactivation of one or more proteases that cleave at paired basic amino acids. Exemplary enzymes include Furin (expressed by CHO cells) and Aspartic proteinase 3 (Ysp1) and Kexin (Kex2) expressed by *Pichia pastoris*. In some embodiments, these enzymes are not genetically deleted or inactivated, but their activity is inhibited with a protease inhibitor during recombinant protein production.

In some embodiments, the growth medium for the non-mammalian expression system or mammalian expression system is supplemented with polyanions such as dextran sulfate, heparins, ferric citrate, and EDTA. In further embodiments, the growth medium of *Pichia pastoris* or other expression system is supplemented with dextran sulfate that has an average molecular weight of between 5 kDa and 100 kDa. In some embodiments, the dextran sulfate has an average molecular weight that is about 10 kDa or less, or about 20 kDa or less, or about 30 kDa or less, or about 40 kDa or less, or about 50 kDa or less, or about 75 kDa or less, or about 100 kDa or less. In various embodiments, the polyanion is added to the culture in an amount sufficient to complex with the recombinant protein produced.

In some embodiments, the recombinant extracellular DNASE proteins and variants thereof from the culture medium of non-mammalian expression system or mammalian expression system, are purified through a method that includes the dissociation of recombinant extracellular DNASE proteins and variants from polyanions such as dextran sulfate, heparins, EDTA. In certain embodiments, the purification method includes strong anion exchange resins such as triethylaminoethyl. In some embodiments, the extracellular DNASE protein produced according to the method is D1L3 or a variant thereof.

Accordingly, in some embodiments the invention provides a D1L3 variant comprising an amino acid sequence that is at least 80% identical to the enzyme defined by SEQ ID NO: 4 (human D1L3, Isoform 1) or SEQ ID NO: 5 (human D1L3, Isoform 2), and having one or more substitutions of cysteine residues and/or one or more substitutions of amino acids that are sensitive to proteolysis, e.g., in vivo proteolysis. In some embodiments, the D1L3 protein variant comprises one or more additional modifications that result in increased protein stability (e.g., protease resistance), higher production levels with in vitro expression systems, and/or not substantially less, the same, or better DNA and/or chromatin and/or NET-degrading activity as compared to wild-type D1L3 protein of SEQ ID NO:4 or SEQ ID NO: 5. For example, the D1L3 variant may comprise at least one additional building block substitution or point mutation disclosed in PCT/US2018/47084 (which is hereby incorporated by reference in its entirety), or may include one or more substitutions described herein for increasing protease resistance.

In some embodiments, the D1L3 variant has a substitution of Cys 68, which is optionally substituted with an amino acid selected from Ala, Ser, and Gly. In some embodiments, the variant comprises the substitution N64_I70delinsHLTAVGK. In some embodiments, the sequence HLTAVGK can be further modified by one, two, or three substitutions, deletions, and/or insertions (collectively), with the proviso that a Cys residue is not included. In some embodiments, the D1L3 variant comprises an amino acid sequence that has at least about 85%, at least about 90%, at least about 95%, or at least about 98% identity to the reference SEQ ID NO:4 or SEQ ID NO: 5.

In some embodiments, the invention provides a D1L3 enzyme having a polyethylene glycol (PEG) moiety conjugated at the position corresponding to Cys 68, which is believed to be an unpaired cysteine. In some embodiments, the D1L3 variant has a PEG conjugation to the amino acid corresponding to C194. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

Alternatively, or in addition, the invention provides a D1L3 variant comprising one or more substituted arginine and/or lysine residues resulting in increased protease resistance. In some embodiments, the D1L3 variant has a substitution at one or more positions corresponding to K180, K200, K259, and/or R285 of SEQ ID NO:4. In accordance with this disclosure, such lysine and arginine residues are identified as potential protease-sensitive sites. Thus, one or more (e.g., 1, 2, 3, or 4) of these residues may be modified with a non-charged residue, such as a residue independently selected from Ala, Gly, Leu, Ile, Val, Thr, Ser, and Pro. In some embodiments, protease-sensitive lysine or arginine residues are substituted as part of a building block substitution. For example, the D1L3 variant may comprise one or more substitutions selected from: K180_A181delinsGL, P198_A201delinsRPSQ, and K259A. In some embodiments, the D1L3 variant comprises one or both substitutions: K180_A181delinsGL, and/or P198_A201 delinsRPSQ, either of which are optionally modified by one or two amino acid substitutions, deletions, or insertions, with the proviso that the building block substitution is not modified by substitution or insertion with an R or K residue. In some embodiments, the D1L3 variant has increased resistance to proteolysis by one or more proteases selected from plasmin, thrombin, and/or trypsin.

Alternatively or in addition, the D1L3 variant comprises one or more mutations of a paired basic residue. In some embodiments, the paired basic residue corresponds to a position selected from K50/R51, R80/R81, K114/R115, K199/K200, K226/K227, K291/K292, R297/K298/K299, and K303/R304 of SEQ ID NO:4. In some embodiments, the D1L3 variant has one or more substitutions selected from a substitution corresponding to R114T, R114A, R114D, R114Q, K227S, and K227E of SEQ ID NO:4. In some embodiments, the one or more mutations of a paired basic residue include an amino acid substitution corresponding to R51K, R81K, R115K, and R304K. In some embodiments, the paired basic residue is substituted using a corresponding building block substitution. In accordance with these embodiments, the D1L3 variant will be more resistant to proteases expressed by the recombinant protein expression system (e.g., CHO and *Pichia pastoris*).

In some aspects, the invention provides a DNase 1 (D1) variant comprising an amino acid sequence that is at least 80% identical to the enzyme defined by SEQ ID NO: 1, with one or more substitutions of cysteine residues. In some embodiments, the D1 protein variant has one or more additional modifications resulting in increased protein stability, higher production levels with in vitro expression systems, and/or not substantially less, the same, or better DNA and/or chromatin and/or NET-degrading activity as compared to wild-type D1 protein of SEQ ID NO:1. For example, the D1 variant may comprise at least one additional building block substitution or point mutation disclosed in PCT/US2018/47084, which is hereby incorporated by reference in its entirety.

In some embodiments, the D1 variant has a substitution of one or both of C123 and C126, and which is/are optionally substituted with Ala, Ser, and Gly. In some embodiments, the D1 variant comprises the substitution G122_N128delinsYQGDA. In some embodiments, the D1 variant comprises an amino acid sequence that has at least 85%, at least 90%, at least 95%, or at least 98% identity to SEQ ID NO:1.

In some embodiments, the invention provides a D1 enzyme having a PEG moiety conjugated at the position corresponding to C123 and/or C126. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

In other aspects, the invention provides a D1L1 variant comprising an amino acid sequence that is at least 80% identical to the enzyme defined by SEQ ID NO: 2, with one or more substituted cysteine residues. The cysteine residue(s) are optionally non-conserved within the D1 family (e.g., C22 and/or C50), and are optionally substituted with Gly, Arg, or Ser, or are substituted as part of a building block substitution. In some embodiments, the D1L1 variant comprises an amino acid sequence that has at least 85%, at least 90%, at least 95%, or at least 98% identity to SEQ ID NO: 2.

In some embodiments, the invention provides a D1L1 enzyme having a PEG moiety conjugated at the position corresponding to C22 and/or C50. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

In some aspects, the invention provides a D1L2 variant comprising an amino acid sequence that is at least 80% identical to the enzyme defined by SEQ ID NO: 3, with one or more substituted cysteine residues. The cysteine residues may be non-conserved within the D1 family (e.g., C43), and is/are optionally substituted with Gly, Arg, or Ser, or are substituted as part of a building block substitution. In some embodiments, the D1L2 variant comprises an amino acid sequence that has at least 85%, at least 90%, at least 95%, or at least 98% identity to SEQ ID NO: 3.

In some embodiments, the invention provides a D1L2 enzyme having a PEG moiety conjugated at the position corresponding to C43. In these embodiments, the PEG moiety will provide a half-life extension property, while avoiding disulfide scrambling and/or protein misfolding. In some embodiments, the PEG moiety is conjugated through maleimide chemistry, which can be conducted under mild conditions. Other conjugation chemistries are known and may be used, such as vinyl sulfone, dithyopyridine, and iodoacetamide activation chemistries. The PEG moiety can be linear or branched, and can be generally in the range of 10 kDa to 40 kDa, or in the range of 20 to 30 kDa.

In other aspects, the invention provides isolated polynucleotides encoding the D1, D1L1, D1L2, or D1L3 variants disclosed herein, as well as vectors and host cells. Host cells can be cells of any expression system, including bacterial or eukaryotic, whether non-mammalian such as *Pichia pastoris*, or mammalian such as CHO cells.

In some embodiments, delivery of polynucleotides is used for therapy. Encoding polynucleotides can be delivered as mRNA or as DNA constructs using known procedures, e.g., electroporation or cell squeezing, and/or vectors (including viral vectors). mRNA polynucleotides can include known modifications (mmRNA) to avoid activation of the innate immune system. See WO 2014/028429, which is hereby incorporated by reference in its entirety. In some embodiments, the polynucleotide is delivered to the body of a subject. In some embodiments, the polynucleotides is delivered into a cell in vitro, and the cell is delivered to the body of a subject. The cell can be, for example, a white blood cell (e.g., a T cell or macrophage), an endothelial cell, an epithelial cell, a hepatocyte, or a stem cell.

In other aspects, the invention provides a method for producing an extracellular DNASE variant described herein. The method comprises culturing cells expressing a polynucleotide encoding the extracellular DNASE, and recovering the recombinant DNase protein. The cells may be prokaryotic or eukaryotic. In some embodiments, the DNase is expressed using a non-mammalian expression system, which is optionally *Pichia pastoris* or *Saccharomyces* spp. In some embodiments, a mammalian expression system, such as CHO cells, is employed.

The invention further provides pharmaceutical compositions comprising the extracellular DNASE or variant thereof as described herein, or optionally the polynucleotide or the vector as described, and a pharmaceutically acceptable carrier.

A vector generally comprises an isolated nucleic acid and which can be used to deliver the isolated nucleic acid to the interior of a cell. Numerous vectors are known in the art including, but not limited to, linear polynucleotides, polynucleotides associated with ionic or amphiphilic compounds, plasmids, and viruses. Exemplary vectors include autonomously replicating plasmids or a virus. The term should also be construed to include non-plasmid and non-viral compounds which facilitate transfer of nucleic acid into cells, such as, for example, polylysine compounds, liposomes, and the like. Examples of viral vectors include, but are not limited to, adenoviral vectors, adeno-associated virus vectors, retroviral vectors, and the like.

The pharmaceutical composition may be formulated for any administration route, including topical, parenteral, or pulmonary administration. In various embodiments, the composition is formulated for intradermal, intramuscular, intraperitoneal, intraarticular, intravenous, subcutaneous, intraarterial, oral, sublingual, pulmonary, or transdermal administration. In some embodiments, the composition is formulated for intravenous or subcutaneous administration.

In other aspects, the invention provides a method for treating a subject in need of extracellular DNA degradation, extracellular chromatin degradation, extracellular trap (ET) degradation and/or neutrophil extracellular trap (NET) degradation. The method comprises administering a therapeutically effective amount of the extracellular DNASE or variant thereof or composition described herein. Exemplary indications where a subject is in need of extracellular DNA or chromatin degradation (including ET or NET degradation) are disclosed in PCT/US18/47084, the disclosure of which is hereby incorporated by reference. In some embodiments, the invention provides a method for treating a subject in need thereof, the method comprising administering a therapeutically effective amount of a protein that is represented by any one of the sequences SEQ ID NO:8 to SEQ ID NO:30.

In each instance where a method for treating a subject is described, the invention likewise provides the use of one or more of the extracellular DNASE proteins for the treatment or prevention of diseases associated with ETs and/or NETs.

In various embodiments, the present invention provides a method for treating, preventing, or managing diseases or conditions characterized by the presence or accumulation of NETs. Such diseases or conditions include, but are not limited to, diseases associated with chronic neutrophilia, neutrophil aggregation and leukostasis, thrombosis and vascular occlusion, ischemia-reperfusion injury, surgical and traumatic tissue injury, an acute or chronic inflammatory reaction or disease, an autoimmune disease, cardiovascular disease, metabolic disease, systemic inflammation, inflammatory diseases of the respiratory tract, renal inflammatory diseases, inflammatory diseases related to transplanted tissue (e.g. graft-versus-host disease) and cancer (including leukemia).

In certain embodiments, the present invention pertains to the treatment of diseases or conditions characterized by deficiency of D1L3, or a deficiency of D1. In some cases, the subject has a mutation (e.g., a loss of function mutation) in the Dnase1l3 gene or the Dnase1 gene. Such subjects can manifest with an autoimmune disease (e.g., systemic lupus erythematosus (SLE) (including lupus nephritis), scleroderma or systemic sclerosis, rheumatoid arthritis, inflammatory bowel disease (including Crohn's disease and ulcerative colitis), and urticarial vasculitis). In some cases, the subject has an acquired inhibitor of D1 (e.g., anti-DNase1-antibody and actin) and/or D1L3 (e.g., anti-Dnase1l3-antibody). Such subjects can also have an autoimmune or inflammatory disease (e.g., SLE, systemic sclerosis).

In some embodiments, the subject has or is at risk of NETs occluding ductal systems. For example, the DNASE enzymes disclosed herein can be administered to a subject to treat pancreatitis, cholangitis, conjunctivitis, mastitis, dry eye disease, obstructions of vas deferens, or renal diseases.

In some embodiments, the subject has or is at risk of NETs accumulating on endothelial surfaces (e.g. surgical adhesions), the skin (e.g. wounds/scarring), or in synovial joints (e.g. gout and arthritis, e.g., rheumatoid arthritis). The DNASE enzymes described herein can be administered to a subject to treat a condition characterized by an accumulation of NETs on an endothelial surface such as, but not limited to, a surgical adhesion.

Other diseases and conditions associated with NETs, which the DNASE enzymes disclosed herein may be used to treat or prevent, include: ANCA-associated vasculitis, asthma, chronic obstructive pulmonary disease, a neutrophilic dermatosis, dermatomyositis, burns, cellulitis, meningitis, encephalitis, otitis media, pharyngitis, tonsillitis, pneumonia, endocarditis, cystitis, pyelonephritis, appendicitis, cholecystitis, pancreatitis, uveitis, keratitis, disseminated intravascular coagulation, acute kidney injury, acute respiratory distress syndrome, shock liver, hepatorenal syndrome, myocardial infarction, stroke, ischemic bowel, limb ischemia, testicular torsion, preeclampsia, eclampsia, and solid organ transplant (e.g., kidney, heart, liver, and/or lung transplant). Furthermore, the DNASE enzymes disclosed herein can be used to prevent a scar or contracture, e.g., by local application to skin, in an individual at risk thereof, e.g., an individual with a surgical incision, laceration, or burn.

In various embodiments, the subject has a disease that is or has been treated with wild-type Dnases, including D1 and streptodornase. Such diseases or conditions include thrombosis, stroke, sepsis, lung injury, atherosclerosis, viral infection, sickle cell disease, myocardial infarction, ear infection, wound healing, liver injury, endocarditis, liver infection, pancreatitis, primary graft dysfunction, limb ischemia reperfusion, kidney injury, blood clotting, alum-induced inflammation, hepatorenal injury, pleural exudations, hemothorax, intrabiliary blood clots, post pneumatic anemia, ulcers, otolaryngological conditions, oral infections, minor injuries, sinusitis, post-operative rhinoplasties, infertility, bladder catheter, wound cleaning, skin reaction test, pneumococcal meningitis, gout, leg ulcers, cystic fibrosis, Kartegener's syndrome, asthma, lobar atelectasis, chronic bronchitis, bronchiectasis, lupus, primary ciliary dyskinesia, bronchiolitis, empyema, pleural infections, cancer, dry eyes disease, lower respiratory tract infections, chronic hematomas, Alzheimer's disease, and obstructive pulmonary disease.

Other aspects and embodiments of the invention will be apparent from the following examples.

EXAMPLES

Nearly 70% of all biologics are produced using Chinese Hamster Ovary (CHO) cells. Indeed, wild-type DNASE1 (D1; dornase alpha) is typically produced in CHO cells. Despite significant advantages in cell line development and large-scale production using CHO cells, there still remains a significant challenge in the production of Dnase enzymes due to a considerable degree of variability and no reliable methods for predicting or modeling cell growth characteristics. Importantly, CHO cells were not able to stably produce hyperactive variants of D1, which prevented their clinical manufacturing, and prior to the present disclosure, the manufacturing properties of other DNASE1-protein family members, including DNASE1-LIKE 3 (D1L3), were unknown.

Using CHO and microbial expression systems, several challenges were identified in manufacturing of D1L3, including low production yield, proteolytic degradation, protein misfolding, and erroneous or undesired glycosylation. This disclosure provides technical solutions to these and other challenges in manufacturing, which also can improve the therapeutic properties of D1L3.

Example 1: Expression and Characterization of D1L3 with Basic Domain Deletion (BDD) in Chinese Hamster Ovarian (CHO) Cells and in *Pichia pastoris*

DNASE1 and DNASE1L3 preferentially cleave protein-free DNA and DNA-histone-complexes (i.e. chromatin), respectively. Previous studies suggest that a basic domain (BD) at the C-terminus of DNASE1L3, which is absent in DNASE1, is responsible for the distinct substrate specificities of both enzymes (Sisirak et al., Cell, 2016; Keyel, Developmental Biology, 2017).

A protein engineering technology, termed Building Block Protein Engineering is described in PCT/US18/47084 and U.S. 62/800,790, the disclosures of which are hereby incorporated by reference in their entireties. This approach can be applied to members of the DNASE1 and DNASE2-protein family. The method is based on the following steps: providing a protein-protein alignment of donor and recipient Dnase enzymes; identifying variable amino acid sequences for transfer, the variable amino acids being flanked by one or more conserved amino acids in the donor and recipient Dnase enzymes; substituting the variable amino acids of the recipient Dnase with the variable amino acids of the donor Dnase to create a chimeric Dnase; and recombinantly producing the chimeric Dnase.

To characterize the amino acids that are responsible for chromatin-degrading activity ("chromatinase" activity), wild-type D1L3 was substituted with building block substitutions from D1, as disclosed in PCT/US2018/047084. The building block substitutions to D1L3 are selected from human D1 and result in variants of human D1L3, which feature the following mutations: M21_R22delinsLK, C24_S25delinsAA, V28_S30delinsIQT, S34T, Q36_V44delinsMSNATLVSY, K47_K50delinsQILS, C52Y, I55_M58delinsIALVQE, I60_K61delinsVR, N64_I70delinsHLTAVGK, M72_K74delinsLDN, R77_I83delinsQDAPD, N86H, I89V, S91_R92delinsEP, T97S, Q101R, A103L, L105V, K107_L110delinsRPDQ, V113_R115delinsAVD, H118Y, H120D, Y122_A127delinsGCEPCGN, V129T, S131N, F135_V136delinsAI, W138R, Q140_H143 delinFSRF, A145_D148delinsEVRE, V150A, I152V, T156_T157delinsAA, E159_S161delinsGDA, K163A, E167A, V169_E170delinsYD, T173L, K176_R178delinsQEK, K180_A181delinsGL, N183_F186delinsDVML, P198_A201delinsRPSQ, K203_N204delinsSS, R208W, D210S, R212T, V214Q, G218P, Q220_E221delinsSA, V225_S228delinsATP, N230H, L238_R239delinsVA, Q241_S246delinsMLLRGA, K250D, N252_V254delinsALP, D256N, K259A, K262G, T264_E267delinsSDQL, L269_V271delinsQAI, F275Y, F279_K280delinsVM, Q282_S205delinsK with respect to SEQ ID NO: 4.

Figure 2:
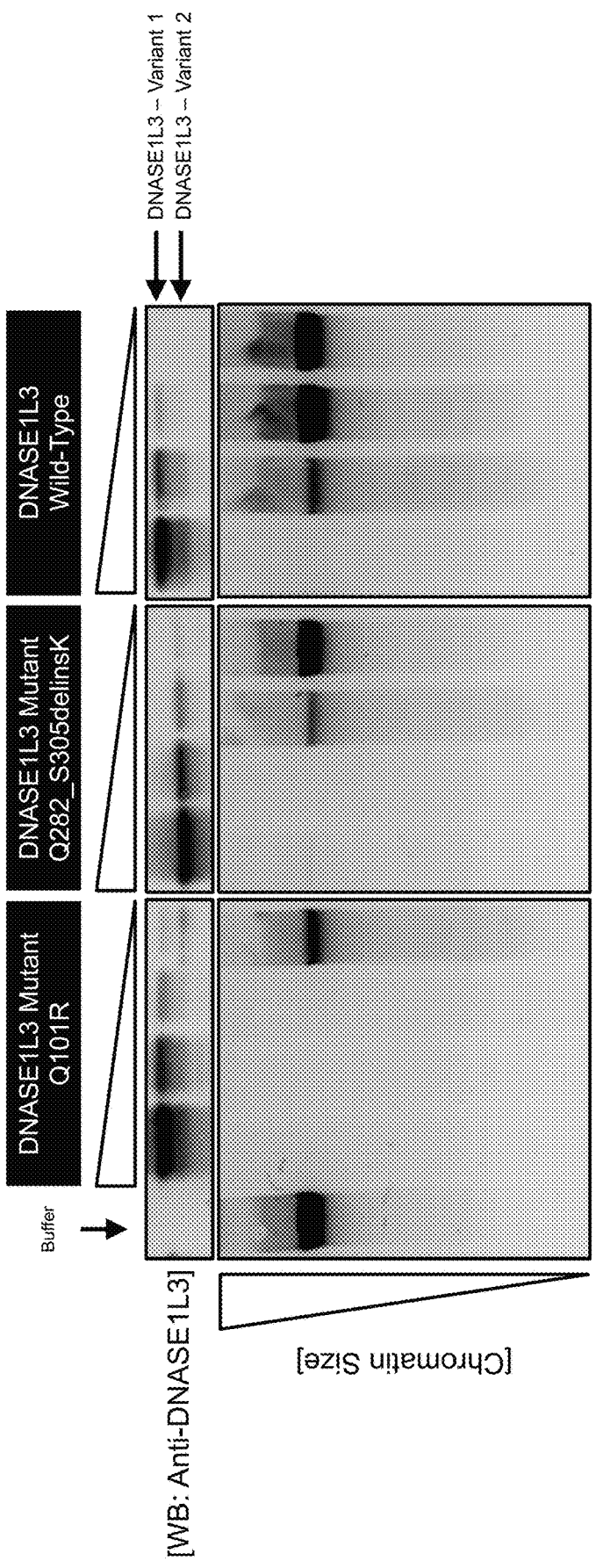
FIG. 2 shows that the characterization of two DNASE1L3 variants. Different concentrations of supernatants of CHO cell that were transfected with wild-type DNASE1L3 or DNASE1L3 with a Q101R or Q282_S305delinsK mutation were analyzed by Western Blot (WB) using an anti-DNASE1L3 antibody. A larger (variant 1) and a smaller (variant 2) bands were detected in samples with wild-type DNASE1L3 and the Q101R mutant. Only the smaller band (variant 2) was shown in samples with the Q282_S305delinsK mutant. In parallel, the chromatin degrading activity in the different concentrations of supernatants was analyzed. The figure shows DNA analyzed by agarose gel electrophoresis. Both, Q101R or Q282_S305delinsK mutations, increased the chromatin degrading activity compared to wild-type DNASE1L3.
Figure 3:
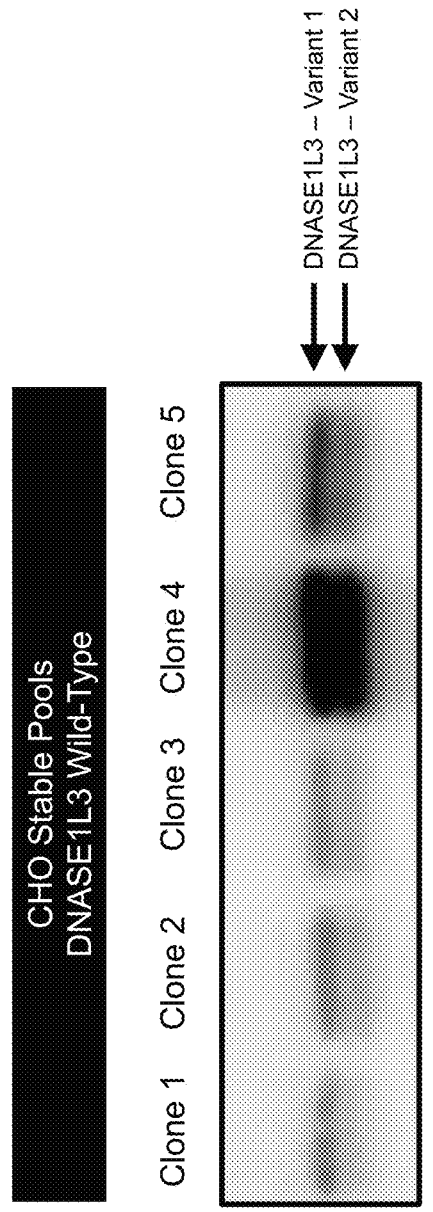
FIG. 3 illustrates the presence of DNASE1L3 variant 1 and 2 in supernatants of CHO cell that were stably transfected with wild-type DNASE1L3. Samples were analyzed by Western Blot (WB) using an anti-DNASE1L3 antibody. A larger (variant 1) and a smaller (variant 2) bands were detected in 5 clones.

These 63 D1L3 variants were screened for loss or gain of chromatin-degrading activity. In brief, D1L3 variants were transiently expressed in CHO cells using an in vitro expression vector. Culture supernatants were collected and tested for chromatin-degrading activity using purified nuclei as a source of chromatin. As shown in FIG. 1, the building block substitutions #17 and #63 from D1 significantly improved the degradation of high-molecular weight (HMW) chromatin to small fragments, when compared to wild-type D1L3. Building block substitution #7 causes a missense mutation Q101R, which replaces glutamine at position 101 with arginine (SEQ ID NO: 8). Building block substitution #63 causes the mutation Q282_S305delinsK, which deletes the full C-terminal BD of D1L3 from amino acid position 283 to 305 and replaces glutamine (Q) at position 282 with lysine (SEQ ID NO: 9). Next, we performed Western Blot analysis of the supernatants to detect the expression levels of wild-type D1L3 and both mutants (FIG. 2). To our surprise, we detected two D1L3 variants of different size in samples with wild-type D1L3 and the Q101R mutant. Samples with the Q282_S305delinsK contained only the smaller D1L3 variant. The data suggest that the BD of wild-type D1L3 is spontaneously removed (e.g., proteolyzed) during expression or post-secretion in CHO cells. The two D1L3 variants were also detected in supernatants from CHO cells that stably express WT-D1L3 (FIG. 3). Of note, the Basic Domain Deleted-D1L3 (BDD-D1L3) showed substantially increased chromatinase activity, when compared to wild-type D1L3.

Figure 4:
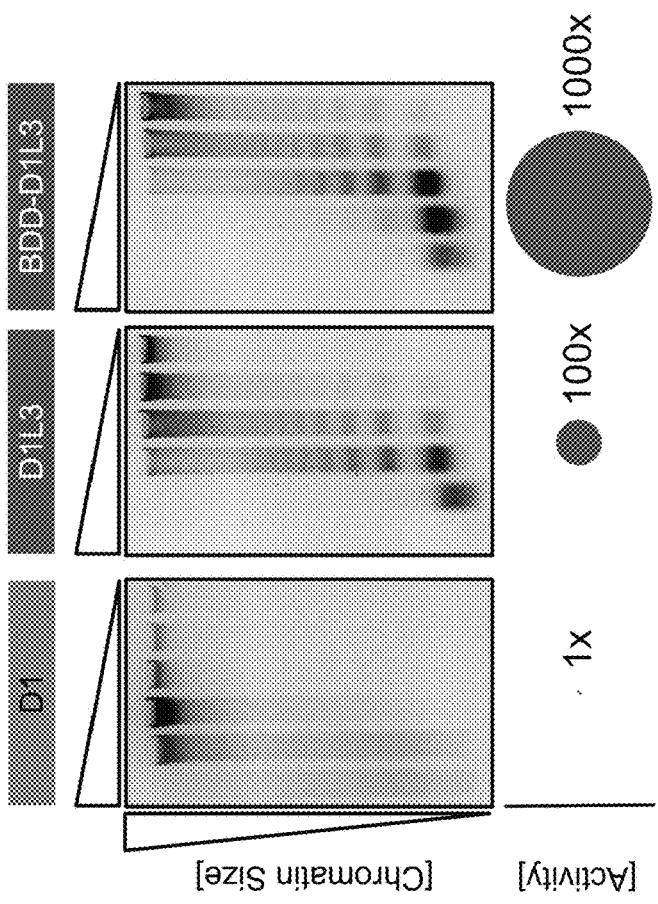
FIG. 4 shows C-terminal amino acid sequences of recombinantly expressed wild-type D1L3 in *Pichia pastoris* to identify frequent cleavage sites. Amino acid sequencing of purified wild-type D1L3 identified three C-terminal deletion mutants: K291_S305del, K292_S305del, and S293_S305del. The C-terminus of wild-type D1L3 was not detected. In parallel, the chromatin degrading activity in the different concentrations of purified protein was analyzed and compared to purified DNASE1 (D1) and the Basic Domain Deleted DNASE1L3 (BDD-D1L3) with a F275Y/F279_K280delinsVM/Q282_S305delinsK mutation. The figure shows DNA analyzed by agarose gel electrophoresis.

Next, we tested *Pichia pastoris* as an alternative, microbial expression system to CHO cells. We generally observed higher expression levels with BDD-D1L3, when compared to wild-type D1L3. Here, we purified and characterized wild-type D1L3 and BDD-D1L3 from *Pichia pastoris* fermentation supernatants (FIG. 4). Unexpectedly, we observed that wild-type D1L3 was proteolytically truncated within the BD at the amino acid positions K291, K291, or S293, leading to a heterogeneous mix of D1L3 variants after purification. Unlike wild-type D1L3, expression of BDD-D1L3 due to three building block substitutions (F275Y, F279_K280delinsVM, Q282_S205delinsK) generated a pure protein.

Next, we compared the chromatinase activity of both D1L3 purifications. We observed that the heterogenous mix of D1L3 variants with BD truncations at positions K291, K291, or S293 had approximately 10-fold lower chromatinase activity compared to the D1L3 variant with a full BD deletion due to F275Y/F279_K280delinsVM/ Q282_S205delinsK. Collectively, the data illustrate that the proteolytic cleavage of the BD can occur naturally in microbial and mammalian expression systems (i.e. CHO and *P. pastoris*), and removal of the BD appears to activate D1L3 activity to degrade chromatin.

Example 2: Expression of D1L3 in CHO Cells in Bioreactors

Figure 5:
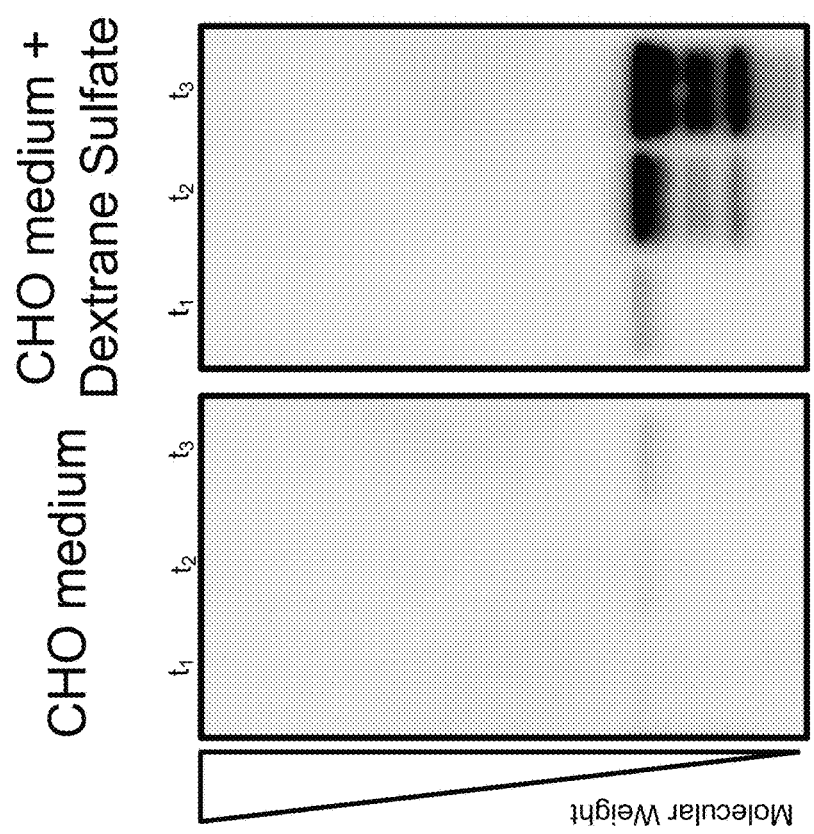
FIG. 5 shows that the addition of dextran sulfate to CHO medium improves protein yield. Stable pools of CHO cells expressing wild-type D1L3 were incubated in standard CHO medium or CHO medium supplemented with dextran sulfate. Supernatants were analyzed by Western Blot (WB) using an anti-DNASE1L3 antibody. The figure shows that D1L3 expresses poorly in CHO cells with low yield. Addition of dextran sulfate increases the yield, but does not prevent production fragmentation. \
Figure 8:
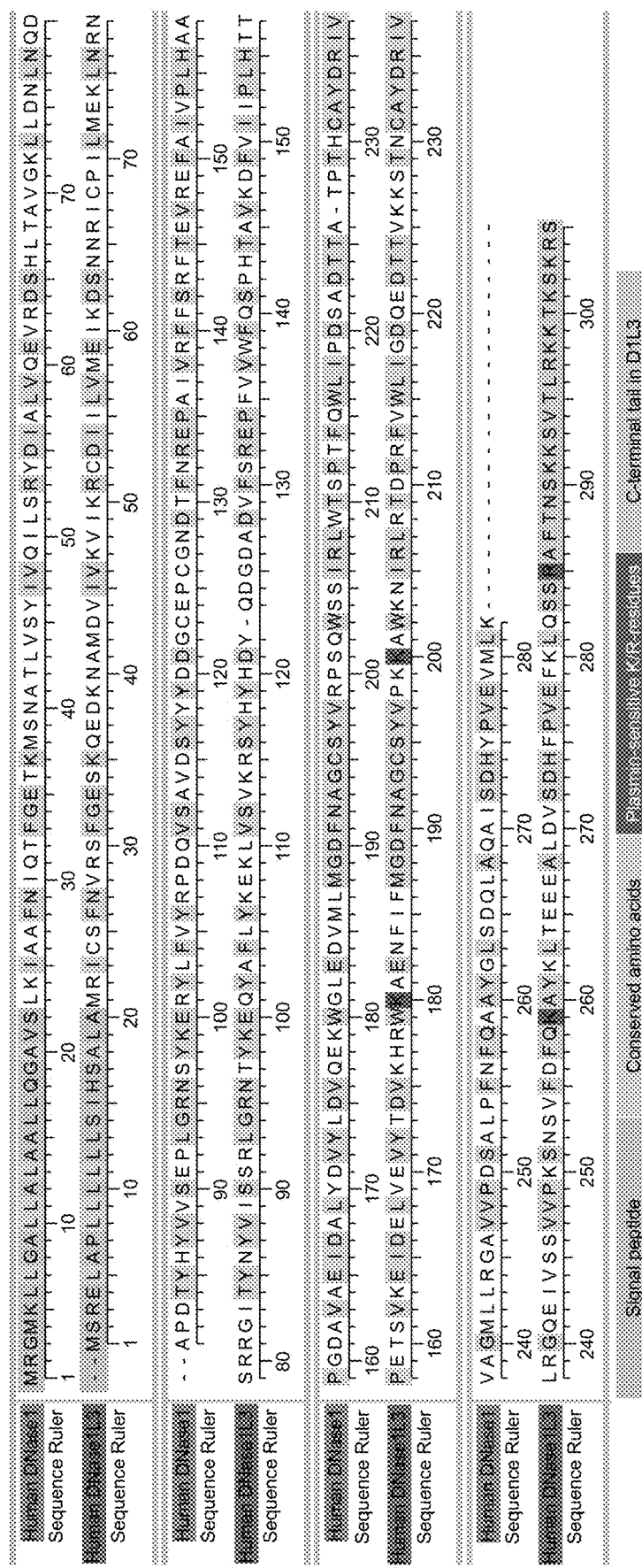
FIG. 8 is an alignment of human D1 (SEQ ID NO: 1) and human D1L3 (SEQ ID NO: 4) amino acid sequences, with plasmin sensitive KR residues shown.
Figure 10:
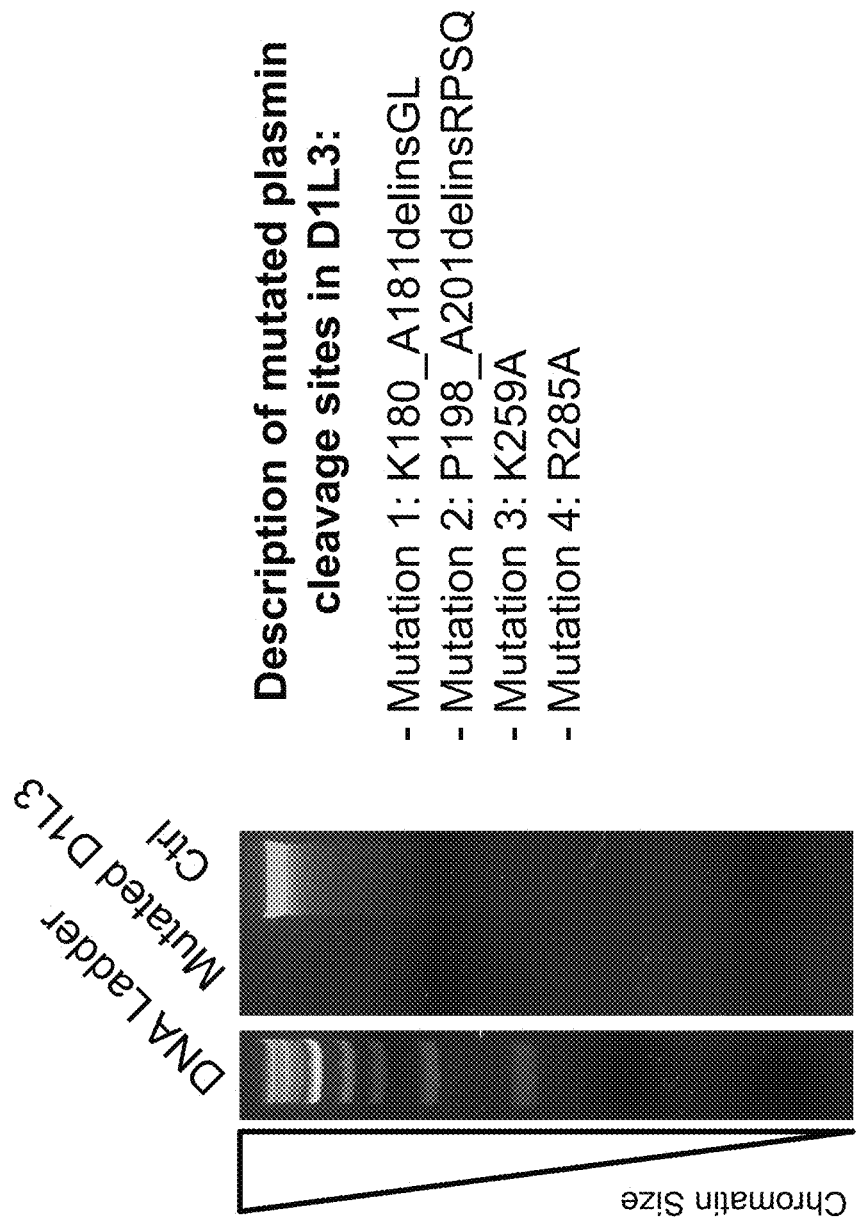
FIG. 10 shows that D1L3 with plasmin cleavage sites mutated retains enzymatic activity. Supernatants from cells that were transiently transfected DNASE1L3 containing mutations in four putative plasmid cleavage sites (K180_A181delinsGL, P198_A201delinsRPSQ, K259A, R285A) were incubated with purified nuclei (high-molecular weight chromatin) or buffer. DNA was isolated and analyzed by agarose gel electrophoresis. The figure shows the agarose gel stained with a DNA dye.

Disclosed herein is the development of stable CHO cell lines producing wild-type D1L3 (SEQ ID NO: 4). The cell lines were cultured in bioreactors using standard CHO culture medium. Specifically, FIG. 5 shows a Western Blot of human D1L3 expressed and secreted by CHO cells in a bioreactor under cGMP-compatible conditions. Samples were collected at different time points (t1-t3). Only minor levels of D1L3 and D1L3 fragments were detected. The data suggest that low production yield of D1L3 is a challenge in manufacturing of D1L3.

As disclosed herein, high production levels of wild-type D1L3 were achieved by the addition of polyanions to the culture medium. Such polyanions can comprise one or more of heparin, dextran sulfate, ferric citrate, and ethylenediaminetetraacetic acid, and represent the biologically active ingredient in "anti-cell clumping reagents". Specifically, we added dextran sulfate to the CHO culture medium and observed a strong increase in D1L3 as well as D1L3 fragments (FIG. 5). The data illustrate that polyanions increased production yield of D1L3, but did not prevent proteolytic degradation.

FIG. 6A shows that polyanions, such as dextran sulfate (DS), form a complex with D1L3. The D1L3-DS-complex prevents the interaction and scavenging of D1L3 by negatively charged surfaces during the production process. Such negatively charged surfaces include, but are not limited to, the cell surface of production cells (e.g. CHO cells, *Pichia pastoris, Saccharomyces* spp.), DNA exposed by dying cells, and bioreactor surfaces. FIG. 6B and FIG. 6C show the two-step purification process of D1L3 from DS-D1L3-complexes. As shown in FIG. 6, the first step aims to dissociate the DS-D1L3 complex. The dissociation can be achieved by incubating the DS-D1L3 complex with strong anion exchange surfaces, which bind DS and thus liberate D1L3. Specifically, the purification process can include the passage of culture medium containing the DS-D1L3 through a chromatography column that is filled with a strong anion exchange resin followed by the collection of the flow through, which contains the DS-free D1L3. The second step of the purification process is shown in FIG. 6C and includes the affinity purification of D1L3 from the DS-free flow through via the application of a strong cation exchange resin.

In conclusion, the production yield of D1L3 can be substantially increased through the addition of polyanions, such as dextran sulfate.

Example 3: Engineering D1L3 for Protease Resistance

Wild-type D1L3 contains 50 arginine and lysine residues, which makes the enzyme particularly susceptible to proteases like trypsin, thrombin, and plasmin. In this example, trypsin and plasmin cleavage sites were identified in D1L3. The sites can be mutated to generated protease-resistance variants of D1L3.

In brief, purified D1L3 was digested with trypsin. D1L3 fragments were isolated, and the amino acid sequence of the fragments determined using combinations of liquid chromatography (LC) and mass spectrometry (MS). It was identified that trypsin cleaved D1L3 at the following arginine and lysine residues: R22, R29, R51, R66, R80, R81, R95, K99, R115, K147, K163, K180, R208, R212, R235, R239, K250, and K262. These arginine and lysine residues can be substituted with small amino acids such as alanine, valine, and serine or with amino acids that have similar properties according to the Grantham's distance score (e.g. histidine, glutamine, and glutamate; FIG. 7). D1, which is protease resistant, features arginine and lysine residues corresponding to R51, R95, K99, and R235, suggesting that these residues are not primarily responsible for proteolytic degradation of D1L3.

Building Block Protein Engineering was applied to transfer the following Building Blocks from D1 to replace Building Blocks of D1L3 that contain the trypsin cleavage sites (FIG. 7): R22 (Mutation: M21_R22delinsLK), R29 (V28_S30delinsIQT), R66 (N64_I70delinsHLTAVGK), R80 (R77_I83delinsQDAPD), R81 (R77_I83delinsQDAPD), R115 (V113_R115delinsAVD), K163 (K163A), K180 (K180_A181delinsGL), R208 (R208W) MR212 (R212T), R239 (L238_R239delinsVA), K250 (K250D), and K262 (K262G).

Plasmin is a plasma protease that is generated by activation of its zymogen plasminogen. Plasminogen activator inhibitor 1 (PAI-1) inhibits the activation of plasmin. Interestingly, PAI-1 increases the enzymatic activity of D1L3 in serum, suggesting that plasmin may proteolytically inactivate D1L3. However, the plasmin cleavage sites in D1L3 have not been identified.

In silico analysis showed that the amino acid combination lysine-alanine (KA) or arginine-alanine (RA) is believed to be preferably cleaved by the protease plasmin or proteases that have plasmin-like activity. D1L3 contains a total of four putative plasmin-cleavage sites (FIG. 8): (Site 1) K180/A181 (K160/A161 without signal peptide), (Site 2) K200/A201 (K180/A181 without signal peptide), (Site 3) K259/A260 (K239/A240 without signal peptide), and (Site 4) R285/A286 (R270/A250 without signal peptide). Using a paired alignment of D1 and D1L3, we found that none of the plasmin cleavage sites are present in D1 (FIG. 8). The data are in line with the fact that D1 activity is resistant to inactivation by serum proteases, such as thrombin and plasmin. Building Block Protein Engineering was applied to transfer the following Building Blocks from D1 to replace Building Blocks of D1L3 that contain the plasmin cleavage sites (FIG. 9): (Site 1) K180_A181delinsGL, (Site 2) P198_A201delinsRPSQ, and (Site 3) K259A. R285/A286 (Site 4) is located in a C-terminal extension that is absent in D1. Consequently, we generated a D1L3 variant in which all four putative plasmin cleavage sites were mutated: K180_A181delinsGL, P198_A201delinsRPSQ, K259A, and R285A. Next, we analyzed chromatin degradation by the D1L3 variant and observed potent chromatin degrading activity in the mutated D1L3 (FIG. 10). Collectively, the data show that four arginine and lysine residues, K180, K200, K259, and R285, can be mutated to reduce the risk of proteolytic degradation without compromising enzymatic activity.

Next, purified D1L3 was digested with purified plasmin. D1L3 fragments were isolated, and the amino acid sequence of the fragments determined using combinations of LC and MS. We identified that plasmin cleaved D1L3 at the following arginine and lysine residues: R22, R29, K45, K47, K74, R81, R92, K107, K176, R212, R226, R227, K250, K259, and K262. These arginine and lysine residues can be substituted with small amino acids such as alanine, valine, and serine or with amino acids that have similar properties according to the Grantham's distance score (e.g. histidine, glutamine, and glutamate; FIG. 11). D1, which is protease resistant, features a lysine residue corresponding to K45, suggesting that this residue is not primarily responsible for proteolytic degradation of D1L3 by plasmin. Building Block Protein Engineering was applied to transfer the following Building Blocks from D1 to replace Building Blocks of D1L3 that contain the trypsin cleavage sites in silico (FIG. 11): R22 (Mutation: M21_R22delinsLK), R29 (V28_S30delinsIQT), K47 (K47_K50delinsQILS), K74 (M72_K74delinsLDN), R81 (R77_I83delinsQDAPD), R92 (S91_R92delinsEP), K107 (K107_L110delinsRPDQ), K176 (K176_R178delinsQEK), R212 (R212T), K226 (V225_S228delinsATP), K227 (V225_S228delinsATP), K250 (K250D), K259 (K259A), and K262 (K262G).

Finally, recombinantly expressed wild-type D1L3 was isolated and its C-terminus sequenced. Three different amino acid sequences were identified ending in S290 (SEQ ID NO: 10), K291 (SEQ ID NO: 11), and K292 (SEQ ID NO: 12), respectively (FIG. 4, Example 1). The data identify lysine residues 291 and 292 as prominent proteolytic cleavage sites of D1L3 during large-scale manufacturing.

Example 4: Engineering D1L3 to Avoid Degradation

We observed fragmentation of D1L3 after heterologous expression in *Pichia pastoris*. Analysis of the fragments characterized paired basic amino acids, arginine (R) and lysine (K) residues, as proteolytic cleavage sites. A similar degradation pattern was observed after expressing D1L3 in CHO cells. These observations suggest that *Pichia pastoris* and CHO cells share homologous proteases that cleave D1L3 at paired basic amino acids, and although the effect was more significant in CHO cells.

It was determined that the paired basic amino acid cleaving enzyme (PACE) contributed to the DNASE1L3 fragmentation. PACE, also known as Furin (Uniprot ID: P09958), is expressed in humans and mammals. *Pichia pastoris* expresses two enzymes, which target paired basic amino acids, namely Aspartic proteinase 3 (Gene: Ysp1; Uniprot ID: P32329) and Kexin (Gene: Kex2; Uniprot ID: P13134). Thus, DNASE1L3 and DNASE1L3 variants can be expressed in *Pichia pastoris* and in CHO cells in which Furin, Aspartic proteinase 3, and Kexin is pharmacologically inhibited or genetically depleted.

In addition, mutations of paired basic amino acids in DNASE1L3 and DNASE1L3 variants enable their expression in CHO and *Pichia pastoris* with reduced fragmentation. Analysis of DNASE1L3 fragments identified feature paired basic amino acid at positions: K50/R51, R80/R81, K114/R115, K199/K200, K226/K227, K291/K292, R297/K298/K299, and K303/R304 in SEQ ID NO: 2.

As disclosed U.S. Provisional Patent Application No. 62/800,790 (which is hereby incorporated by reference in its entirety), DNASE1L3 from other species feature amino acid substitutions at these cleavage sites, including R114T (Mouse), R114A (Rat), R114D (Guinea pig), R114Q (Cow), K227S (Dog), and K227E (Elephant). These amino acid substitutions can be applied to human DNASE1L3 to render the enzyme resistant to proteolytic degradation, including during expression in CHO cells and Pichia pastoris.

Kexin preferably cleaves after KR and RR residues. DNASE1L3 features at K50/R51, R80/R81, K114/R115, and K303/R304 are 4 KEX2-cleavage sites. Amino acid substitutions of these residues render DNASE1L3 resistant to KEX2 and enable the expression of DNASE1L3 and DNASE1L3 variants in Pichia pastoris and in CHO cells. These amino acid substitutions can be conservative, e.g. R51K, R81K, R115K, and R304K.

Example 5: Engineering D1L3 Variants to Prevent High-Molecular Weight Aggregates During cGMP-compatible expression of D1L3 in CHO cells (FIG. 12A), the accumulation of high-molecular weight aggregates of D1L3 was observed, pointing towards an additional challenge for clinical manufacturing D1L3. The high molecular weight aggregates were observed by a much lower extent in Pichia pastoris.

The application of reducing conditions to proteins of bioreactor material dissolved D1L3 aggregates. The data illustrate that D1L3 aggregate formation is caused by intra- and/or inter-molecular cross-linking via disulfide bridges during protein expression. Specifically, as shown in FIG. 12B, the gel was run under non-reducing conditions and shows the accumulation of high-molecular weight aggregates of D1L3 over time. The gel was run under reducing conditions and no aggregates were detected. The data illustrate that erroneous intra- and inter-molecular disulfide bonds cause misfolding of human D1L3 under manufacturing conditions.

Figure 13:
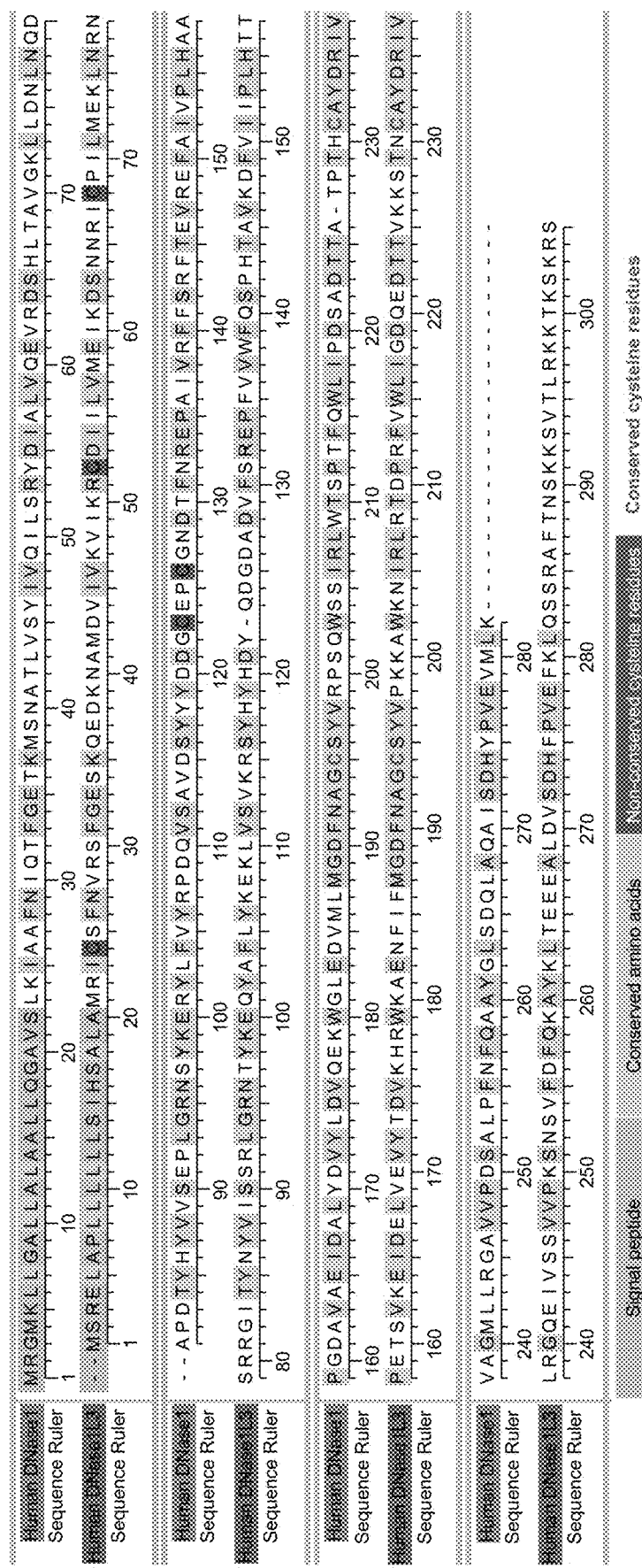
FIG. 13 is an alignment of human D1 (SEQ ID NO: 1) and human D1L3 (SEQ ID NO: 4) amino acid sequences, with conserved and non-conserved cysteine residues shown.

FIG. 13 shows an amino acid sequence alignment of human D1 (SEQ ID NO: 1) and human D1L3 (SEQ ID NO: 4). The signal peptide, conserved amino acids, variable amino acids, non-conserved cysteine residues, and conserved cysteine residues are highlighted. Mutations in non-conserved cysteine residues will reduce the possibilities of intra- and inter-molecular disulfide bonds during protein expression. Analysis of the amino acid sequence of D1L3 (SEQ ID NO: 4) showed the presence of five cysteine (C) residues: C24, C52, C68, C194, and C231 (FIG. 14). The cysteine residues C194 and C231 are conserved among all members of the DNASE1-protein family and form disulfide bonds that are required for enzymatic activity of DNASE1. The function of cysteine residues in D1L3 were not known prior to the present disclosure. Accordingly, as disclosed herein, mutations of these cysteine residues reduces the cross-linking via disulfide bridges and thus increases the yield of protein production.

Figure 15:
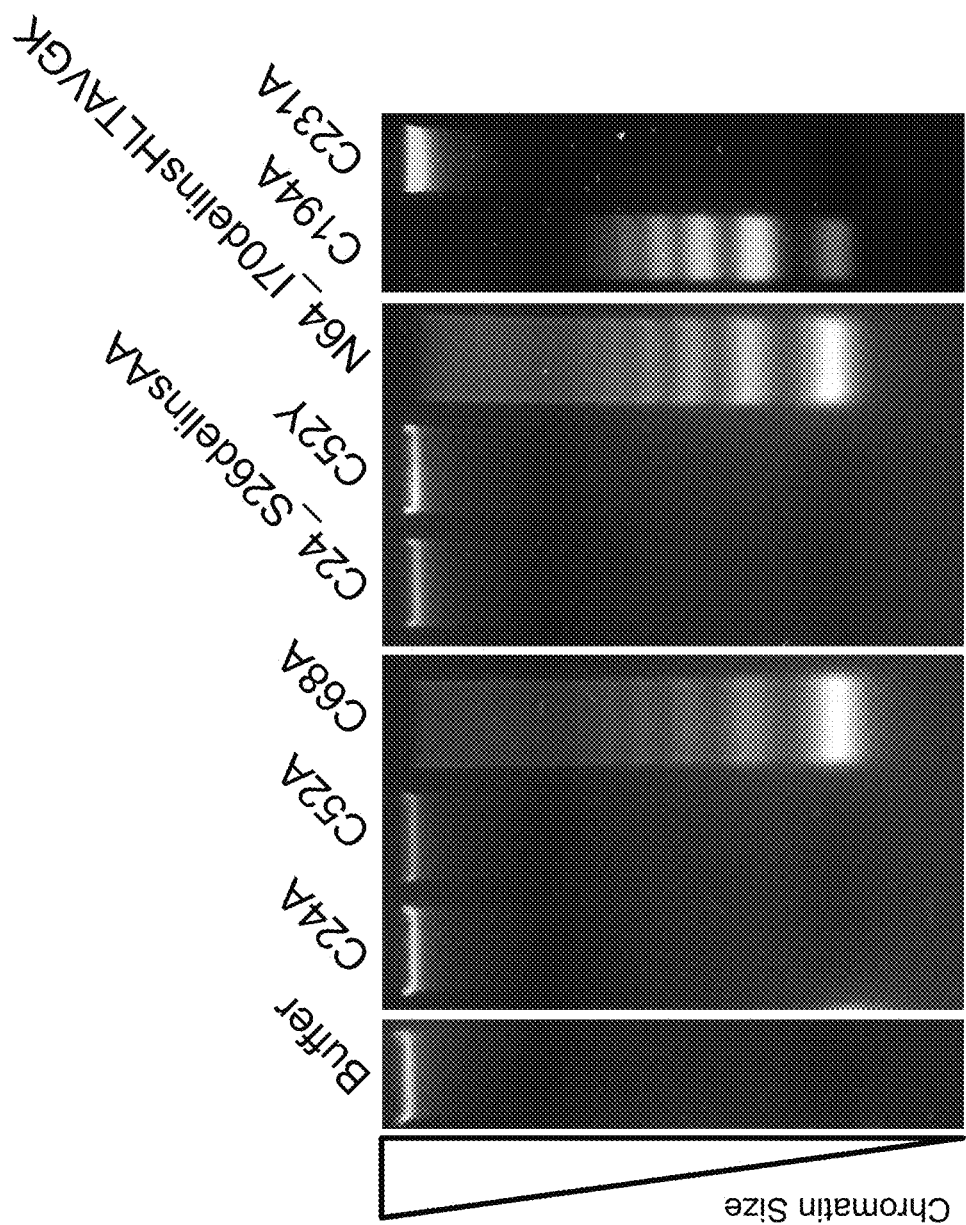
FIG. 15 shows that C68A and C194A mutation in D1L3 does not impact chromatin degrading activity. The mutations C24A and C52A abrogated chromatin-degrading activity. Supernatants from cells that were transiently transfected with mutated DNASE1L3 variants were incubated with purified nuclei or buffer. DNA was isolated and analyzed by agarose gel electrophoresis. The figure shows the agarose gel stained with a DNA dye.

Cysteine residues can be substituted with other small amino acids, namely alanine (A), serine (S), and glycine (G), among others. Such substitutions cause the following amino acid mutations C24A/S/G, C52A/S/G, C68A/S/G, C194A/S/G, and C231A/S/G. In addition, Building Blocks that comprise the conserved cysteine residues can be replaced by Building Blocks from a donor DNase of the DNASE1-protein family (e.g. D1 and D1L3). The following Building Blocks from D1 were used to replace the Building Blocks of D1L3 that contain the non-conserved cysteine residues C24, C52, and C68: C24_S25delinsAA, C52Y, and N64_I70delinsHLTAVGK. The chromatin degrading activity of D1L3 variants was quantified, as described in PCT/US18/4708. Both conventional amino acids substitutions (C24A, C52A) and building block substitutions (C24_S25delinsAA, C52Y) caused a complete absence of chromatin degradation, indicating that C24 and C52 are required for D1L3 activity (FIG. 15). Importantly, mutation of cysteine C68, either by conventional amino acid substitution [C68A, (SEQ ID NO: 13)] or by BB mutation (N64_I70delinsHLTAVGK), resulted in a D1L3 variant with chromatin degrading activity (FIG. 15). Amino acid sequence alignment showed that cysteine C68 is not conserved among other DNASE1-protein family members, supporting the notion that C68 is not required for enzymatic activity. Furthermore, it was observed that the amino acid substitution of highly conserved cysteine C194 with alanine (C194A), but not the mutation of the highly conserved cysteine C231 with alanine (C231A), resulted in an enzymatically active D1L3 variant (FIG. 15). Thus, cysteine C68 and C194 can be mutated to reduce the risk of erroneous disulfide bonds during D1L3 production.

A similar approach can be applied to mutate the non-conserved cysteine residues in the other members of the DNase1 protein family: D1, DNase1-like 1 (D1L1) and DNase1-like 2 (D1L2). D1 has two non-conserved cysteine: C123 and C126. D1L1 shows two non-conserved cysteine residues (C22, C50) that correspond to C24 and C52 in D1L2 has only one non-conserved cysteine residues: C43. Mutation of non-conserved cysteine residues of members of the DNASE1 protein family will reduce cross-linking via erroneous disulfide bridges during protein expression and thus allow for manufacturing of D1, D1L1, D1L2, and D1L3 for therapeutic applications.

Example 6: Construction and Expression of D1L3 and Albumin-D1L3 Fusion Proteins in Pichia pastoris Pichia pastoris expression of recombinant human extracellular DNASES, including D1L3, was tested. As shown in FIG. 16A, the N-terminus of D1L3 was led by the alpha-mating factor (aMF) pre-pro secretion leader from Saccharomyces cerevisiae (SEQ ID NO: 46), a common tool for heterologous protein expression in Pichia pastoris. As disclosed herein, the combination of aMF with D1L3 caused the unexpected non-processing of aMF due to glycosylation (FIG. 16B). The glycosylation of the D1L3 protein prevents the use of P. pastoris for clinical manufacturing of D1L3. D1L3 was properly processed, when N-terminus was led by native secretory signal peptide of D1L3 [FIG. 16B, (SEQ ID NO: 48)]. Importantly, aMF increased D1L3 expression 3-5-fold, when compared to the native signal peptide of D1L3. We therefore tested the processing of D1L3-fusion proteins. In pilot studies, an N-terminal fusion of aMF and human serum albumin [HSA, (SEQ ID NO: 39)] to D1L3 was generated (FIG. 17A). Some variants contained linker peptide [e.g. (GSSSS)$_3$] between HSA and D1L3. As shown in FIG. 17B and FIG. 17C, expression of the fusion protein in P. pastoris generated a non-glycosylated and enzymatically active D1L3. Furthermore, the expression levels were 5-10-fold increased, when compared to native secretory signal peptide-driven expression of D1L3. Collectively, the data illustrate that fusion of D1L3 to albumin enables manufacturing in *Pichia pastoris*.

Figure 23A:
FIGS. 23A-B illustrate the design of cleavable linker sequences.
Figure 23B:
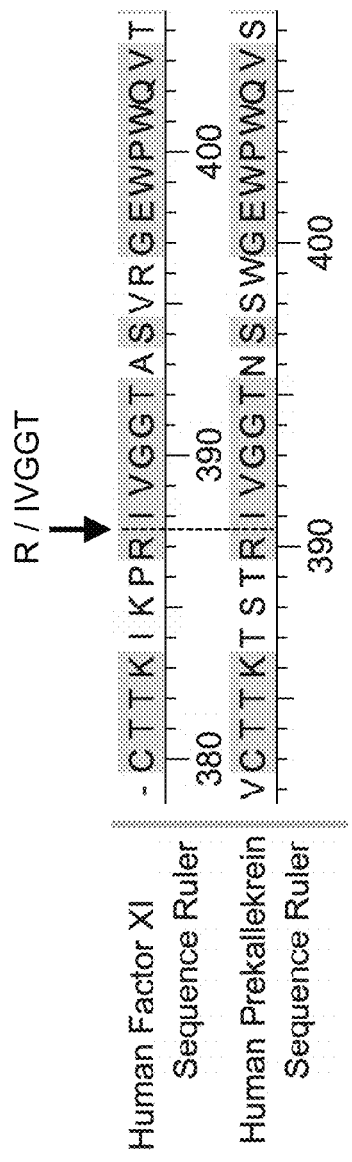

Based on these pilot studies, various HSA fusion constructs of wild-type D1L3 and BDD-D1l3 were designed and screened for expression levels of target protein (SEQ ID NOS: 17 to 28). As shown in FIG. 18, we observed that the N-terminal fusion of human serum albumin (SEQ ID: NO: 17) to a BDD-D1l3 variant (SEQ ID NO: 16) did not substantially increase the expression levels. However, of note, we did detect a strong increase in expression levels when we inserted a flexible linker composed of glycine (G) and serine (S) residues between HSA and BDD-D1L3. Furthermore, the length of the linker sequence correlated with increased expression. For example, while 12±1.9 relative Units of expression were obtained with a 5 amino acid linker (SEQ ID NO: 18), and with a 15 amino acid linker (SEQ ID NO: 19) expression was 32±3.2 relative Units, an approximately 7.5-fold improvement over the HSA-fusion without a linker. Furthermore, the N-terminal location was critical for the improved expression levels because C-terminal fusion of the linker-HSA constructs were expressed at low levels (SEQ ID NO: 20, SEQ ID NO: 21). Of note, the N-terminal fusion of HSA via a flexible linker also robustly increased the expression of wild-type D1L3 (SEQ ID NO: 22), approximately 20-fold over native D1L3 (SEQ ID NO: 4). In conclusion, the fusion of HSA via a linker to the N-terminus enable the production of D1L3 as well as BDD-D1L3 variants.

Next, we tested whether the nature of the linker sequence was critical for the improvement of D1L3 expression. We tested two additional sequences, APAPAPAPAPAPAP (SEQ ID NO: 33, 14 amino acids, rigid linker) and AEAAAKEAAAKA (SEQ ID NO: 34, 12 amino acids, rigid helical linker). As shown in FIG. 19, in both test constructs (SEQ ID NO: 23, SEQ ID NO: 24), we observed a strong increase in expression, but the rigid helical linker did not achieve similar strong expression levels as observed for GGGGSGGGGSGGGGS linker. Thus, the length and the acid composition of the linker impacted levels of D1L3 expression.

Next, we analyzed the relationship between linker length, expression level, and enzymatic activity. For these tests, designed expression vectors comprising N-terminal fusion of HSA with a GS-linker to the BDD-D1L3 variants (SEQ ID NO: 25 to 27). Three different linker lengths were tested SGGSGSS [7 amino acids, (SEQ ID NO: 35)], SGGSGGSGGSGGSGSS [16 amino acids, (SEQ ID NO: 36)], and SGGSGGSGGSGGSGGSGGSGGSGGSGGSGSS [31 amino acids, (SEQ ID NO: 37)]. As shown in FIG. 20, we observed that elongation of the linker sequence from 7 amino acids to 16 amino acids resulted in an increase in expression level. Further elongation from 16 to 31 amino acids did not increase protein expression but increased the enzymatic activity as detected by the degradation of HMW-chromatin into LMW-chromatin. Biologics fused to albumin fusion often show a reduced activity because albumin sterically hinders the interaction with substrates and ligands. Thus, peptide linkers can be used to increase the distance between albumin and the fusion protein or peptide. However, the observation that insertion of a linker sequence between HSA and D1L3 simultaneously improves enzymatic activity and expression levels was unexpected.

We compared the chromatin degrading activity of BDD-D1L3 (SEQ ID NO: 14) with its albumin-fusion counterpart (SEQ ID NO: 19). In brief, Dnase1$^{-/-}$Dnase113$^{-/-}$ mice were injected with SEQ ID NO:4 or SEQ ID NO:19. Serum was collected 15 minutes post injection. As shown in FIG. 21A, we observed similar serum chromatin degrading activity in both animals. Importantly, the fusion of albumin to the N-terminus of D1L3 and other human extracellular DNASES provides a half-life extended DNASE therapeutics. As disclosed herein, we determined the half-life of SED ID NO: 19, an HSA-BDD-D1L3 fusion protein with a flexible, GS-linker of 15 amino acids, in a commercially available rodent model. The animal model is characterized by the transgenic expression of the human FcRn, which is responsible for long half-life of albumin in circulation. While unconjugated D1L3 (e.g. SEQ ID NO: 4) has a very short half-life in circulation (<30 minutes), the albumin fusion extended the half-life to 3.3 days, thereby substantially improving systemic exposure, while also conferring rapid absorption with a $t_{max}$ of 5 minutes (FIG. 21B). Collectively, the data demonstrate the N-terminal fusion of HSA to D1L3 via a linker sequence not only facilitates the manufacturing, but also improves the in vivo pharmacokinetic properties of D1L3.

Finally, we tested the dual fusion of HSA to the N- and C-terminus of D1L3. First, we analyzed the C-terminus of D1L3 for potential attachment sites. We identified two serine residues at position 283 and 284, which provide a flexible connection of the BD (RAFTNSKKSVTLRKKTKSKRS) to the core body of D1L3. Thus, we deleted the BD and chose to attach HSA via a flexible GS-linker (SEQ ID NO: 38) to 5284. As shown in FIG. 22, fusion of HSA to the N- and C-terminus of BDD-D1L3 (SEQ ID NO: 28) maintained the high expression levels that were observed with N-terminal HSA fusion (SEQ ID NO: 27).

Example 7: Design of Cleavable Linker Sequences

The findings disclosed herein have implications beyond manufacturing. For example, D1L3 variants with C-terminal amino acid deletions, which retain their enzymatic activity to degrade chromatin and/or NETs, as exemplified by SEQ ID NO: 9 to SEQ ID NO: 12, can be used for D1L3 therapy. In addition, the site-specific alkylation of an unpaired cysteine thiol is commonly used to generate half-life extended biologics for therapeutic applications. Specifically, the non-essential cysteines C68 and C194 of D1L3 can be used for site specific PEGylation (PEG, polyethylene glycol). Furthermore, D1L3 variants that are resistant to inactivation by plasmin, due to mutations such as K180_A181delinsGL, P198_A201delinsRPSQ, K259A, and R285A, are expected to have an improved half-life and thus efficacy in therapeutic applications.

Importantly, the fusion of albumin to the N-terminus of D1L3 and other human extracellular DNASES provides a half-life extended DNASE therapeutic (FIG. 23A). Several linker sequences were used to reduce the steric inhibition of D1L3 by albumin. In addition, a physiologically cleavable peptide linker was developed. The linker peptide was designed to be cleaved when the fusion protein is in close proximity to neutrophil extracellular traps (NETs). Peptide sequences that are targeted by neutrophil specific proteases, such as neutrophil elastase, cathepsin G, and proteinase 3, are candidates for the cleavable linker sequence.

A cleavable linker sequence was developed that is cleaved intravascularly and thus optimal for intravenously and intraarterially applied DNASE therapeutics. To design the peptide, we considered that NETs have the capacity to activate blood clotting factors, in particular the clotting factor XII (FXII). Activated FXII (FXIIa) has two major substrates: clotting factor XI (FXI, SEQ ID NO: 40) and prekallikrein (PK, SEQ ID NO: 41). An amino acid sequence alignment showed that the FXIIa cleavage site is conserved in FXI and PK (FIG. 23B). In FXI, the cleavage site is between arginine 387 and isoleucine 388. In PK, the cleavage site is between arginine 390 and isoleucine 391. Indeed, FXI and PK are homologous proteins. As disclosed herein, we designed several linker peptides that contain all or parts of the FXI sequence position 380 to position 403 (SEQ ID NO: 42, SEQ ID NO: 43) or of the PK sequence position 383 to position 406 (SEQ ID NO: 44).

Figure 24:
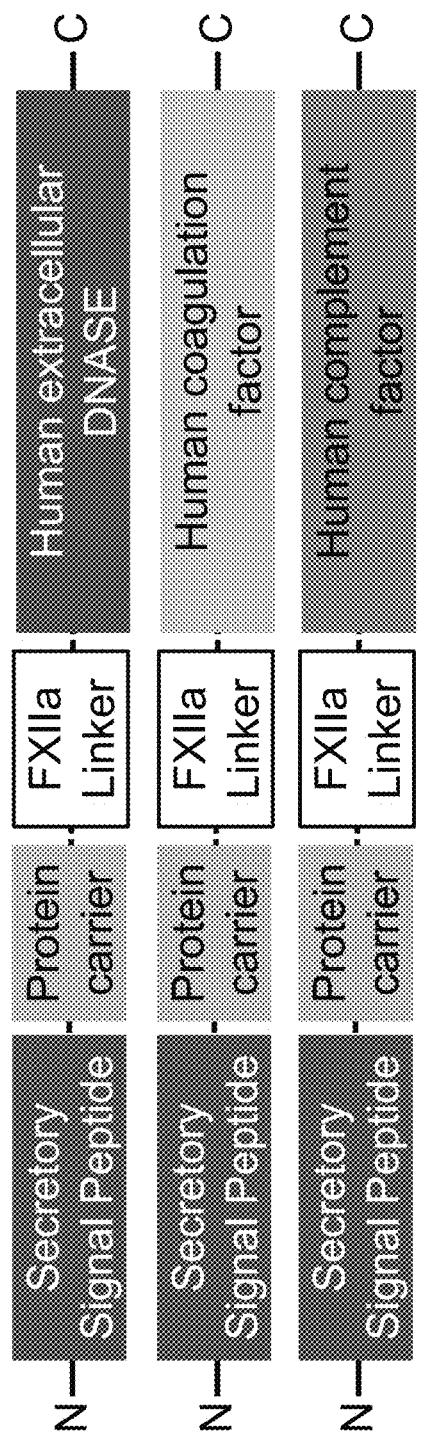
FIG. 24 illustrates other constructs that employ Factor XIIa cleavable linkers for half-life extended fusion proteins, including for human extracellular DNases, human coagulation factors, and human complement factors.

Finally, the FXIIa-cleavable linker can be used for manufacturing half-life extended version of other biologics (FIG. 24), including, but not limited to, variants of other extracellular DNASE, human coagulation factors (e.g. Factor VII, Factor VIII, and Factor IX), and complement factors (e.g. Factor H).

All patents and patent publications cited herein are hereby incorporated by reference in their entireties.

```
Wild-Type Human DNASES
DNASE1 (NP_005212.2): Signal Peptide, Mature Protein:
                                                                    SEQ ID NO: 1
MRGMKLLGALLALAALLQGAVSLKIAAFNIQTFGETKMSNATLVSYIVQILSRYDIAL

VQEVRDSHLTAVGKLLDNLNQDAPDTYHYVVSEPLGRNSYKERYLFVYRPDQVSAVDS

YYYDDGCEPCGNDTENREPAIVRFFSRFTEVREFAIVPLHAAPGDAVAEIDALYDVYL

DVQEKWGLEDVMLMGDFNAGCSYVRPSQWSSIRLWTSPTFQWLIPDSADTTATPTHCA

YDRIVVAGMLLRGAVVPDSALPENFQAAYGLSDQLAQAISDHYPVEVMLK

DNASE1-LIKE 1 (NP_006721.1): Signal Peptide; Mature Protein:
                                                                    SEQ ID NO: 2
MHYPTALLFLILANGAQAFRICAFNAQRLTLAKVAREQVMDTLVRILARCDIMVLQEV

VDSSGSAIPLLLRELNRFDGSGPYSTLSSPQLGRSTYMETYVYFYRSHKTQVLSSYVY

NDEDDVFAREPPFVAQFSLPSNVLPSLVLVPLHTTPKAVEKELNALYDVFLEVSQHWQS

KDVILLGDFNADCASLTKKRLDKLELRTEPGFHWVIADGEDTTVRASTHCTYDRVVLH

GERCRSLLHTAAAFDEPTSFQLTEEEALNISDHYPVEVELKLSQAHSVQPLSLTVLLL

LSLLSPQLCPAA

DNASE1-LIKE 2 (NP_001365.1): Signal Peptide, Mature Protein:
                                                                    SEQ ID NO: 3
MGGPRALLAALWALEAAGTAALRIGAFNIQSFGDSKVSDPACGSIIAKILAGYDLALV

QEVRDPDLSAVSALMEQINSVSEHEYSFVSSQPLGRDQYKEMYLFVYRKDAVSVVDTY

LYPDPEDVESREPFVVKFSAPGTGERAPPLPSRRALTPPPLPAAAQNLVLIPLHAAPH

QAVAEIDALYDVYLDVIDKWGTDDMLFLGDFNADCSYVRAQDWAAIRLRSSEVEKWLI

PDSADTTVGNSDCAYDRIVACGARLRRSLKPQSATVHDFQEEFGLDQTQALAISDHFP

VEVTLKFHR

DNASE1-LIKE 3; Isoform 1 (NP_004935.1): Signal Peptide, Mature Protein:
                                                                    SEQ ID NO: 4
MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDEVIIPLHTTPETSVKEIDELVEVYTD

VKHRWKAENFIFMGDENAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLQSSRAFTNS

KKSVTLRKKTKSKRS

DNASE1-LIKE 3, Isoform 2 (NP_001243489.1): Signal Peptide; Mature Protein:
                                                                    SEQ ID NO: 5
MSRELAPLLLLLLSIHSALAMRICSFNVRSFGESKQEDKNAMDVIVKVIKRCDIILVM

EIKDSNNRICPILMEKLNREKLVSVKRSYHYHDYQDGDADVESREPFVVWFQSPHTAV

KDFVIIPLHTTPETSVKEIDELVEVYTDVKHRWKAENFIFMGDENAGCSYVPKKAWKN

IRLRTDPRFVWLIGDQEDTTVKKSTNCAYDRIVLRGQEIVSSVVPKSNSVEDFQKAYK

LTEEEALDVSDHFPVEFKLQSSRAFTNSKKSVTLRKKTKSKRS
```

-continued

DNASE2A (O00115): Signal Peptide; Mature Protein:
SEQ ID NO: 6

MIPLLLAALLCVPAGALTCYGDSGQPVDWFVVYKLPALRGSGEAAQRGLQYKYLDESS

GGWRDGRALINSPEGAVGRSLQPLYRSNTSQAFLLYNDQPPQPSKAQDSSMRGHTKG

VLLLDHDGGFWLVHSVPNFPPPASSAAYSWPHSACTYGQTLLCVSFPFAQFSKMGKQL

TYTYPWVYNYQLEGIFAQEFPDLENVVKGHHVSQEPWNSSITLTSQAGAVFQSFAKFS

KFGDDLYSGWLAAALGTNLQVQFWHKTVGILPSNCSDIWQVLNVNQIAFPGPAGPSFN

STEDHSKWCVSPKGPWTCVGDMNRNQGEEQRGGGTLCAQLPALWKAFQPLVKNYQPCN

GMARKPSRAYKI

DNASE2B (Q8WZ79): Signal Peptide; Mature Protein:
SEQ ID NO: 7

MKQKMMARLLRTSFALLFLGLFGVLGAATISCRNEEGKAVDWFTFYKLPKRQNKESGE

TGLEYLYLDSTTRSWRKSEQLMNDTKSVLGRTLQQLYEAYASKSNNTAYLIYNDGVPK

PVNYSRKYGHTKGLLLWNRVQGFWLIHSIPQFPPIPEEGYDYPPTGRRNGQSGICITF

KYNQYEAIDSQLLVCNPNVYSCSIPATFHQELIHMPQLCTRASSSEIPGRLLTTLQSA

QGQKFLHFAKSDSFLDDIFAAWMAQRLKTHLLTETWQRKRQELPSNCSLPYHVYNIKA

IKLSRHSYFSSYQDHAKWCISQKGTKNRWTCIGDLNRSPHQAFRSGGFICTQNWQIYQ

AFQGLVLYYESCK

Human DNASE1L3 variants
DNASE1-LIKE 3, Q101R (Signal Peptide; Mature Protein)
SEQ ID NO: 8

MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKERYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLQSSRAFTNS

KKSVTLRKKTKSKRS

DNASE1L3, Q282_S305delinksK (Signal Peptide; Mature Protein):
SEQ ID NO: 9

MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHFPVEFKLK

DNASE1L3, S305delinsK (Signal Peptide; Mature Protein):
SEQ ID NO: 10

MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWGLENFIFMGDFNAGCSYVRPSQWKNIRLRTDPRFVWLIGDQEDTTVKKSTNCA

YDRIVLRGQEIVSSVVPKSNSVFDFQAAYKLTEEEALDVSDHFPVEFKLQSSRAFTNS

DNASE1L3, K292_S305del (Signal Peptide; Mature Protein):
SEQ ID NO: 11

MSRELAPLLLLLLSIHSALAMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

-continued

YHYHDYQDGDADVESREPFVVWFQSPHTAVKDEVIIPLHTTPETSVKEIDELVEVYTD

VKHRWGLENFIFMGDENAGCSYVRPSQWKNIRLRTDPRFVWLIGDQEDTTVKKSTNCA

YDRIVLRGQEIVSSVVPKSNSVFDFQAAYKLTEEEALDVSDHFPVEFKLQSSRAFTNS

K

DNASE1L3, S293_S305del (<u>Signal Peptide</u>; Mature Protein):
SEQ ID NO: 12

<u>MSRELAPLLLLLLSIHSALA</u>MRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWGLENFIFMGDENAGCSYVRPSQWKNIRLRTDPRFVWLIGDQEDTTVKKSTNCA

YDRIVLRGQEIVSSVVPKSNSVFDFQAAYKLTEEEALDVSDHFPVEFKLQSSRAFTNS

KK

DNASE1L3, C68A (<u>Signal Peptide</u>; Mature Protein):
SEQ ID NO: 13

<u>MSRELAPLLLLLLSIHSALA</u>MRICSFNVRSFGESKQEDKNAMDVIVKVIKRCDIILVM

EIKDSNNRI<u>A</u>PILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLQSSRAFTNS

KKSVTLRKKTKSKRS

DNASE1L3, F275Y/F279_K280delinsVM/Q282_S305delinsK (<u>Signal Peptide</u>;
Mature Protein):
SEQ ID NO: 14

<u>MSRELAPLLLLLLSIHSALA</u>MRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDEVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHYPVEVMLK

DNASE1L3, S283_S305del (<u>Signal Peptide</u>; Mature Protein):
SEQ ID NO: 15

<u>MSRELAPLLLLLLSIHSALA</u>MRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVESREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVEDFQKAYKLTEEEALDVSDHFPVEFKLQ

DNASE1L3, R285_S305del (<u>Signal Peptide</u>; Mature Protein):
SEQ ID NO: 16

<u>MSRELAPLLLLLLSIHSALA</u>MRICSFNVRSFGESKQEDKNAMDVIVKVIKRCDIILVM

EIKDSNNRICPILMEKLNREKLVSVKRSYHYHDYQDGDADVFSREPFVVWFQSPHTAV

KDFVIIPLHTTPETSVKEIDELVEVYTDVKHRWKAENFIFMGDENAGCSYVPKKAWKN

IRLRTDPRFVWLIGDQEDTTVKKSTNCAYDRIVLRGQEIVSSVVPKSNSVEDFQKAYK

LTEEEALDVSDHFPVEFKLQSS

Albumin Fusions with DNASE1L3 and Variants
Albumin - DNASE1L3 Variant - Fusion Protein. (<u>Albumin</u>, DNASE1L3 Variant):
SEQ ID NO: 17

<u>DAHKSEVAHRFKDLGEENFKALVLIAFAQYLQQCPFEDHVKLVNEVTEFAKTCVADES</u>

<u>AENCDKSLHTLFGDKLCTVATLRETYGEMADCCAKQEPERNECFLQHKDDNPNLPRLV</u>

<u>RPEVDVMCTAFHDNEETFLKKYLYEIARRHPYFYAPELLFFAKRYKAAFTECCQAADK</u>

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLMRICSFNVRSFGESKQEDKNAMDVIVKVIKRCDIILVMEIKDSNNRICPILME

KLNRNSRRGITYNYVISSRLGRNTYKEQYAFLYKEKLVSVKRSYHYDYQDGDADVFS

REPFVVWFQSPHTAVKDFVIIPLHTTPETSVKEIDELVEVYTDVKHRWKAENFIFMGD

FNAGCSYVPKKAWKNIRLRTDPRFVWLIGDQEDTTVKKSTNCAYDRIVLRGQEIVSSV

VPKSNSVFDFQKAYKLTEEEALDVSDHYPVEVMLK

Albumin - DNASE1L3 Variant - Fusion Protein. (Albumin, DNASE1L3 Variant):
SEQ ID NO: 18

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLGGGGSMRICSFNVRSFGESKQEDKNAMDVIVKVIKRCDIILVMEIKDSNNRIC

PILMEKLNRNSRRGITYNYVISSRLGRNTYKEQYAFLYKEKLVSVKRSYHYDYQDGD

ADVFSREPFVVWFQSPHTAVKDFVIIPLHTTPETSVKEIDELVEVYTDVKHRWKAENF

IFMGDFNAGCSYVPKKAWKNIRLRTDPRFVWLIGDQEDTTVKKSTNCAYDRIVLRGQE

IVSSVVPKSNSVFDFQKAYKLTEEEALDVSDHYPVEVMLK

Albumin - DNASE1L3 Variant - Fusion Protein. (Albumin, DNASE1L3 Variant):
SEQ ID NO: 19

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLGGGGSGGGGSGGGGSMRICSFNVRSFGESKQEDKNAMDVIVKVIKRCDIILVM

EIKDSNNRICPILMEKLNRNSRRGITYNYVISSRLGRNTYKEQYAFLYKEKLVSVKRS

YHYHDYQDGDADVFSREPFVVWFQSPHTAVKDFVIIPLHTTPETSVKEIDELVEVYTD

VKHRWKAENFIFMGDFNAGCSYVPKKAWKNIRLRTDPRFVWLIGDQEDTTVKKSTNCA

YDRIVLRGQEIVSSVVPKSNSVFDFQKAYKLTEEEALDVSDHYPVEVMLK

DNASE1L3 Variant - Albumin - Fusion Protein. (Albumin, DNASE1L3 Variant):
SEQ ID NO: 20

MRICSFNVRSFGESKQEDKNAMDVIVKVIKRCDIILVMEIKDSNNRICPILMEKLNRN

SRRGITYNYVISSRLGRNTYKEQYAFLYKEKLVSVKRSYHYHDYQDGDADVFSREPFV

VWFQSPHTAVKDFVIIPLHTTPETSVKEIDELVEVYTDVKHRWKAENFIFMGDFNAGC

SYVPKKAWKNIRLRTDPRFVWLIGDQEDTTVKKSTNCAYDRIVLRGQEIVSSVVPKSN

SVFDFQKAYKLTEEEALDVSDHYPVEVMLKGGGGSDAHKSEVAHRFKDLGEENFKALV

LIAFAQYLQQCPFEDHVKLVNEVTEFAKTCVADESAENCDKSLHTLFGDKLCTVATLR

ETYGEMADCCAKQEPERNECFLQHKDDNPNLPRLVRPEVDVMCTAFHDNEETFLKKYL

YEIARRHPYFYAPELLFFAKRYKAAFTECCQAADKAACLLPKLDELRDEGKASSAKQR

LKCASLQKFGERAFKAWAVARLSQRFPKAEFAEVSKLVTDLTKVHTECCHGDLLECAD

DRADLAKYICENQDSISSKLKECCEKPLLEKSHCIAEVENDEMPADLPSLAADFVESK

DVCKNYAEAKDVFLGMFLYEYARRHPDYSVVLLLRLAKTYETTLEKCCAAADPHECYA

KVFDEFKPLVEEPQNLIKQNCELFEQLGEYKFQNALLVRYTKKVPQVSTPTLVEVSRN

LGKVGSKCCKHPEAKRMPCAEDYLSVVLNQLCVLHEKTPVSDRVTKCCTESLVNRRPC

FSALEVDETYVPKEFNAETFTFHADICTLSEKERQIKKQTALVELVKHKPKATKEQLK

AVMDDFAAFVEKCCKADDKETCFAEEGKKLVAASQAALGL

DNASE1L3 Variant - Albumin - Fusion Protein. (Albumin, DNASE1L3 Variant):
SEQ ID NO: 21

MRICSFNVRSFGESKQEDKNAMDVIVKVIKRCDIILVMEIKDSNNRICPILMEKLNRN

SRRGITYNYVISSRLGRNTYKEQYAFLYKEKLVSVKRSYHYHDYQDGDADVFSREPFV

VWFQSPHTAVKDFVIIPLHTTPETSVKEIDELVEVYTDVKHRWKAENFIFMGDENAGC

SYVPKKAWKNIRLRTDPRFVWLIGDQEDTTVKKSTNCAYDRIVLRGQEIVSSVVPKSN

SVFDFQKAYKLTEEEALDVSDHYPVEVMLKGGGGSGGGGSGGGGSDAHKSEVAHRFKD

LGEENFKALVLIAFAQYLQQCPFEDHVKLVNEVTEFAKTCVADESAENCDKSLHTLFG

DKLCTVATLRETYGEMADCCAKQEPERNECFLQHKDDNPNLPRLVRPEVDVMCTAFHD

NEETFLKKYLYEIARRHPYFYAPELLFFAKRYKAAFTECCQAADKAACLLPKLDELRD

EGKASSAKQRLKCASLQKFGERAFKAWAVARLSQRFPKAEFAEVSKLVTDLTKVHTEC

CHGDLLECADDRADLAKYICENQDSISSKLKECCEKPLLEKSHCIAEVENDEMPADLP

SLAADFVESKDVCKNYAEAKDVELGMFLYEYARRHPDYSVVLLLRLAKTYETTLEKCC

AAADPHECYAKVEDEFKPLVEEPQNLIKQNCELFEQLGEYKFQNALLVRYTKKVPQVS

TPTLVEVSRNLGKVGSKCCKHPEAKRMPCAEDYLSVVLNQLCVLHEKTPVSDRVTKCC

TESLVNRRPCFSALEVDETYVPKEFNAETFTFHADICTLSEKERQIKKQTALVELVKH

KPKATKEQLKAVMDDFAAFVEKCCKADDKETCFAEEGKKLVAASQAALGL

Albumin - DNASE1L3 - Fusion Protein. (Albumin, DNASE1L3):
SEQ ID NO: 22

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI
AEVENDEMPADLPSLAADFVESKDVCKNYAEAKDVELGMELYEYARRHPDYSVVLLLR
LAKTYETTLEKCCAAADPHECYAKVEDEFKPLVEEPQNLIKQNCELFEQLGEYKFQNA
LLVRYTKKVPQVSTPTLVEVSRNLGKVGSKCCKHPEAKRMPCAEDYLSVVLNQLCVLH
EKTPVSDRVTKCCTESLVNRRPCFSALEVDETYVPKEFNAETFTFHADICTLSEKERQ
IKKQTALVELVKHKPKATKEQLKAVMDDFAAFVEKCCKADDKETCFAEEGKKLVAASQ
AALGLGGGGSGGGGSGGGGSMRICSFNVRSFGESKQEDKNAMDVIVKVIKRCDIILVM
EIKDSNNRICPILMEKLNRNSRRGITYNYVISSRLGRNTYKEQYAFLYKEKLVSVKRS
YHYHDYQDGDADVFSREPFVVWFQSPHTAVKDFVIIPLHTTPETSVKEIDELVEVYTD
VKHRWKAENFIFMGDFNAGCSYVPKKAWKNIRLRTDPRFVWLIGDQEDTTVKKSTNCA
YDRIVLRGQEIVSSVVPKSNSVFDFQKAYKLTEEEALDVSDHFPVEFKLQSSRAFTNS
KKSVTLRKKTKSKRS

Albumin - DNASE1L3 - Fusion Protein. (Albumin, DNASE1L3):    SEQ ID NO: 23
DAHKSEVAHRFKDLGEENFKALVLIAFAQYLQQCPFEDHVKLVNEVTEFAKTCVADES
AENCDKSLHTLFGDKLCTVATLRETYGEMADCCAKQEPERNECFLQHKDDNPNLPRLV
RPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVS
KLVTDLTKVHTECCHGDLLECADDRADLAKYICENQDSISSKLKECCEKPLLEKSHCI
AEVENDEMPADLPSLAADFVESKDVCKNYAEAKDVELGMELYEYARRHPDYSVVLLLR
LAKTYETTLEKCCAAADPHECYAKVEDEFKPLVEEPQNLIKQNCELFEQLGEYKFQNA
LLVRYTKKVPQVSTPTLVEVSRNLGKVGSKCCKHPEAKRMPCAEDYLSVVLNQLCVLH
EKTPVSDRVTKCCTESLVNRRPCFSALEVDETYVPKEFNAETFTFHADICTLSEKERQ
IKKQTALVELVKHKPKATKEQLKAVMDDFAAFVEKCCKADDKETCFAEEGKKLVAASQ
AALGLAPAPAPAPAPAPAPMRICSFNVRSFGESKQEDKNAMDVIVKVIKRCDIILVME
IKDSNNRICPILMEKLNRNSRRGITYNYVISSRLGRNTYKEQYAFLYKEKLVSVKRSY
HYHDYQDGDADVFSREPFVVWFQSPHTAVKDFVIIPLHTTPETSVKEIDELVEVYTDV
KHRWKAENFIFMGDFNAGCSYVPKKAWKNIRLRTDPRFVWLIGDQEDTTVKKSTNCAY
DRIVLRGQEIVSSVVPKSNSVFDFQKAYKLTEEEALDVSDHFPVEFKLQSSRAFTNSK
KSVTLRKKTKSKRS

Albumin - DNASE1L3 - Fusion Protein. (Albumin, DNASE1L3):    SEQ ID NO: 24
DAHKSEVAHRFKDLGEENFKALVLIAFAQYLQQCPFEDHVKLVNEVTEFAKTCVADES
AENCDKSLHTLFGDKLCTVATLRETYGEMADCCAKQEPERNECFLQHKDDNPNLPRLV
RPEVDVMCTAFHDNEETFLKKYLYEIARRHPYFYAPELLFFAKRYKAAFTECCQAADK
AACLLPKLDELRDEGKASSAKQRLKCASLQKFGERAFKAWAVARLSQRFPKAEFAEVS
KLVTDLTKVHTECCHGDLLECADDRADLAKYICENQDSISSKLKECCEKPLLEKSHCI
AEVENDEMPADLPSLAADFVESKDVCKNYAEAKDVFLGMFLYEYARRHPDYSVVLLLR
LAKTYETTLEKCCAAADPHECYAKVFDEFKPLVEEPQNLIKQNCELFEQLGEYKFQNA
LLVRYTKKVPQVSTPTLVEVSRNLGKVGSKCCKHPEAKRMPCAEDYLSVVLNQLCVLH
EKTPVSDRVTKCCTESLVNRRPCFSALEVDETYVPKEFNAETFTFHADICTLSEKERQ
IKKQTALVELVKHKPKATKEQLKAVMDDFAAFVEKCCKADDKETCFAEEGKKLVAASQ -continued

AALGLAEAAAKEAAAKAMRICSFNVRSFGESKQEDKNAMDVIVKVIKRCDIILVMEIK

DSNNRICPILMEKLNRNSRRGITYNYVISSRLGRNTYKEQYAFLYKEKLVSVKRSYHY

HDYQDGDADVFSREPFVVWFQSPHTAVKDFVIIPLHTTPETSVKEIDELVEVYTDVKH

RWKAENFIFMGDFNAGCSYVPKKAWKNIRLRTDPRFVWLIGDQEDTTVKKSTNCAYDR

IVLRGQEIVSSVVPKSNSVFDFQKAYKLTEEEALDVSDHFPVEFKLQSSRAFTNSKKS

VTLRKKTKSKRS

Albumin - DNASE1L3 Variant - Fusion Protein. (Albumin, DNASE1L3 Variants):
SEQ ID NO: 25

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGSSMRICSFNVRSFGESKQEDKNAMDVIVKVIKRCDIILVMEIKDSNNR

ICPILMEKLNRNSRRGITYNYVISSRLGRNTYKEQYAFLYKEKLVSVKRSYHYHDYQD

GDADVFSREPFVVWFQSPHTAVKDFVIIPLHTTPETSVKEIDELVEVYTDVKHRWKAE

NFIFMGDFNAGCSYVPKKAWKNIRLRTDPRFVWLIGDQEDTTVKKSTNCAYDRIVLRG

QEIVSSVVPKSNSVFDFQKAYKLTEEEALDVSDHFPVEFKLQ

Albumin - DNASE1L3 Variant - Fusion Protein. (Albumin, DNASE1L3 Variant):
SEQ ID NO: 26

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGSSMRICSFNVRSFGESKQEDKNAMDVIVKVIKRCDIILV

MEIKDSNNRICPILMEKLNRNSRRGITYNYVISSRLGRNTYKEQYAFLYKEKLVSVKR

SYHYHDYQDGDADVFSREPFVVWFQSPHTAVKDFVIIPLHTTPETSVKEIDELVEVYT

DVKHRWKAENFIFMGDFNAGCSYVPKKAWKNIRLRTDPRFVWLIGDQEDTTVKKSTNC

AYDRIVLRGQEIVSSVVPKSNSVFDFQKAYKLTEEEALDVSDHFPVEFKLQ

-continued

Albumin - DNASE1L3 Variant - Fusion Protein. (Albumin, DNASE1L3 Variant):

SEQ ID NO: 27

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGGSGSSMRICSFNVRSFGESKQEDKNAM

DVIVKVIKRCDIILVMEIKDSNNRICPILMEKLNRNSRRGITYNYVISSRLGRNTYKE

QYAFLYKEKLVSVKRSYHYDYQDGDADVFSREPFVVWFQSPHTAVKDFVIIPLHTTP

ETSVKEIDELVEVYTDVKHRWKAENFIFMGDFNAGCSYVPKKAWKNIRLRTDPRFVWL

IGDQEDTTVKKSTNCAYDRIVLRGQEIVSSVVPKSNSVFDFQKAYKLTEEEALDVSDH

FPVEFKLQ

Albumin - DNASE1L3 Variant - Albumin - Fusion Protein. (Albumin, DNASE1L3 Variant):

SEQ ID NO: 28

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGGSGSSMRICSFNVRSFGESKQEDKNAM

DVIVKVIKRCDIILVMEIKDSNNRICPILMEKLNRNSRRGITYNYVISSRLGRNTYKE

QYAFLYKEKLVSVKRSYHYDYQDGDADVFSREPFVVWFQSPHTAVKDFVIIPLHTTP

ETSVKEIDELVEVYTDVKHRWKAENFIFMGDFNAGCSYVPKKAWKNIRLRTDPRFVWL

IGDQEDTTVKKSTNCAYDRIVLRGQEIVSSVVPKSNSVFDFQKAYKLTEEEALDVSDH

FPVEFKLQSSGGSGGSGGSGGSGGSGGSGGSGGSGGSGSDAHKSEVAHRFKDLGEENF

KALVLIAFAQYLQQCPFEDHVKLVNEVTEFAKTCVADESAENCDKSLHTLFGDKLCTV

ATLRETYGEMADCCAKQEPERNECFLQHKDDNPNLPRLVRPEVDVMCTAFHDNEETFL

KKYLYEIARRHPYFYAPELLFFAKRYKAAFTECCQAADKAACLLPKLDELRDEGKASS

AKQRLKCASLQKFGERAFKAWAVARLSQRFPKAEFAEVSKLVTDLTKVHTECCHGDLL

ECADDRADLAKYICENQDSISSKLKECCEKPLLEKSHCIAEVENDEMPADLPSLAADE

VESKDVCKNYAEAKDVELGMFLYEYARRHPDYSVVLLLRLAKTYETTLEKCCAAADPH

-continued

ECYAKVFDEFKPLVEEPQNLIKQNCELFEQLGEYKFQNALLVRYTKKVPQVSTPTLVE

VSRNLGKVGSKCCKHPEAKRMPCAEDYLSVVLNQLCVLHEKTPVSDRVTKCCTESLVN

RRPCFSALEVDETYVPKEFNAETFTFHADICTLSEKERQIKKQTALVELVKHKPKATK

EQLKAVMDDFAAFVEKCCKADDKETCFAEEGKKLVAASQAALGL

Albumin - DNASE1L3 Isoform 2 - Fusion Protein. (Albumin, DNASE1L3 Isoform 2):

SEQ ID NO: 29

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVEDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGGSGSSMRICSFNVRSFGESKQEDKNAM

DVIVKVIKRCDIILVMEIKDSNNRICPILMEKLNREQYAFLYKEKLVSVKRSYHYHDY

QDGDADVFSREPFVVWFQSPHTAVKDFVIIPLHTTPETSVKEIDELVEVYTDVKHRWK

AENFIFMGDFNAGCSYVPKKAWKNIRLRTDPRFVWLIGDQEDTTVKKSTNCAYDRIVL

RGQEIVSSVVPKSNSVFDFQKAYKLTEEEALDVSDHFPVEFKLQSSRAFTNSKKSVTL

RKKTKSKRS

Albumin - DNASE1L3 Isoform 2 Variant - Fusion Protein. (Albumin, DNASE1L3 Isoform 2 ):

SEQ ID NO: 30

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVELGMELYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGLSGGSGGSGGSGGSGGSGGSGGSGGSGSSMRICSFNVRSFGESKQEDKNAM

DVIVKVIKRCDIILVMEIKDSNNRICPILMEKLNREQYAFLYKEKLVSVKRSYHYHDY

QDGDADVFSREPFVVWFQSPHTAVKDFVIIPLHTTPETSVKEIDELVEVYTDVKHRWK

AENFIFMGDFNAGCSYVPKKAWKNIRLRTDPRFVWLIGDQEDTTVKKSTNCAYDRIVL

RGQEIVSSVVPKSNSVFDFQKAYKLTEEEALDVSDHFPVEFKLQ

LINKER SEQUENCES

GGGGS      SEQ ID NO: 31

GGGGSGGGGSGGGGS      SEQ ID NO: 32

APAPAPAPAPAPAP      SEQ ID NO: 33

AEAAAKEAAAKA      SEQ ID NO: 34

SGGSGSS      SEQ ID NO: 35

SGGSGGSGGSGGSGSS      SEQ ID NO: 36

SGGSGGSGGSGGSGGSGGSGGSGGSGSGS      SEQ ID NO: 37

GGSGGSGGSGGSGGSGGSGGSGGSGGSGS      SEQ ID NO: 38

OTHER SEQUENCES
Human Serum Albumin (Mature Protein):      SEQ ID NO: 39

DAHKSEVAHRFKDLGEENFKALVLIAFAQYLQQCPFEDHVKLVNEVTEFAKTCVADES

AENCDKSLHTLFGDKLCTVATLRETYGEMADCCAKQEPERNECFLQHKDDNPNLPRLV

RPEVDVMCTAFHDNEETFLKKYLYEIARRHPYFYAPELLFFAKRYKAAFTECCQAADK

AACLLPKLDELRDEGKASSAKQRLKCASLQKFGERAFKAWAVARLSQRFPKAEFAEVS

KLVTDLTKVHTECCHGDLLECADDRADLAKYICENQDSISSKLKECCEKPLLEKSHCI

AEVENDEMPADLPSLAADFVESKDVCKNYAEAKDVFLGMFLYEYARRHPDYSVVLLLR

LAKTYETTLEKCCAAADPHECYAKVFDEFKPLVEEPQNLIKQNCELFEQLGEYKFQNA

LLVRYTKKVPQVSTPTLVEVSRNLGKVGSKCCKHPEAKRMPCAEDYLSVVLNQLCVLH

EKTPVSDRVTKCCTESLVNRRPCFSALEVDETYVPKEFNAETFTFHADICTLSEKERQ

IKKQTALVELVKHKPKATKEQLKAVMDDFAAFVEKCCKADDKETCFAEEGKKLVAASQ

AALGL

Human Factor XI:      SEQ ID NO: 40

MIFLYQVVHFILFTSVSGECVTQLLKDTCFEGGDITTVFTPSAKYCQVVCTYHPRCLL

FTFTAESPSEDPTRWFTCVLKDSVTETLPRVNRTAAISGYSFKQCSHQISACNKDIYV

DLDMKGINYNSSVAKSAQECQERCTDDVHCHFFTYATRQFPSLEHRNICLLKHTQTGT

PTRITKLDKVVSGFSLKSCALSNLACIRDIFPNTVFADSNIDSVMAPDAFVCGRICTH

HPGCLFFTFFSQEWPKESQRNLCLLKTSESGLPSTRIKKSKALSGFSLQSCRHSIPVF

CHSSFYHDTDFLGEELDIVAAKSHEACQKLCTNAVRCQFFTYTPAQASCNEGKGKCYL

KLSSNGSPTKILHGRGGISGYTLRLCKMDNECTTKIKPRIVGGTASVRGEWPWQVTLH

TTSPTQRHLCGGSIIGNQWILTAAHCFYGVESPKILRVYSGILNQSEIKEDTSFFGVQ

EIIIHDQYKMAESGYDIALLKLETTVNYTDSQRPICLPSKGDRNVIYTDCWVTGWGYR

KLRDKIQNTLQKAKIPLVTNEECQKRYRGHKITHKMICAGYREGGKDACKGDSGGPLS

CKHNEVWHLVGITSWGEGCAQRERPGVYTNVVEYVDWILEKTQAV

Human prekallikrein:                                          SEQ ID NO: 41

MILFKQATYFISLFATVSCGCLTQLYENAFFRGGDVASMYTPNAQYCQMRCTFHPRCL

LESFLPASSINDMEKRFGCFLKDSVTGTLPKVHRTGAVSGHSLKQCGHQISACHRDIY

KGVDMRGVNFNVSKVSSVEECQKRCTNNIRCQFFSYATQTFHKAEYRNNCLLKYSPGG

TPTAIKVLSNVESGFSLKPCALSEIGCHMNIFQHLAFSDVDVARVLTPDAFVCRTICT

YHPNCLFFTFYTNVWKIESQRNVCLLKTSESGTPSSSTPQENTISGYSLLTCKRTLPE

PCHSKIYPGVDFGGEELNVTFVKGVNVCQETCTKMIRCQFFTYSLLPEDCKEEKCKCF

LRLSMDGSPTRIAYGTQGSSGYSLRLCNTGDNSVCTTKTSTRIVGGINSSWGEWPWQV

SLQVKLTAQRHLCGGSLIGHQWVLTAAHCEDGLPLQDVWRIYSGILNLSDITKDTPFS

QIKEIIIHQNYKVSEGNHDIALIKLQAPLNYTEFQKPICLPSKGDTSTIYTNCWVTGW

GFSKEKGEIQNILQKVNIPLVTNEECQKRYQDYKITQRMVCAGYKEGGKDACKGDSGG

PLVCKHNGMWRLVGITSWGEGCARREQPGVYTKVAEYMDWILEKTQSSDGKAQMQSPA

ACTIVATABLE LINKER SEQUENCES
FXIIa-susceptible linker (Factor XI peptide):                 SEQ ID NO: 42

CTTKIKPRIVGGTASVRGEWPWQVT

FXIIa-susceptible linker                                      SEQ ID NO: 43

GGGGSPRIGGGGS

FXIIa-susceptible linker (Prekallikrein peptide):             SEQ ID NO: 44

VCTTKTSTRIVGGTNSSWGEWPWQVS

FXIIa-susceptible linker (Prekallikrein peptide):             EQ ID NO: 45

STRIVGG

SIGNAL PEPTIDES
Alpha mating factor (P01149):                                 SEQ ID NO: 46

MRFPSIFTAVLFAASSALAAPVNTTTEDETAQIPAEAVIGYSDLEGDEDVAVLPESNS

TNNGLLFINTTIASIAAKEEGVS

Human Albumin Secretory Signal Peptide + Propeptide (P02768): SEQ ID NO: 47

MKWVTFISLLFLFSSAYSRGVERR

Human DNASE1L3 Signal Peptide (Q13609):                       SEQ ID NO: 48

MSRELAPLLLLLLSIHSALA

---

What is claimed is:

1. A DNase1-like 3 (D1L3) variant having chromatin and/or NET-degrading activity in vitro, wherein the D1L3 variant comprises:
   an amino acid sequence that is at least 95% identical to amino acids 21 to 282 of SEQ ID NO: 4 or amino acids 21 to 252 of SEQ ID NO: 5; and
   a C-terminal deletion of at least 5 contiguous amino acids corresponding to amino acids 301 to 305 of the polypeptide of SEQ ID NO: 4; and
   wherein the D1L3 variant is fused or conjugated to a half-life extending moiety.

2. The D1L3 variant of claim 1, wherein the D1L3 variant is a fusion protein comprising:
   (i) a mature D1L3 enzyme, wherein the mature D1L3 enzyme:
      lacks the signal peptide corresponding to amino acids 1 to 20 of the polypeptide of SEQ ID NO: 4 or SEQ ID NO:5, and
      comprises amino acid sequence that is at least 95% identical to amino acids 21 to 282 of SEQ ID NO:4 or amino acids 21 to 252 of the polypeptide of SEQ ID NO:5; and
   (ii) an albumin at the N-terminal side of the mature D1L3 enzyme, and
   wherein the albumin and the mature D1L3 enzyme are adjoined via a peptide/polypeptide linker.

3. The D1L3 variant of claim 2, wherein the D1L3 variant has a C-terminal deletion of at least 10 contiguous amino acids corresponding to amino acids 296-305 of the polypeptide of SEQ ID NO:4.

4. The D1L3 variant of claim 1, wherein the D1L3 variant has an amino acid substitution at the position corresponding to position 101 of the polypeptide of SEQ ID NO: 4.

5. The D1L3 variant of claim 2, wherein the linker is flexible, rigid, or comprises a protease cleavage site.

6. The D1L3 variant of claim 1, comprising a PEG conjugation to the amino acid corresponding to C68 and/or C194 of the polypeptide of SEQ ID NO: 4.

7. The D1L3 variant of claim 1, wherein the D1L3 variant comprises one or more substitutions at positions corresponding to positions in the polypeptide of SEQ ID NO: 4 or the polypeptide of SEQ ID NO: 5 that comprise an arginine residue or a lysine residue.

8. A pharmaceutical composition comprising the D1L3 variant of claim 1, and a pharmaceutically acceptable carrier.

9. The D1L3 variant of claim 1, wherein the D1L3 variant is a fusion protein comprising:
   a mature D1L3 enzyme, wherein the mature D1L3 enzyme:
      lacks the signal peptide corresponding to amino acids 1 to 20 of the polypeptide of SEQ ID NO: 4 or SEQ ID NO:5, and
      comprises an amino acid sequence that is at least 95% identical to amino acids 21 to 282 of SEQ ID NO: 4 or amino acids 21 to 252 of SEQ ID NO: 5, and
   wherein the half-life extending moiety is fused or conjugated at the C-terminal side of the mature D1L3 enzyme.

10. The D1L3 variant of claim 9, wherein the half-life extending moiety is an Fc domain.

11. The D1L3 variant of claim 9, wherein the half-life extending moiety is an albumin.

12. The D1L3 variant of claim 9, wherein the albumin comprises an amino acid sequence that has at least 90% sequence identity to the amino acid sequence of SEQ ID NO: 39.

13. The D1L3 variant of claim 9, wherein the D1L3 variant has at least 97% sequence identity to amino acids 21 to 282 of the polypeptide of SEQ ID NO: 4.

14. The D1L3 variant of claim 9, wherein the D1L3 variant has a C-terminal deletion of at least 20 contiguous amino acids corresponding to amino acids 286-305 of the polypeptide of SEQ ID NO:4.

15. The D1L3 variant of claim 9, wherein the D1L3 variant has a C-terminal deletion of at least 10 contiguous amino acids corresponding to amino acids of the polypeptide of 296-305 of the polypeptide of SEQ ID NO:4.

16. The D1L3 variant of claim 9, wherein the D1L3 variant has a C-terminal deletion of at least 15 contiguous amino acids corresponding to amino acids 291-305 of the polypeptide of SEQ ID NO:4.

17. The D1L3 variant of claim 9, wherein the D1L3 variant has a deletion of the entire C-terminal basic domain corresponding to amino acids 283-305 of the polypeptide of SEQ ID NO:4.

18. The D1L3 variant of claim 9, further comprising a linker linking the half-life extending moiety and the mature D1L3 enzyme.

19. The D1L3 variant of claim 18, wherein the linker is a flexible linker.

* * * * *